(12) United States Patent
Wang et al.

(10) Patent No.: US 8,637,515 B2
(45) Date of Patent: Jan. 28, 2014

(54) POLYMORPHS OF BRIMONIDINE PAMOATE

(71) Applicant: Bausch & Lomb Incorporated, Rochester, NY (US)

(72) Inventors: Hongna Wang, Portland, ME (US); Stephen R. Davio, Fairport, NY (US); Gregory L. McIntire, Florham Park, NJ (US); Michael Hall, Albany, NY (US); Shazad Suchit, Guilderland, NY (US); Jon Summersett, Guilderland, NY (US); Brent Whitehead, Piscataway, NJ (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 13/826,516

(22) Filed: Mar. 14, 2013

(65) Prior Publication Data

US 2013/0203761 A1    Aug. 8, 2013

Related U.S. Application Data

(62) Division of application No. 13/233,052, filed on Sep. 15, 2011, now Pat. No. 8,420,648, which is a division of application No. 12/604,427, filed on Oct. 23, 2009, now Pat. No. 8,034,813.

(60) Provisional application No. 61/115,711, filed on Nov. 18, 2008.

(51) Int. Cl.
*A61K 31/495* (2006.01)

(52) U.S. Cl.
USPC .......................................... 514/249; 544/353

(58) Field of Classification Search
USPC .......................................... 514/249; 544/353
See application file for complete search history.

(56) References Cited

U.S. PATENT DOCUMENTS

| | | |
|---|---|---|
| 4,521,210 A | 6/1985 | Wong |
| 4,853,224 A | 8/1989 | Wong |
| 4,997,652 A | 3/1991 | Wong |
| 5,164,188 A | 11/1992 | Wong |
| 5,443,505 A | 8/1995 | Wong et al. |
| 5,501,856 A | 3/1996 | Ohtori et al. |
| 5,766,242 A | 6/1998 | Wong et al. |
| 5,824,072 A | 10/1998 | Wong |
| 5,869,079 A | 2/1999 | Wong et al. |
| 6,074,661 A | 6/2000 | Olejnik et al. |
| 6,194,415 B1 | 2/2001 | Wheeler et al. |
| 6,331,313 B1 | 12/2001 | Wong et al. |
| 6,369,116 B1 | 4/2002 | Wong et al. |
| 6,699,493 B2 | 3/2004 | Wong |
| 2006/0257452 A1 | 11/2006 | Hughes et al. |

OTHER PUBLICATIONS

Danylkova et al., "Neuroprotective effects of brimonidine treatment in a rodent model of ischemic optic neuropathy," Exp Eye Res, 2007 (vol. 84) (pp. 293-301).
Lafuente Lopez-Herrera et al., "Transient Ischemia of the Retina Results in Altered Retrograde Axoplasmic Transport: Neuroprotection with Brimonidine," Exp Neurology, 2002 (vol. 178) (pp. 243-258).
Sweetman (Ed.), "Nanionic Surfactants," Martindale The Complete Drug Reference, 2005, 34th Edition, Pharma Press (pp. 1411-1416).

*Primary Examiner* — Douglas M Willis
(74) *Attorney, Agent, or Firm* — Toan P. Vo

(57) ABSTRACT

A polymorph of brimonidine pamoate having the formula

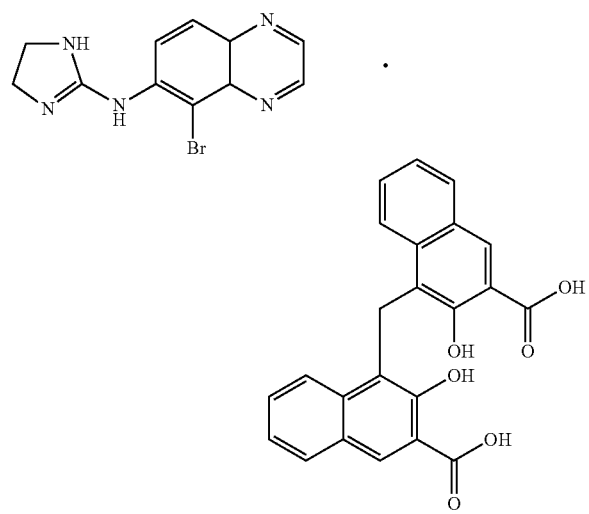

exhibits characteristics disclosed herein. The polymorph is included in a composition, device, or implant for use in the treatment or control of elevated intraocular pressure or in the neuroprotection of components of a neurological tissue to prevent progressive degeneration of such components. In particular, such a composition, device, or implant can be used to provide neuroprotection to cells and components of the optic nerve system.

5 Claims, 31 Drawing Sheets

POLYMORPHS OF BRIMONIDINE PAMOATE

CROSS-REFERENCE

This application is a divisional of application Ser. No. 13/233,052 filed Sep. 15, 2011, which is a divisional of application Ser. No. 12/604,427, filed Oct. 23, 2009, which claims the benefit of Provisional Patent Application No. 61/115,711 filed Nov. 18, 2008, which is incorporated by reference herein.

BACKGROUND OF THE INVENTION

The present invention relates to polymorphs of brimonidine pamoate, compositions comprising such polymorphs, and methods of treating or controlling diseases using such polymorphs. In particular, the present invention relates to stable polymorphs of brimonidine pamoate and such compositions comprising such polymorphs for sustained release thereof.

Polymorphism is a property of a substance to exist in more than one solid state crystal structures. The various polymorphic forms—polymorphs—of a crystal have different crystal lattices and, thereby, different physical and chemical properties, such as density, hardness, chemical stability, solubility, rate of dissolution in different solvents, melting point, phase transformation, hygroscopicity, interactions with biological systems, etc. In addition, the term "pseudopolymorphisms" has been applied to different hydrates and solvates of a crystalline material in which water or solvent molecules have been built into the crystal lattice.

Brimonidine, 5-bromo-6-(2-imidazolidinylideneamino) quinoxaline (Formula I), is an $\alpha_2$ selective adrenergic receptor agonist that has been used in the treatment of open-angle glaucoma by decreasing aqueous humor production and increasing uveoscleral outflow.

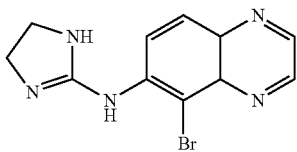

(I)

For this use, topical ophthalmic solutions have been formulated and the tartrate salt of brimonidine has been used to provide increased solubility of brimonidine. The solubility of brimonidine tartrate is 34 mg/mL in water, and 2.4 mg/mL in a pH 7.0 phosphate buffer while the solubility of brimonidine freebase is negligible in water (see; e.g., U.S. Patent Application Publication 2006/0257452).

Recent studies suggested that brimonidine eye drops may have a neuroprotective effect in a rodent model of ischemic-induced optic nerve cell death. N. O. Danylkova et al., *Exp. Eye Res.*, Vol. 84, 293 (2007); M. P. Lafuente et al., *Exp. Eye Res.*, Vol. 74, 1981 (2002). However, topical application of brimonidine may not be the most effective manner to provide therapeutic effect to neurological tissues in the back of the eye because of the rapid clearance of topically applied compositions.

Intravitreal delivery of brimonidine can provide better access of the drug to the tissues in the back of the eye. Such delivery can be achieved by injecting a liquid-containing composition into the vitreous, or by placing polymeric drug delivery systems, such as implants and microparticles, into the vitreous. Examples of biocompatible implants for placement in the eye have been disclosed in a number of patents, such as U.S. Pat. Nos. 4,521,210; 4,853,224; 4,997,652; 5,164,188; 5,443,505; 5,501,856; 5,766,242; 5,824,072; 5,869,079; 6,074,661; 6,331,313; 6,369,116; and 6,699,493. However, intravitreal administration of drugs should be as infrequent as possible to avoid unnecessary disturbance of the eye.

Therefore, it is very desirable to provide stable brimonidine salts for the preparation of sustained-release compositions. It is also very desirable to provide brimonidine salts that are stable in the vitreous humor. In addition, it is also very desirable to provide such brimonidine salts for duration in ocular environments where they can provide effective neuroprotection to the optic nerve system.

SUMMARY

In general, the present invention provides polymorphs of brimonidine pamoate.

In one aspect, the present invention provides stable or substantially stable polymorphs of brimonidine pamoate.

In another aspect, the present invention provides thermodynamically stable brimonidine pamoate polymorphs.

In another aspect, the present invention provides at least polymorphic forms A, B, C, D, E, and F (as designated herein) of brimonidine pamoate, each having distinguishing characteristics disclosed herein.

In still another aspect, the present invention provides brimonidine pamoate polymorph Form F characterized by an X-ray powder diffraction ("XRPD") spectrum that comprises peaks at 2θ angles of 7.1, 9.8, 17.8, and 25.5°±0.2°.

In yet another aspect, the present invention provides brimonidine pamoate polymorph Form F characterized by a Raman spectroscopy spectrum that comprises peaks at 145.1, 156.3, 1336.8, 1364.4, and 1412.5 cm$^{-1}$.

In a further aspect, the present invention provides brimonidine pamoate polymorph Form E characterized by an XRPD spectrum that comprises peaks at 2θ angles of 7.7, 8.0, 13.1, and 21.2°±0.2°.

In yet another aspect, the present invention provides brimonidine pamoate polymorph Form E characterized by a Raman spectroscopy spectrum that comprises peaks at 1339.9, 1368.7, 1396.1, 1403.1, and 1410.8 cm$^{-1}$.

In still another aspect, the present invention provides brimonidine pamoate polymorph Form B characterized by an XRPD spectrum that comprises peaks at 2θ angles of 9.7, 14.6, 25.9, and 26.5°±0.2°.

In yet another aspect, the present invention provides brimonidine pamoate polymorph Form B characterized by a Raman spectroscopy spectrum that comprises peaks at 1335.6, 1364.6, 1404.4, 1410.7, and 1462.1 cm$^{-1}$.

In still another aspect, the present invention provides brimonidine pamoate polymorph Form C characterized by an XRPD spectrum that comprises peaks at 2θ angles of 7.7, 12.8, 13.4, and 23.8°±0.2°.

In yet another aspect, the present invention provides brimonidine pamoate polymorph Form C characterized by a Raman spectroscopy spectrum that comprises peaks at 161.5, 1344.8, 1354.1, 1367.9, and 1402.2 cm$^{-1}$.

In still another aspect, the present invention provides brimonidine pamoate polymorph Form D characterized by an XRPD spectrum that comprises peaks at 2θ angles of 7.5, 12.8, 24.5, and 27.1°±0.2°.

In yet another aspect, the present invention provides brimonidine pamoate polymorph Form D characterized by a Raman spectroscopy spectrum that comprises peaks at 157.4, 1270.4, 1341.5, 1355.5, and 1403.0 cm$^{-1}$.

In still another aspect, the present invention provides brimonidine pamoate polymorph Form A characterized by an XRPD spectrum that comprises peaks at 2θ angles of 13.5, 20.6, 21.1, and 24.4°±0.2°.

In yet another aspect, the present invention provides brimonidine pamoate polymorph Form A characterized by Raman spectroscopy spectrum that comprises peaks at 1340.8, 1352.4, 1365.8, 1402.0, and 1460.3 cm$^{-1}$.

In still another aspect, the present invention provides a pharmaceutical composition comprising a polymorph of brimonidine pamoate selected from the group consisting of polymorph Forms A, B, C, D, E, F, and combinations thereof.

In still another aspect, the present invention provides a pharmaceutical composition comprising a polymorph of brimonidine pamoate selected from the group consisting of polymorph Forms B, C, D, E, F, and combinations thereof.

In a further aspect, the present invention provides a method for treating or controlling glaucoma in a subject. The method comprises administering to an ocular environment of the subject a composition that comprises at least a polymorph of brimonidine pamoate selected from the group consisting of brimonidine pamoate polymorph Forms A, B, C, D, E, F, and combinations thereof. In one embodiment, said treating or controlling is effected by reducing intraocular pressure ("IOP") in an affected eye of said subject.

In still another aspect, the present invention provides a method for effecting ocular neuroprotection in a subject. The method comprises administering to an ocular environment of the subject a composition that comprises at least a polymorph of brimonidine pamoate selected from the group consisting of brimonidine pamoate polymorph Forms A, B, C, D, E, F, and combinations thereof. In one embodiment, said composition is administered into a posterior segment of an eye of the subject in need of said neuroprotection.

Other features and advantages of the present invention will become apparent from the following detailed description and claims and the appended drawings.

DETAILED DESCRIPTION OF THE INVENTION

As used herein, the term "control" also includes reduction, alleviation, amelioration, and prevention.

As used herein, the term "stable" means incapable of changing in crystalline structure, as exhibited by a plurality of peaks in an XRPD pattern, at a time of two weeks after the initial preparation of the material.

As used herein, the term "neuroprotection" means the rescue of at least some cells or components of a nervous system that are not directly damaged by the primary cause of a disease or injury, but would otherwise undergo secondary degeneration without therapeutic intervention. In one aspect, neuroprotection can lead to preservation of the physiological function of these cells or components. In one aspect, such a nervous system is the optic nerve system. The cells or components of the optic nerve system include those being involved or assisting in conversion of photon to neurological signals and the transmission thereof from the retina to the brain for processing. Thus, the main cells or components of the optic nerve system include, but are not limited to, pigment epithelial cells, photoreceptor cells (rod and cone cells), bipolar cells, horizontal cells, amacrine cells, interplexiform cells, ganglion cells, support cells to ganglion cells, and optic nerve fibers.

In general, the present invention provides polymorphs of brimonidine pamoate.

In one aspect, such polymorphs comprise stable or substantially stable brimonidine pamoate polymorphs.

In another aspect, the present invention provides thermodynamically stable brimonidine pamoate polymorphs.

In still another aspect, the present invention provides at least polymorphic forms A, B, C, D, E, and F (as designated herein) of brimonidine pamoate, each having distinguishing characteristics disclosed herein.

In yet another aspect, the present invention provides at least polymorphic forms B, C, D, E, and F of brimonidine pamoate, each having distinguishing characteristics disclosed herein.

Brimonidine Pamoate Polymorph Form A

Figure 1:
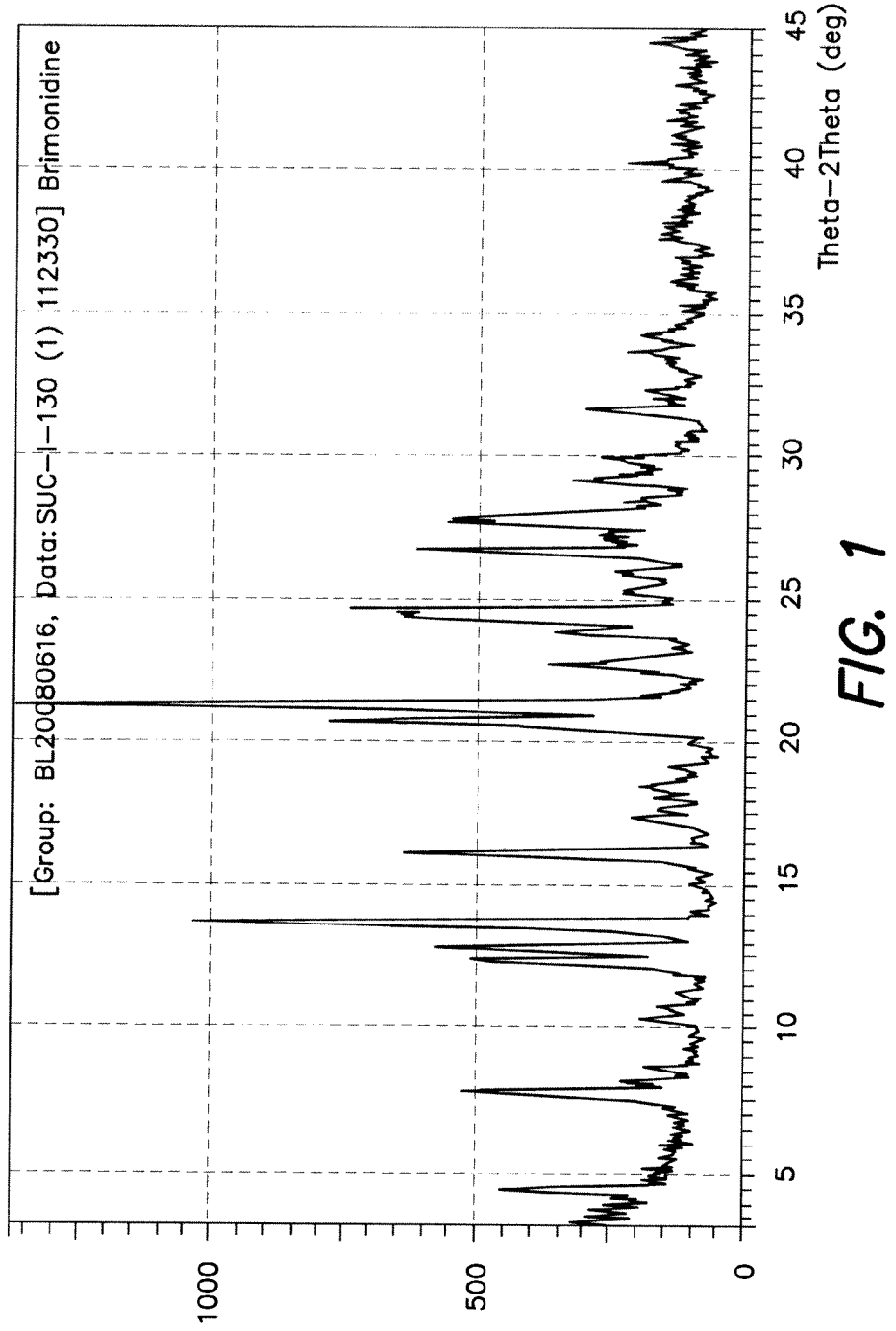
FIG. 1 shows an XRPD spectrum of brimonidine pamoate polymorph Form A.

In a 5 L 3-neck round bottom flask equipped with overhead stirrer, heating mantle, condenser, temperature probe, and $N_2$ inlet, 4.8 g of brimonidine (lot 1-080085) was dissolved in ethanol (2000 mL) at 65° C. Pamoic acid (1.05 eq, 19.0 mL, 0.5M in DMSO (dimethyl sulfoxide)) was then added. The resulting solution was stirred for 30 minutes at 65° C. and then cooled at 20° C./hour to ambient temperature. At the onset of the cooling profile, precipitation of solids was observed. The mixture stirred overnight at ambient temperature and was then filtered. The resulting solids were dried under vacuum at ambient temperature for 4 days before being analyzed by XRPD to confirm the solid form, designated as Form A. FIG. 1 shows an XRPD spectrum of brimonidine pamoate polymorph Form A (lot SUC-I-130(1)).

In one aspect, polymorph Form A is characterized by an XRPD spectrum comprising major peaks at 2θ angles of 13.5, 20.6, 21.1, and 24.4°±0.2°.

In another aspect, polymorph Form A is characterized by an XRPD spectrum comprising peaks at 2θ angles of 7.6, 12.2, 12.7, 13.5, 20.6, 21.1, 24.4, 26.5, and 27.7°±0.2°.

Figure 2:
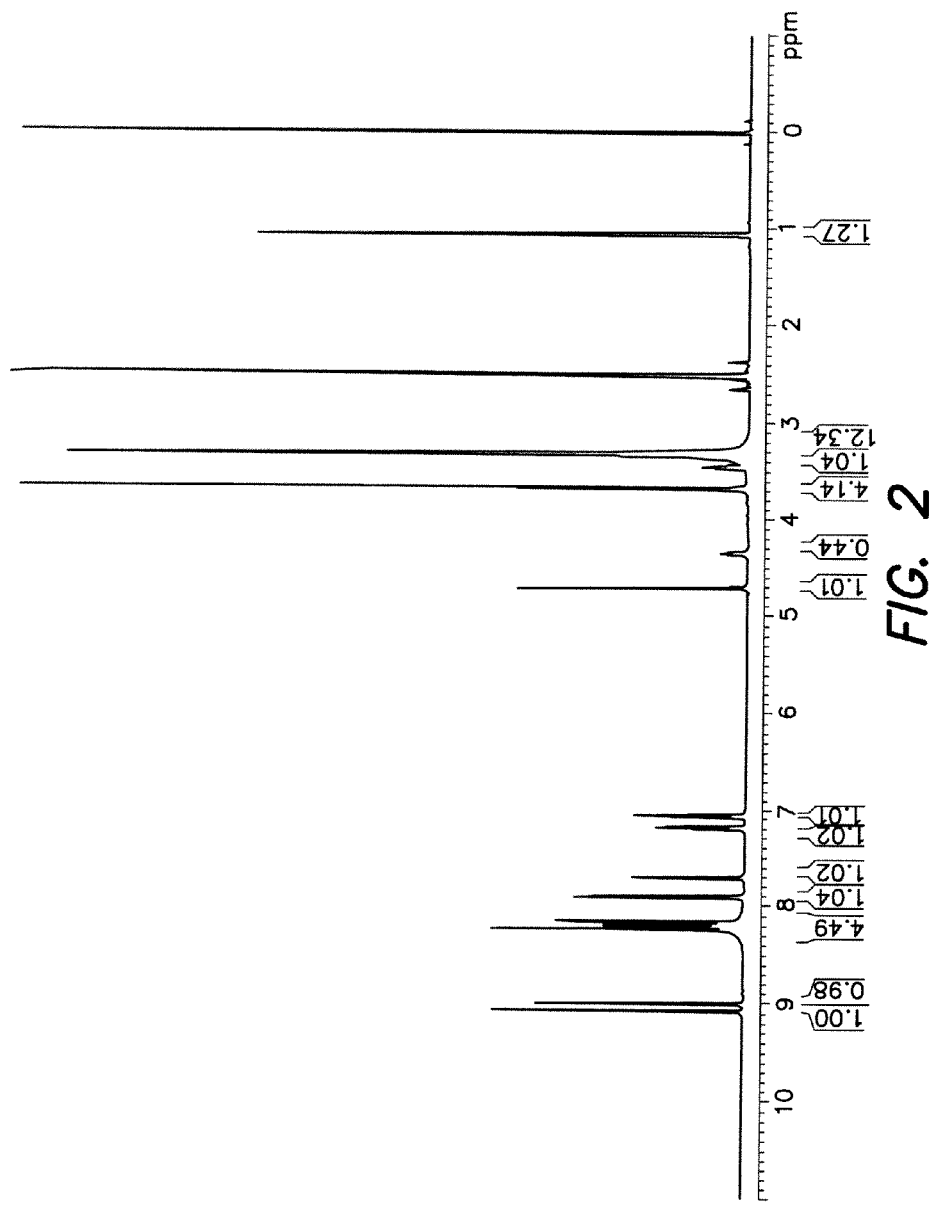
FIG. 2 shows an $^1$H NMR spectrum of brimonidine pamoate polymorph Form A.

$^1$H NMR analysis of this material showed approximately 3.7 wt % residual ethanol and a 0.5:1 pamoate to brimonidine ratio confirming the formation of a hemi-pamoate salt of brimonidine. FIG. 2 shows an NMR spectrum for brimonidine pamoate polymorph Form A (lot SUC-I-130(1).

Figure 3:
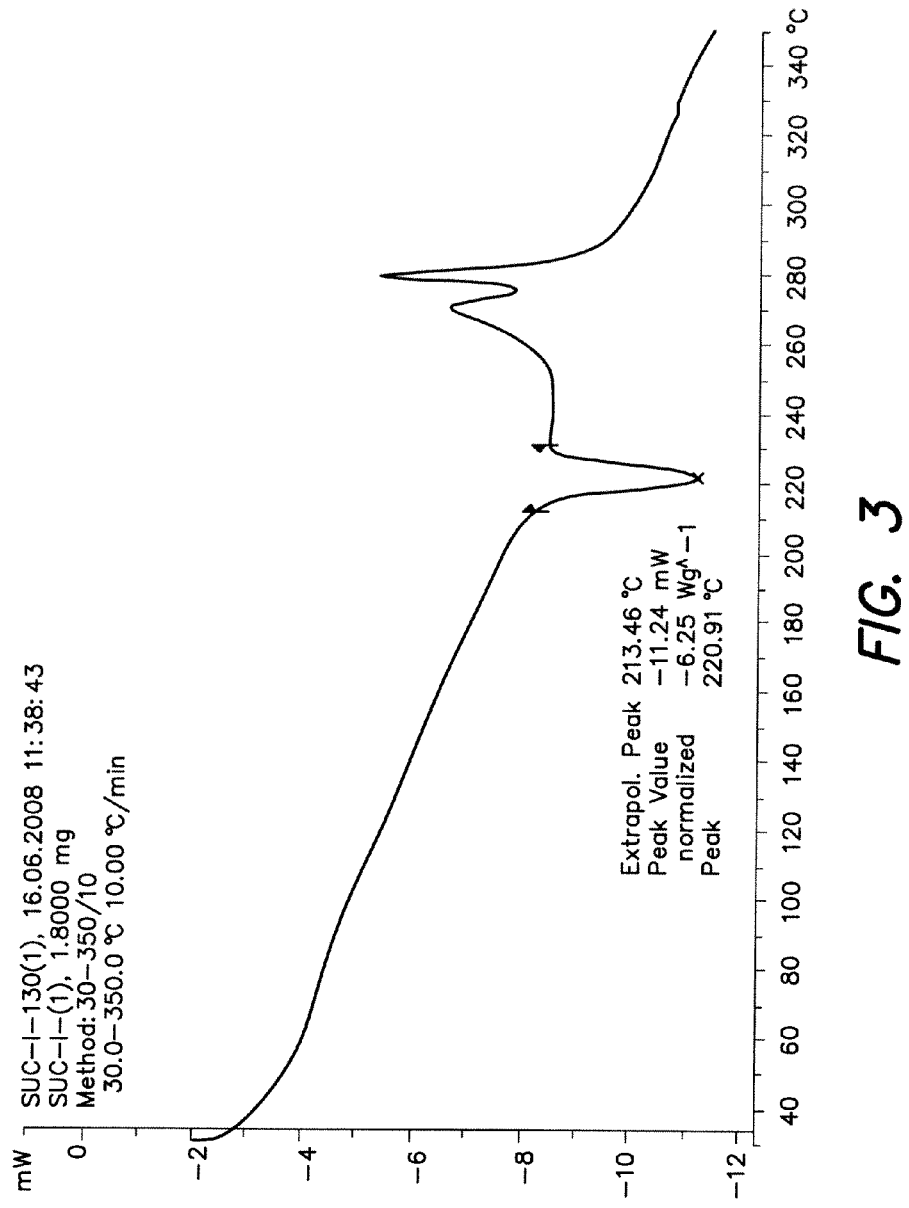
FIG. 3 shows a DSC curve of brimonidine pamoate polymorph Form A.
Figure 4:
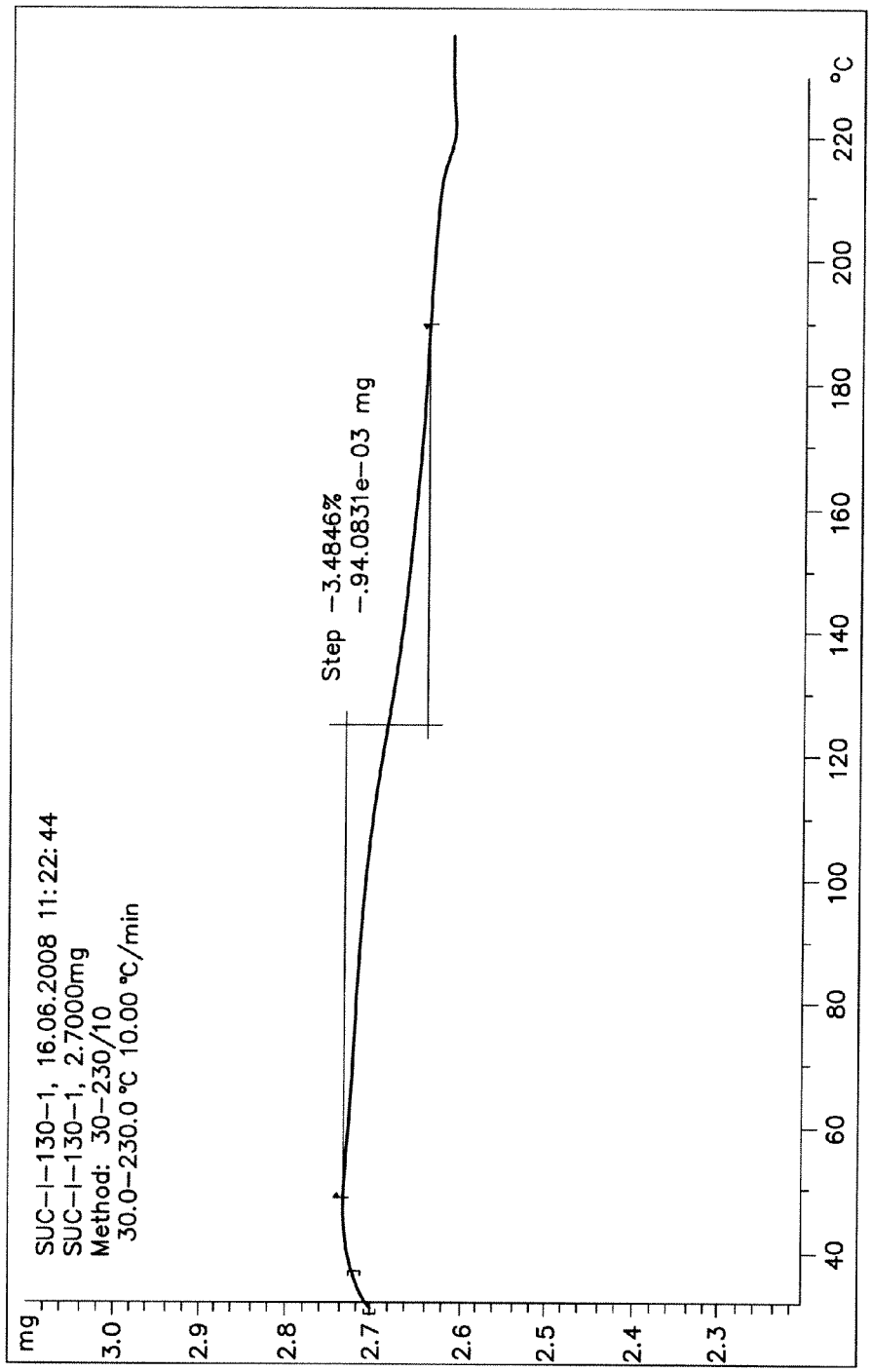
FIG. 4 shows a TGA curve of brimonidine pamoate polymorph Form A.

Thermal analysis of Form A showed a single DSC endotherm at 221° C. (see FIG. 3) attributed to the melting of the salt and 3.5% TGA weight loss through 190° C. (see FIG. 4) attributed to the removal of ethanol.

Figure 5:
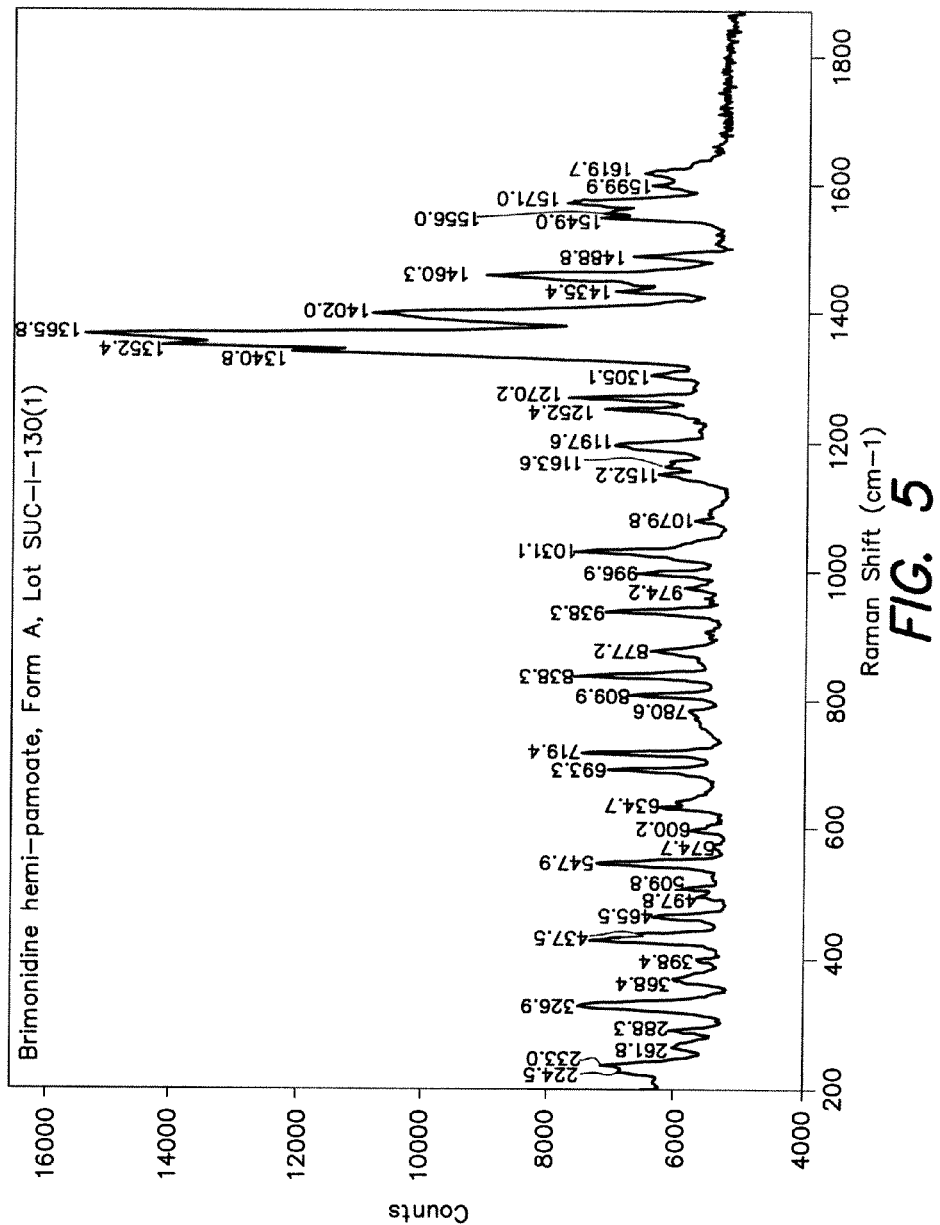
FIG. 5 shows a Raman spectroscopy spectrum of brimonidine pamoate polymorph Form A.

FIG. 5 shows a Raman spectroscopy spectrum of Form A (lot SUC-I-130(1), to be compared to Raman spectra of other polymorphs.

In one aspect, polymorph Form A is characterized by a Raman spectroscopy spectrum comprising major peaks at 1340.8, 1352.4, 1365.8, 1402.0, and 1460.3 cm$^{-1}$.

In another aspect, polymorph Form A is characterized by a Raman spectroscopy spectrum comprising peaks at 135.4, 169.3, 189.2, 233.0, 326.9, 547.9, 693.3, 719.4, 838.3, 938.3, 1031.1, 1197.6, 1252.4, 1270.2, 1340.8, 1352.4, 1365.8, 1402.0, 1460.3, 1549.0, 1556.0, and 1571.0 cm$^{-1}$.

Moisture sorption analysis of Form A showed this hemi-pamoate polymorph to be slightly hygroscopic, adsorbing 2.2 percent by weight ("wt %") water at 60 percent relative humidity ("% RH") and 2.5 wt % water at 90% RH. Upon desorption, no hysteresis or indication of hydrate formation was observed. XRPD analysis of the solids following moisture sorption analysis afforded a diffraction pattern which was consistent with the Form A starting material, indicating no polymorphic form conversion had occurred during the experiment.

Slurries of Form A were prepared in MeOH (methanol), THF (tetrahydrofuran), MIBK (methyl isobutyl ketone), toluene, water and EtOH (ethanol) as described below in an attempt to determine propensity of Form A to undergo form conversion in different solvent systems, as follows. Approximately 15-30 mg of brimonidine hemi-pamoate Form A was weighed into a 1 dram vial and 1.0 mL of solvent (MeOH, THF, MIBK, toluene, water, or EtOH) was added to each vial and allowed to stir magnetically at ambient conditions for three weeks (see summary results in Table 1). Following one week intervals, samples were isolated by centrifugation and dried in vacuo at ambient temperature overnight and analyzed by XRPD to check for polymorphic form conversion.

TABLE 1

Summary of Three Weeks Slurry Experiments

| Lot No. | Hemi-Pamoate (Form A) (mg) | Hemi-Pamoate seeds (Form B) (mg) | Primary Solvent (mL) | Temperature (° C.) | Form by XRPD (1 week) | Form by XRPD (2 weeks) | Form by XRPD (3 weeks) |
|---|---|---|---|---|---|---|---|
| SUC-I-132(1) | 32.60 | — | MeOH 1 | Ambient | A | A | A |
| SUC-I-132(2) | 31.40 | — | THF 1 | Ambient | E | E | E |
| SUC-I-132(3) | 33.30 | — | MIBK 1 | Ambient | A | A | A |
| SUC-I-132(4) | 32.30 | — | Toluene 1 | Ambient | A | A | A |
| SUC-I-132(5) | 34.20 | — | Water (magnetic stirring) 1 | Ambient | A | A | B |
| SUC-I-132(6) | 33.18 | — | EtOH 1 | Ambient | A | A | A |
| SUC-I-132(7) | 37.40 | — | Water (Shaker) 1 | Ambient | A | A | n/a |
| SUC-I-132(8) | 14.9 | 1.4 | Water 1 | Ambient | B | B | n/a | n/a—Sample not analyzed

Solids isolated from a slurry of Form A in THF (lot SUC-I-132(2)) following one week of equilibration, afforded a unique XRPD pattern compared to the diffraction patterns of Forms A, B, C, D and F. Further characterization of this unique crystalline solid, designated as Form E, is detailed herein below. These findings indicate that Form E is more stable in THF than Form A. XRPD analysis of solids isolated from a slurry of Form A in water (lot SUC-I-132(5)) following three weeks of equilibration showed conversion to Form B. These findings suggest that Form B is more stable in water than Form A. Form A was also observed to convert to Form B during the aqueous solubility experiment after overnight equilibration in water. As a result, the aqueous solubility of Form A was not determined. No form conversion was observed in the remaining slurry solvents as shown in Table 1.

Figure 6:
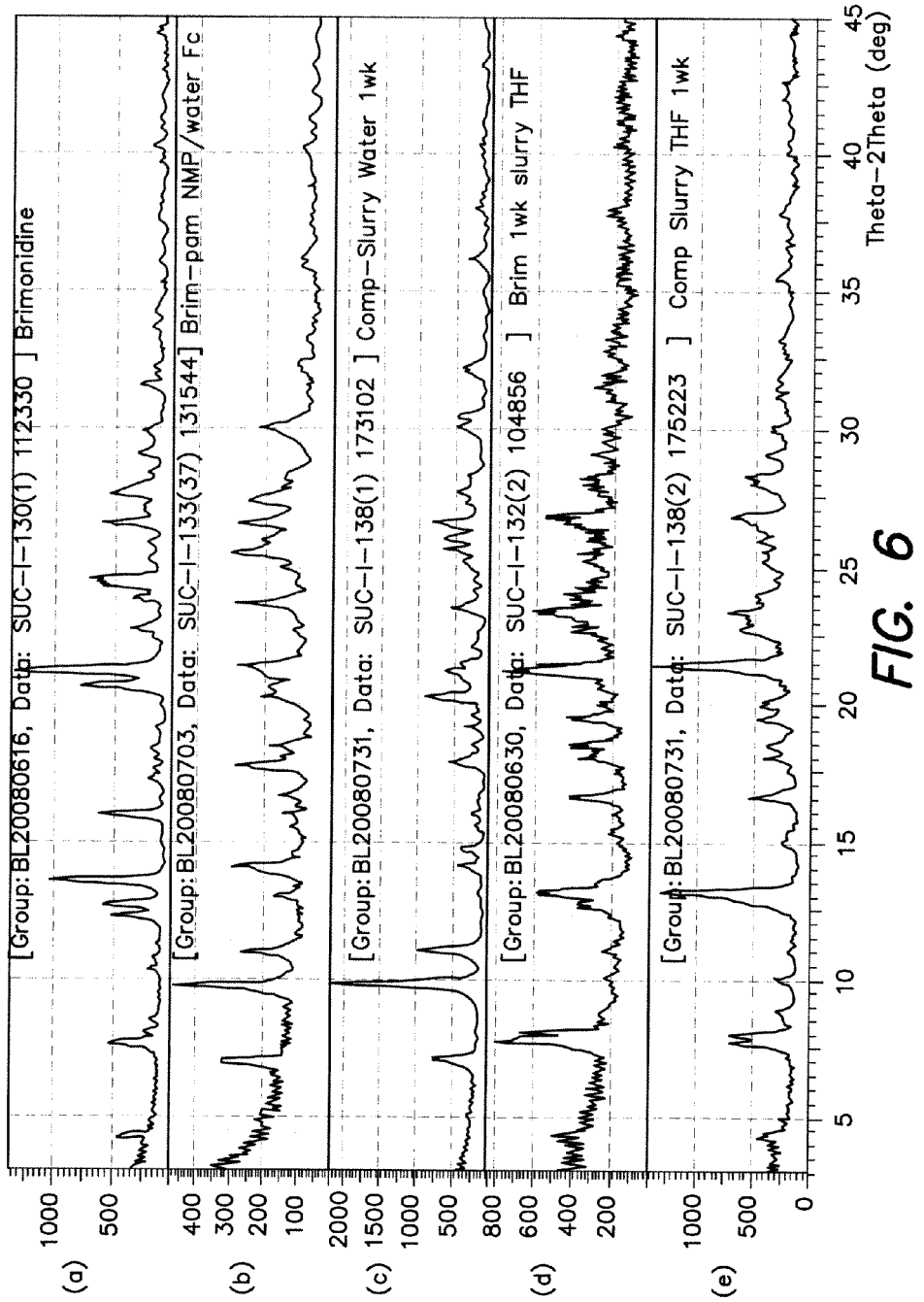
FIG. 6 shows An XRPD stack plot of brimonidine hemipamoate competitive slurry samples (a) starting material, lot SUC-I-130(1), Form A, (b) lot SUC-I-133(37), Form F, (c) lot SUC-I-138(1), isolated following one week of Forms A, C, D and E slurry in water, (d) lot SUC-I-132(2), Form E, and (e) lot SUC-I-138(2) isolated following one week of Forms A, B, C and D slurry in THF. Patterns (c) and (e) were found to be consistent with patterns (b) and (d), Forms F and E respectively.

In an effort to elucidate the relative thermodynamic stability of Form A with respect to the other crystalline forms, competitive slurry experiments were performed as follows. Approximately 15 mg of brimonidine hemi-pamoate Form A and 3 mg of either Forms B, C, D and E were weighed into a 1-dram vial and 1.0 mL of solvent (water or THF) was added (Table 2). Following one week of stirring at ambient conditions, the samples were isolated by centrifugation and dried in vacuo at ambient temperature overnight at 30 inches of Hg. After drying, the samples were analyzed by XRPD to check for form conversion. A one-week slurry comprising Forms A, B, C and D in THF revealed that Form A will convert to the most stable anhydrate form (Form E) as shown in FIG. 6. These findings are consistent with results obtained from the 1 week slurry of Form A in THF. Slurries comprising Forms A, C, D and E in water showed conversion to Form F after one week of equilibration (Table 2). These results indicate that Form F, like Form B, is also relatively stable in water.

TABLE 2

Competitive Slurries of Brimonidine Hemi-Pamoate Forms

| Lo No. | Weight (mg) | | | | | Solvent (mL) | Temp (° C.) | XRPD (1 week) |
|---|---|---|---|---|---|---|---|---|
| | SUC-I-130(1) (Form A) | SUC-I-132(8) (Form B) | SUC-I-134(37) (Form C) | SUC-I-134(25) (Form D) | SUC-I-132(2) (Form E) | | | |
| SUC-I-138(1) | 15.903 | — | 3.331 | 3.432 | 3.501 | Water (1.0) | RT | Crystalline (Form F) |
| SUC-I-138(2) | 16.559 | 3.373 | 3.819 | 3.237 | — | THF (1.0) | RT | Crystalline (Form E) |

The solid state stability of different polymorphs was assessed at elevated temperature and humidity as follows.

Elevated Temperature Stability

Approximately 3-5 mg of brimonidine hemi-pamoate Form A, B, C, D, or E were weighed into individual 1-dram vials and stored uncapped at 60° C. After one week of exposure, the samples were analyzed by XRPD to check for form conversion and HPLC analysis to check for potential degradation. After one week of storage at 60° C., Form A was observed to be stable by XRPD and HPLC (Table 3).

Elevated Humidity Stability

Approximately 1-10 mg of brimonidine hemi-pamoate Form A, F, or C were transferred to vial caps (uncapped) and stored in a closed container with saturated barium chloride dihydrate ($BaCl_2.2H_2O$). This solution results in 88% RH environment. After two weeks of storage the crystalline form was determined by XRPD and solid inspected for deliquescence. Forms A, C, and F were observed to be stable after two weeks of storage at elevated relative humidity (88% RH), showing no sign of deliquescence or change in crystalline form by XRPD (Table 4).

TABLE 3

Thermal Stress Study of Brimonidine Hemi-Pamoate Forms

| Lot No. | Starting Material Lot (Form) | Weight (mg) | Temp. (° C.) | XRPD (1 week) | HPLC (% purity) |
|---|---|---|---|---|---|
| SUC-I-138(3) | SUC-I-130(1) (Form A) | ~3-5 | 60 | Crystalline (Form A) | 100.0 |
| SUC-I-138(4) | SUC-I-132(8) (Form B) | ~3-5 | 60 | Crystalline (Form B) | 100.0 |
| SUC-I-138(5) | SUC-I-133(13) (Form C) | ~3-5 | 60 | Semi-cryst. (Form C) | 97.9 |
| SUC-I-138(6) | SUC-I-134(7) (Form D) | ~3-5 | 60 | Crystalline (Form D) | 96.7 |
| [1]SUC-I-138(7) | SUC-I-138(2) (Form E) | ~3-5 | 60 | Semi-cryst. (Form E) | 100.0 |

[1]Sample exposed to elevated conditions for 6 days

TABLE 4

Humidity Chamber Study of Brimonidine Hemi-Pamoate Forms

| NB Code | Starting Material Lot(s) (mg) | % RH | Initial Form | Form by XRPD (2 week) | Visual inspection (2 week) |
|---|---|---|---|---|---|
| SUC-I-136(1) | SUC-I-130(1) (25.22) | 88 | A | A | No deliquescence |
| SUC-I-136(2) | SUC-I-133(37) SUC-I-133(38) (4.3) | | F | F | No deliquescence |
| SUC-I-136(3) | SUC-I-133(34) (7.4) | | C | C | No deliquescence |

Brimonidine Pamoate Polymorph Form B

Figure 7:
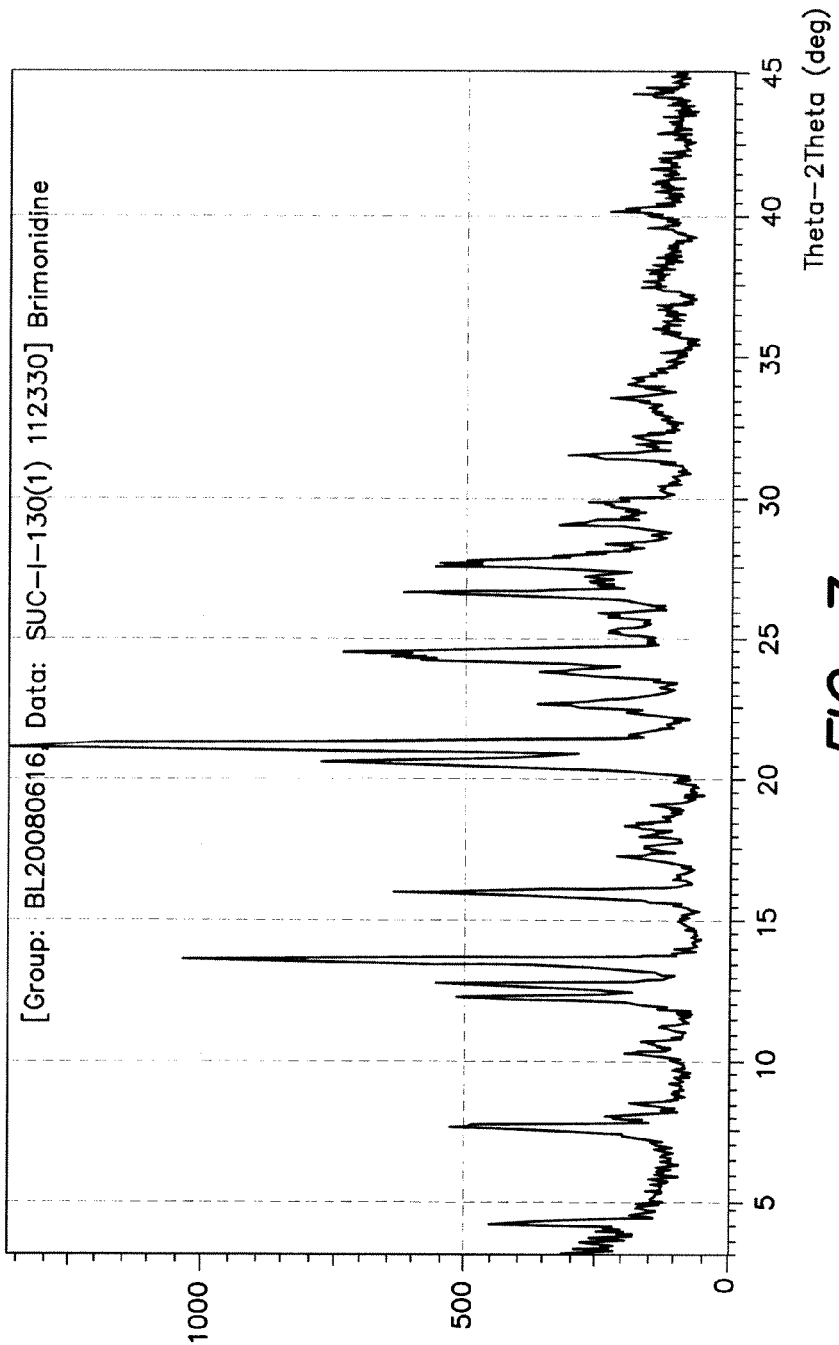
FIG. 7 shows an XRPD spectrum of brimonidine pamoate polymorph Form B.

Form B was identified at first from a two-week slurry of Form A in water. In addition, Form B was also observed from slow- and fast-cooling (see procedures disclosed below) crystallizations of Form A in DMF/water binary solvent. Form B was fully characterized as described below. FIG. 7 shows an XRPD spectrum of Form B (lot SUC-I-133(36)).

Fast-Cooling Profile

Approximately 20-30 mg of brimonidine hemi-pamoate (lot SUC-I-130(1), Form A) was weighed to a 2-dram glass vial equipped with a stir bar. The starting material was dissolved in a minimal amount (typically 1-7 mL, depending on the ability of the solvent to dissolve the starting solid) of primary solvent at about 55° C. Each solution was passed through a 0.45 μm syringe filter into a preheated vial to remove any undissolved starting material. Following the polish filtration the vials were placed in a refrigerator to achieve a fast cooling rate and left to equilibrate overnight. The following day, the vials were visually inspected for precipitation; those vials with little to no precipitation were gently scratched with a metal spatula to facilitate crystal growth and then allowed to equilibrate an additional 24 hours at 4° C. The resultant solids were either isolated by vacuum filtration or in instances of no precipitation were evaporated to dryness under a gentle stream of nitrogen. All samples were then dried overnight in vacuo at ambient temperature and analyzed by XRPD to determine the solid form.

Slow-Cooling Profile

Approximately 20-30 mg of brimonidine hemi-pamoate (lot SUC-I-130(1), Form A) was weighed to a 2-dram glass vial equipped with a stir bar. The starting material was dissolved in a minimal amount of primary solvent at about 55° C. Each solution was passed through a 0.45 µm syringe filter into a preheated vial to remove any undissolved starting material. Following the polish filtration the samples were cooled to ambient temperature at the rate of 20° C./hour and also allowed to equilibrate overnight. The following day, the vials were visually inspected for precipitation; those vials with little to no precipitation were gently scratched with a metal spatula to facilitate crystal growth and then allowed to equilibrate an additional 24 hours at ambient temperature. The resultant solids were either isolated by vacuum filtration or in instances of no precipitation were evaporated to dryness under a gentle stream of nitrogen. All samples were then dried overnight in vacuo at ambient temperature and analyzed by XRPD to determine the solid form.

In one aspect, polymorph Form B is characterized by an XRPD spectrum comprising major peaks at 2θ angles of 9.7, 14.6, 25.9, and 26.5°±0.2°.

In another aspect, polymorph Form B is characterized by an XRPD spectrum comprising peaks at 2θ angles of 7.0, 9.7, 10.9, 14.6, 19.0, 20.1, 23.4, 25.9, 26.5, and 27.7°±0.2°

Figure 8:
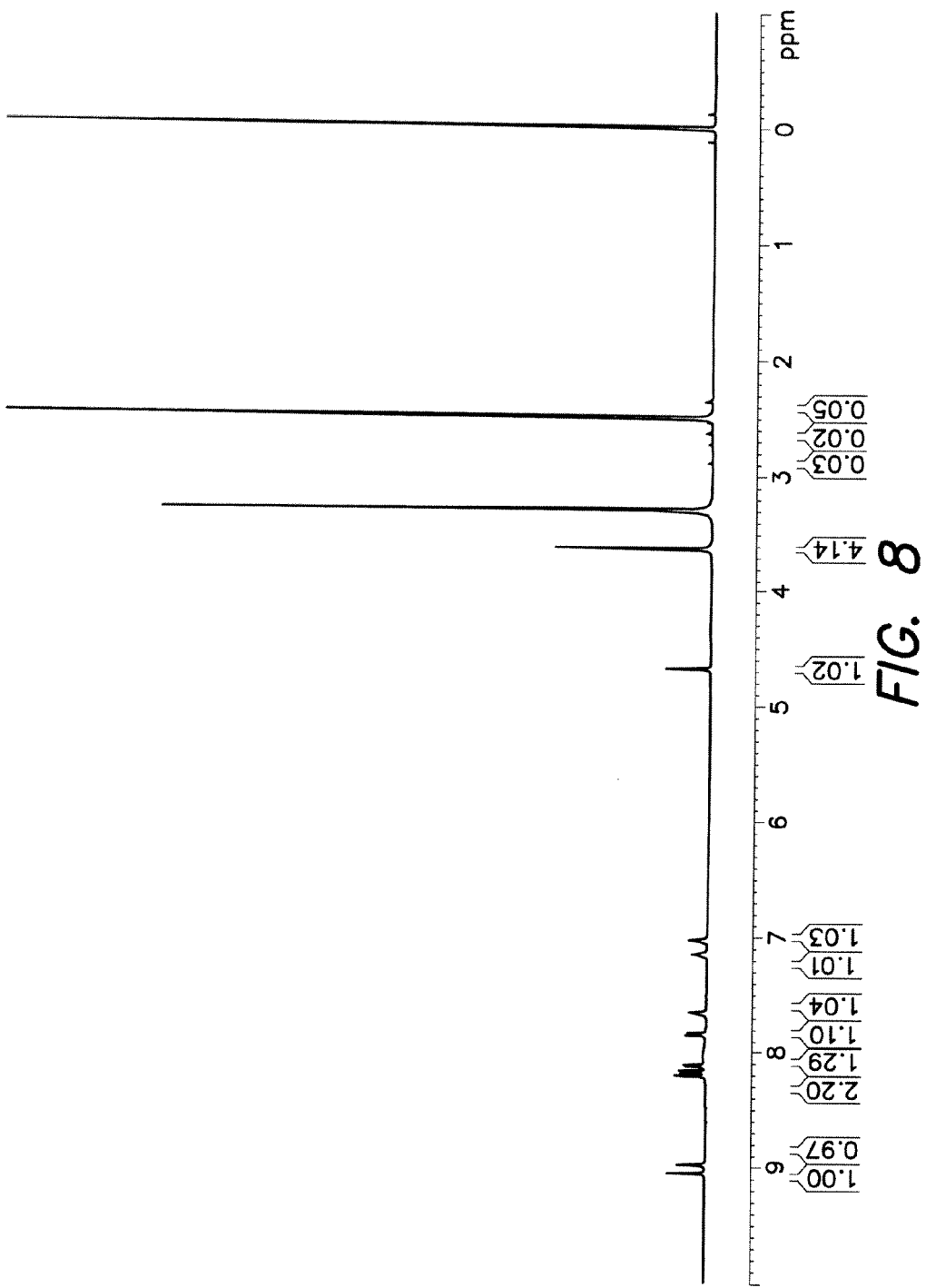
FIG. 8 shows an $^1$H NMR spectrum of brimonidine pamoate polymorph Form B.

$^1$H NMR analysis showed a 0.5:1 pamoate to brimonidine ratio confirming the formation of a hemi-pamoate salt of brimonidine with approximately 0.1 wt % residual DMF present. FIG. 8 shows an NMR spectrum for brimonidine pamoate polymorph Form B (lot SUC-I-133(36)).

Figure 9:
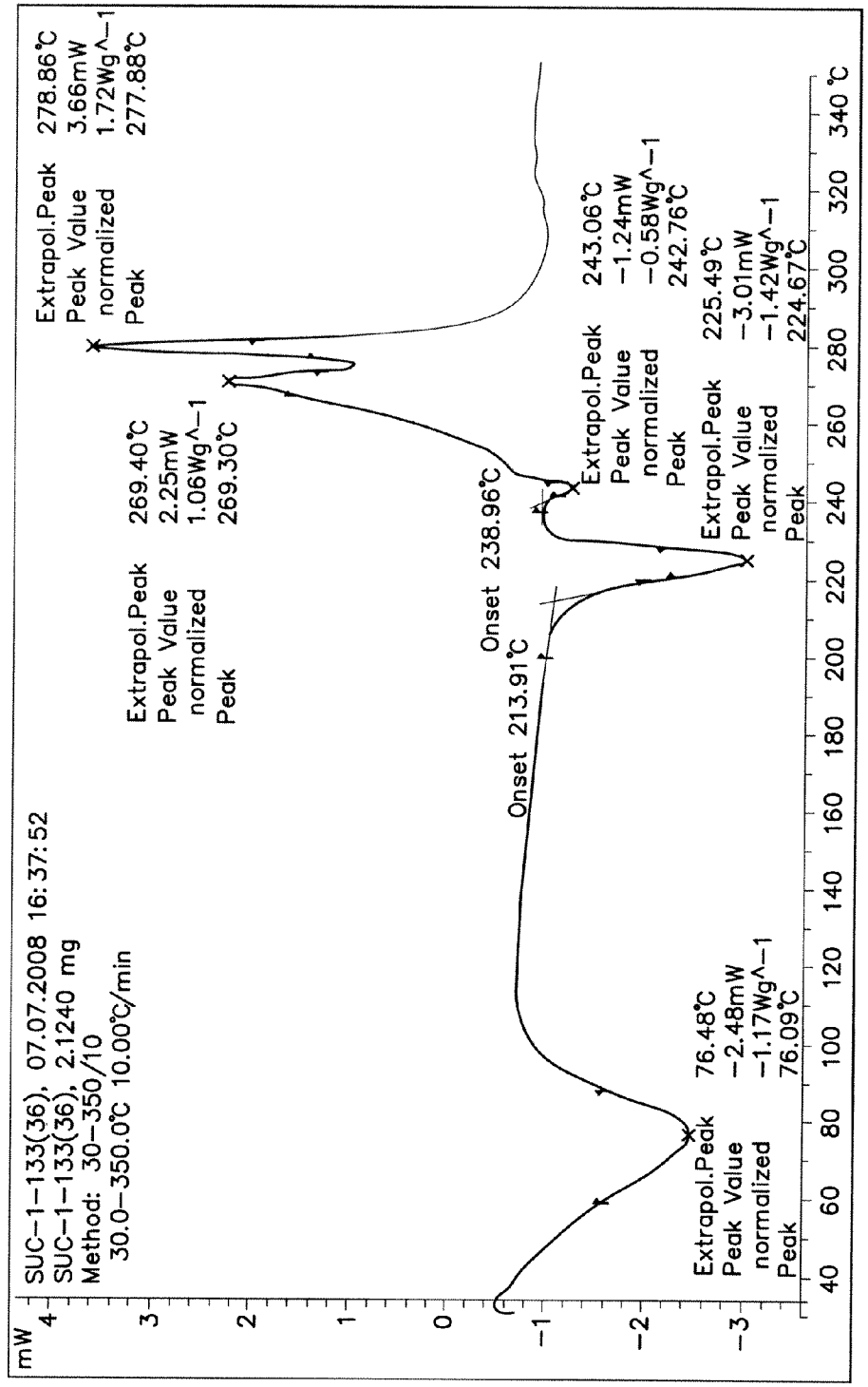
FIG. 9 shows a DSC curve of brimonidine pamoate polymorph Form B.
Figure 10:
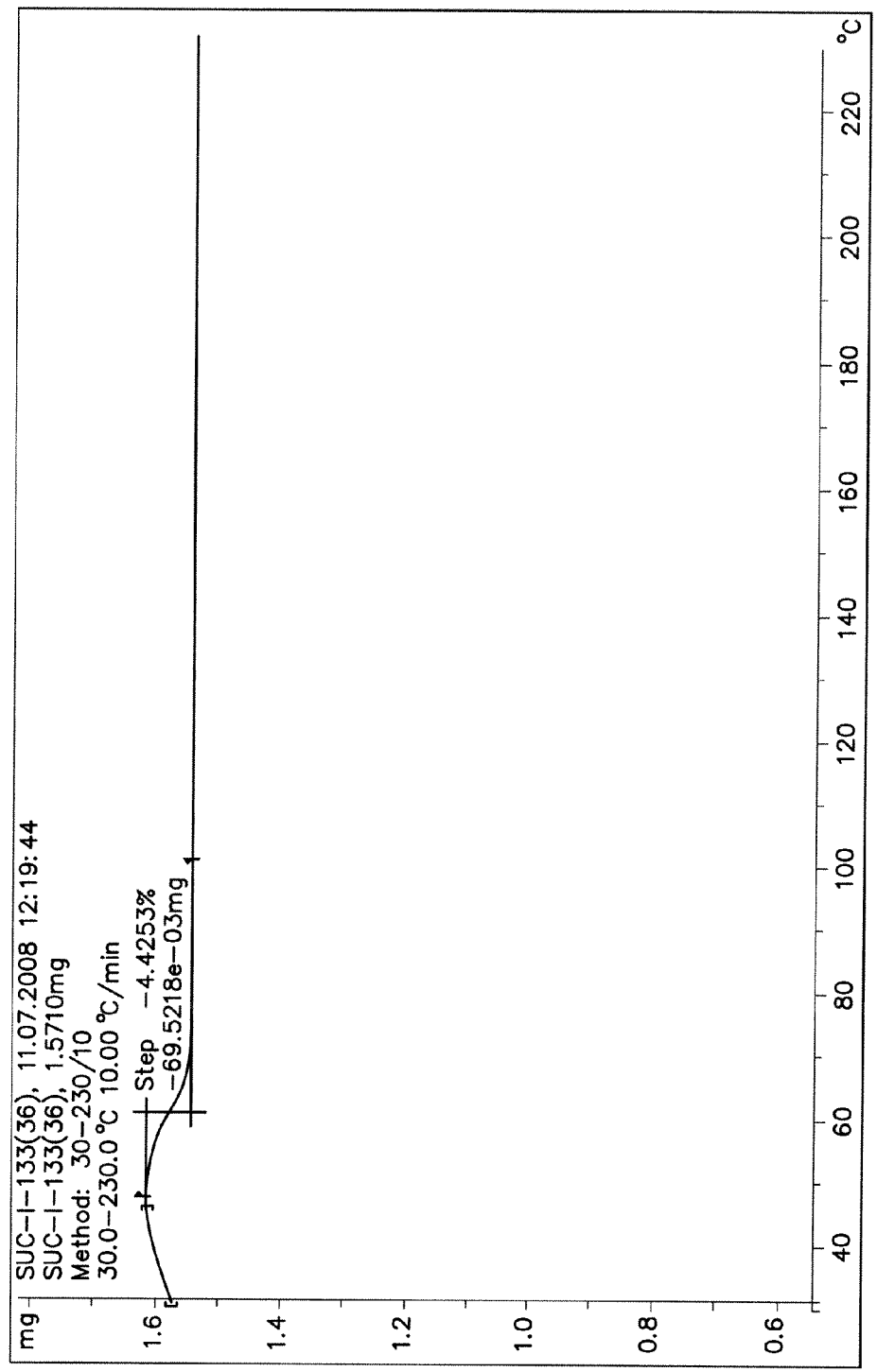
FIG. 10 shows a TGA curve of brimonidine pamoate polymorph Form B.

Thermal analysis of Form B showed DSC endothermic events at 76 and 225° C. (see FIG. 9) attributed to loss of residual solvent and melting of the crystalline salt. TGA analysis showed approximately 4.4% weight loss between 50 and 90° C. (see FIG. 10) likely attributed to the loss of water. Karl Fischer analysis of Form B showed 7.2 wt % water. Further characterization by Raman spectroscopy showed major spectral differences compared to anhydrate Forms A, C, D and E while only minor differences were observed compared to Form F. Thus, Form A slowly changed to Form B upon contacting water.

Moisture sorption analysis of lot SUC-I-134(36) showed that Form B adsorbed 5.4 wt % water at 60% RH and 5.8 wt % water at 90% RH. The water content stabilized at around 5-6 t % between 20-90% RH, coinciding with a sesqui-hydrate of brimonidine hemi-pamoate which would theoretically contain 5.4 wt % water. XRPD analysis of the dried solids following the experiment afforded a diffraction pattern which was consistent with Form B, indicating that the dehydrated material had converted back to Form B upon exposure to ambient conditions.

Figure 11:
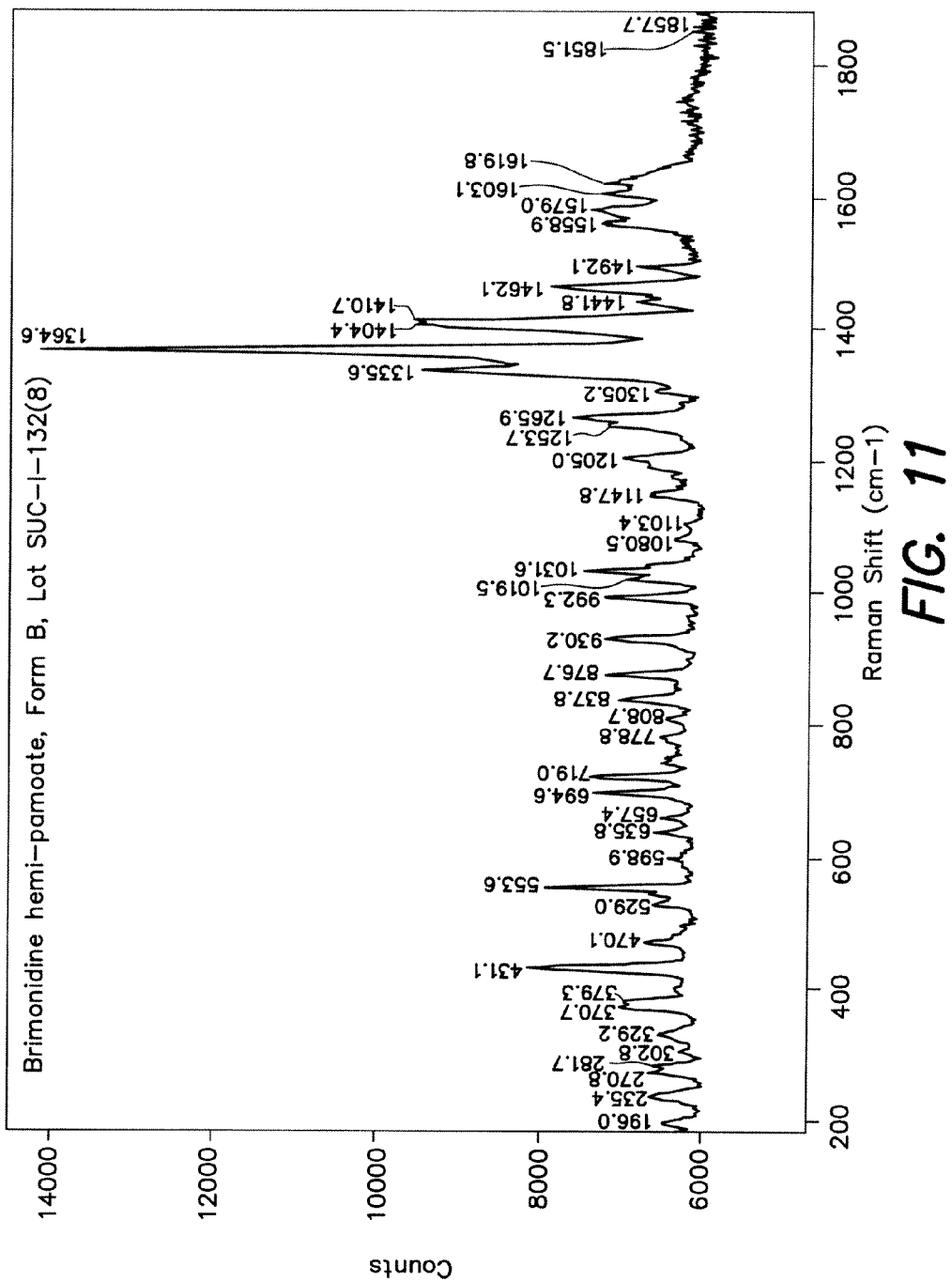
FIG. 11 shows a Raman spectroscopy spectrum of brimonidine pamoate polymorph Form B.

FIG. 11 shows a Raman spectroscopy spectrum of Form B (lot SUC-I-132(8)).

In one aspect, the present invention provides brimonidine pamoate polymorph Form B characterized by a Raman spectroscopy spectrum that comprises peaks at 1335.6, 1364.6, 1404.4, 1410.7, and 1462.1 cm$^{-1}$.

In another aspect, the present invention provides brimonidine pamoate polymorph Form B characterized by a Raman spectroscopy spectrum that comprises peaks at 106.9, 176.5, 235.4, 379.3, 431.1, 553.6, 694.6, 719.0, 1031.6, 1265.9, 1335.6, 1364.6, 1404.4, 1410.7, 1462.1, and 1579.0 cm$^{-1}$.

A competitive slurry of Forms (A, B, C and D) in THF revealed that along with the other starting forms, Form B also converted to Form E after one week of equilibration. Form B was observed to be relatively stable in water. This crystalline solid was isolated from a water slurry of Form A after 3 weeks and a mixture of Forms A and B after 1 week (Table 1). Form B was also observed during the aqueous solubility experiment following an overnight slurry of Form A in water (Table 2). The solubility of Form B was determined to be in the range of 0.005-0.02 mg/mL by HPLC. Mixtures of Forms B and Form F were also observed during the solubility experiments from individual slurries of Forms F, C, D and E. A competitive water slurry of Forms A, C, D, and E showed conversion to Form F (Table 2). Subsequent slurry studies demonstrated that aqueous slurries of mixtures of Form B and Form F always resulted in Form B after 7 or 14 days at either 40° C. or room temperature. Thus, Form B is the more stable polymorph in water of the two, both of which are more stable in water than any of the other polymorphs.

Form B was observed to be stable in the solid state after 1 week of storage at 60° C. HPLC and XRPD analysis of the thermally stressed material showed no degradation or signs of form conversion (Table 3).

Brimonidine Pamoate Polymorph Form C

Form C was observed from crystallizations of Form A in binary solvent systems, utilizing the fast cooling profile (disclosed herein above), such as: DMSO/MIBK, NMP (N-methyl-2-pyrrolidone)/acetone, NMP/MTBE (methyl-tort-butyl ether), NMP/EtOH, DMSO/IPAc (isopropyl acetate), NMP/IPA (isopropyl alcohol), and NMP/toluene. Form C was also observed from: NMP/MTBE, DMSO/EtOH, NMP/IPAc, DMSO/IPA, NMP/heptane, NMP/DCM (dichloromethane), NMP/toluene, NMP/water, NMP/THF and NMP/MeOH with a slow cooling profile. This unique solid was fully characterized as described below.

Figure 12:
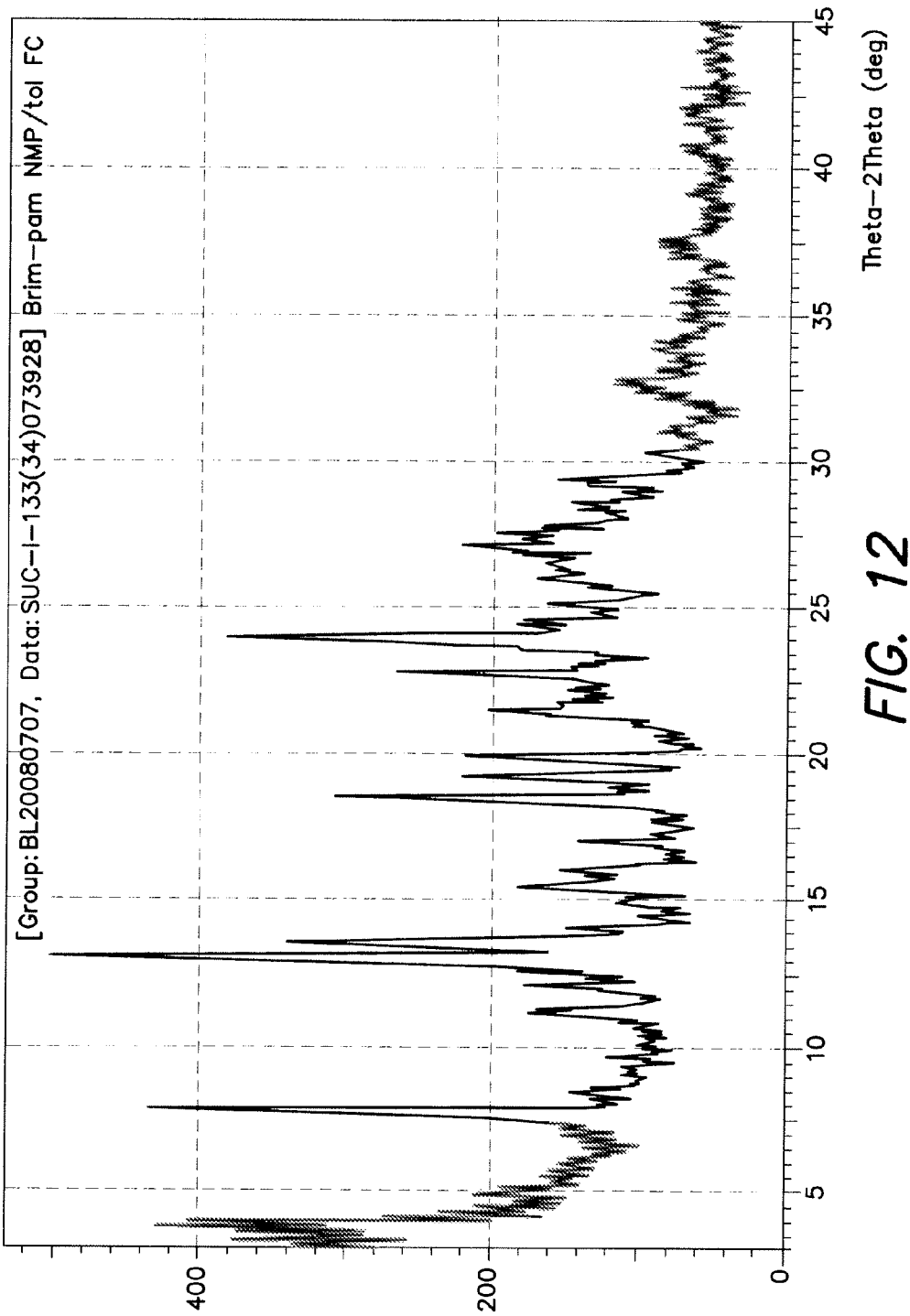
FIG. 12 shows an XRPD spectrum of brimonidine pamoate polymorph Form C.

Form C, lot SUC-I-133(34), afforded a unique crystalline XRPD pattern compared to the diffraction patterns of Forms A, B, D, E, and F. FIG. 12 shows an XRPD spectrum of Form C (lot SUC-I-133(34)).

In one aspect, the present invention provides brimonidine pamoate polymorph Form C characterized by an XRPD spectrum that comprises peaks at 2θ angles of 7.7, 12.8, 13.4, and 23.8°±0.2°.

In another aspect, the present invention provides brimonidine pamoate polymorph Form C characterized by an XRPD spectrum that comprises peaks at 2θ angles of 7.7, 12.8, 13.4, 18.4, 19.2, 19.8, 22.6, and 23.8°±0.2°.

Figure 13:
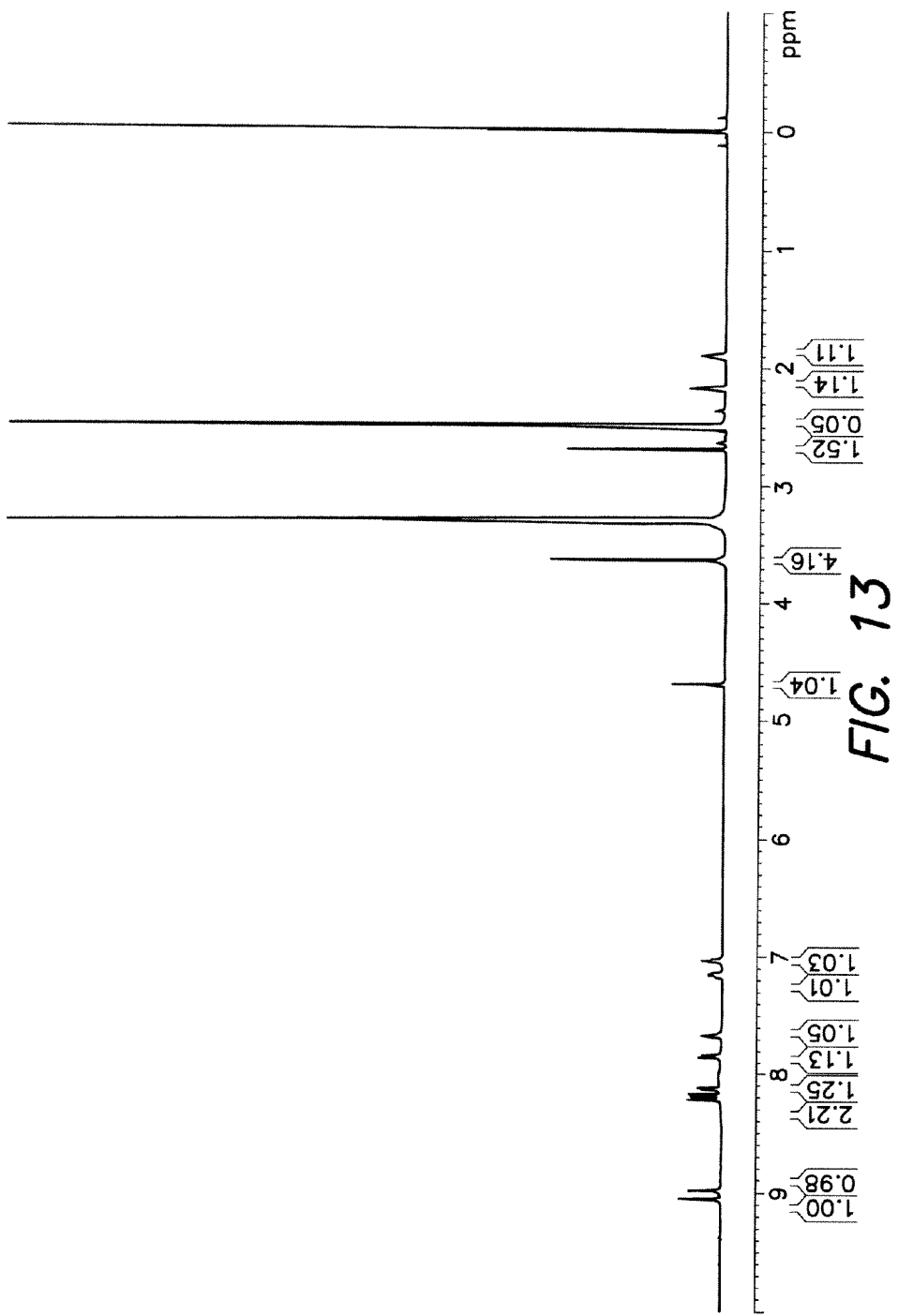
FIG. 13 shows an $^1$H NMR spectrum of brimonidine pamoate polymorph Form C.

$^1$H NMR analysis of this material showed approximately 9.9 wt % residual NMP and a 0.5:1 pamoate to brimonidine ratio confirming the formation of a hemi-pamoate salt of brimonidine. FIG. 13 shows an NMR spectrum for brimonidine pamoate polymorph Form C (lot SUC-I-133(34)).

Figure 14:
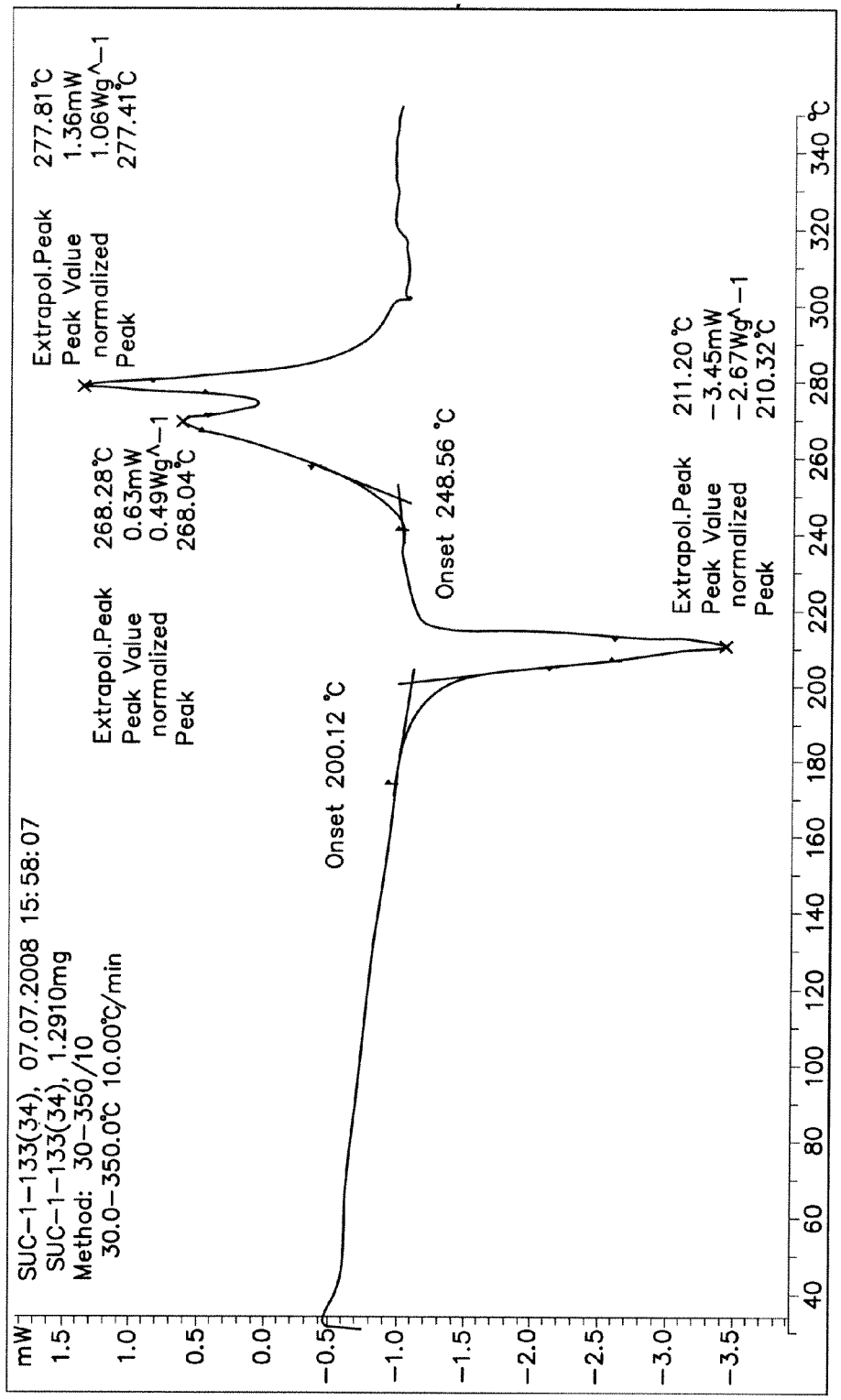
FIG. 14 shows a DSC curve of brimonidine pamoate polymorph Form C.
Figure 15:
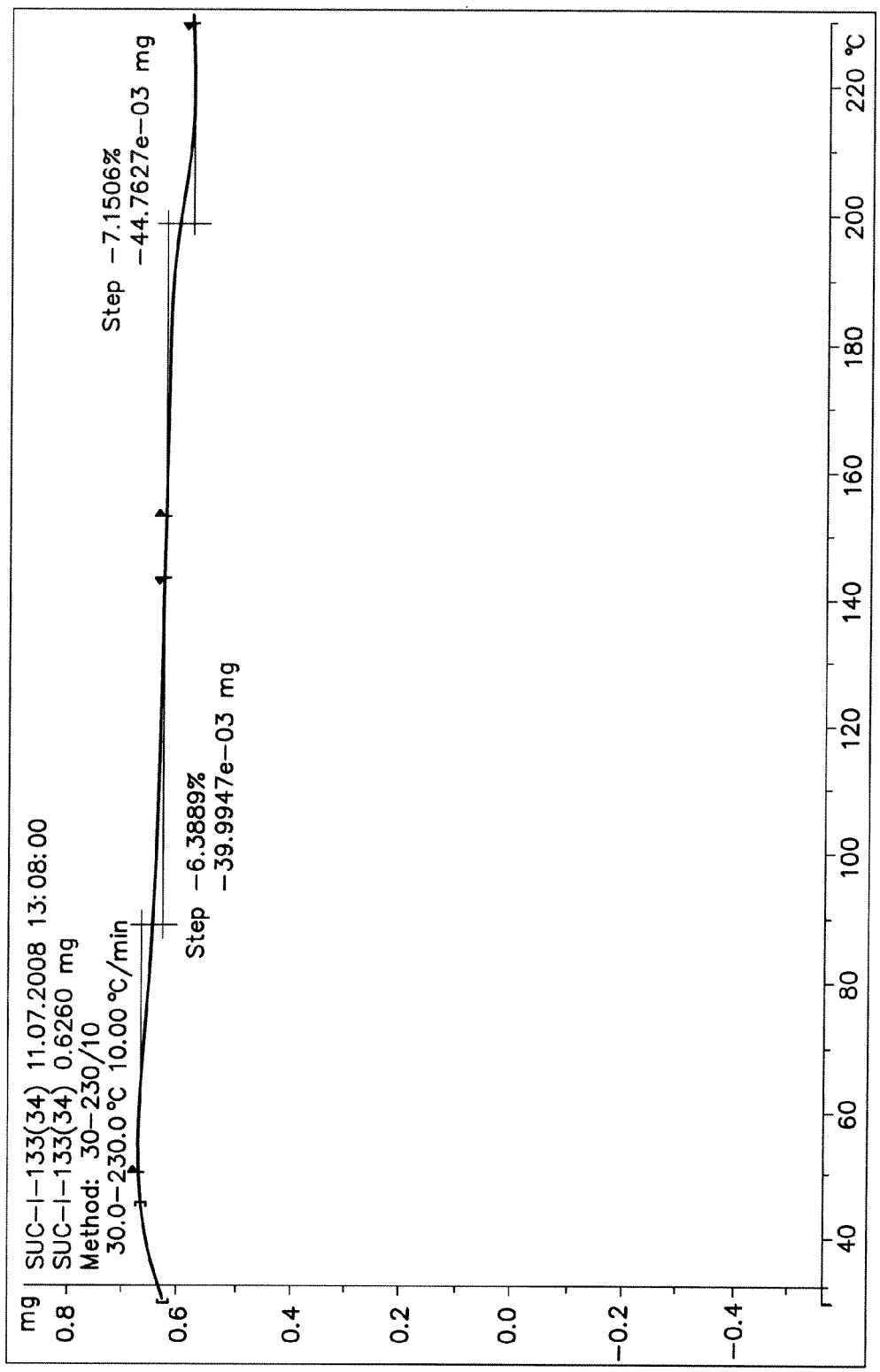
FIG. 15 shows a TGA curve of brimonidine pamoate polymorph Form C.

Thermal analysis of Form C showed a single DSC endothermic event at 210° C. (see FIG. 14) attributed to melting of the crystalline salt. Further analysis by TGA showed weight loss of 6.4% between 50 and 140° C. (see FIG. 15) likely due to the loss of water and approximately 7.2 wt % from 180-230° C. (see FIG. 15) attributed to the loss of NMP.

Figure 16:
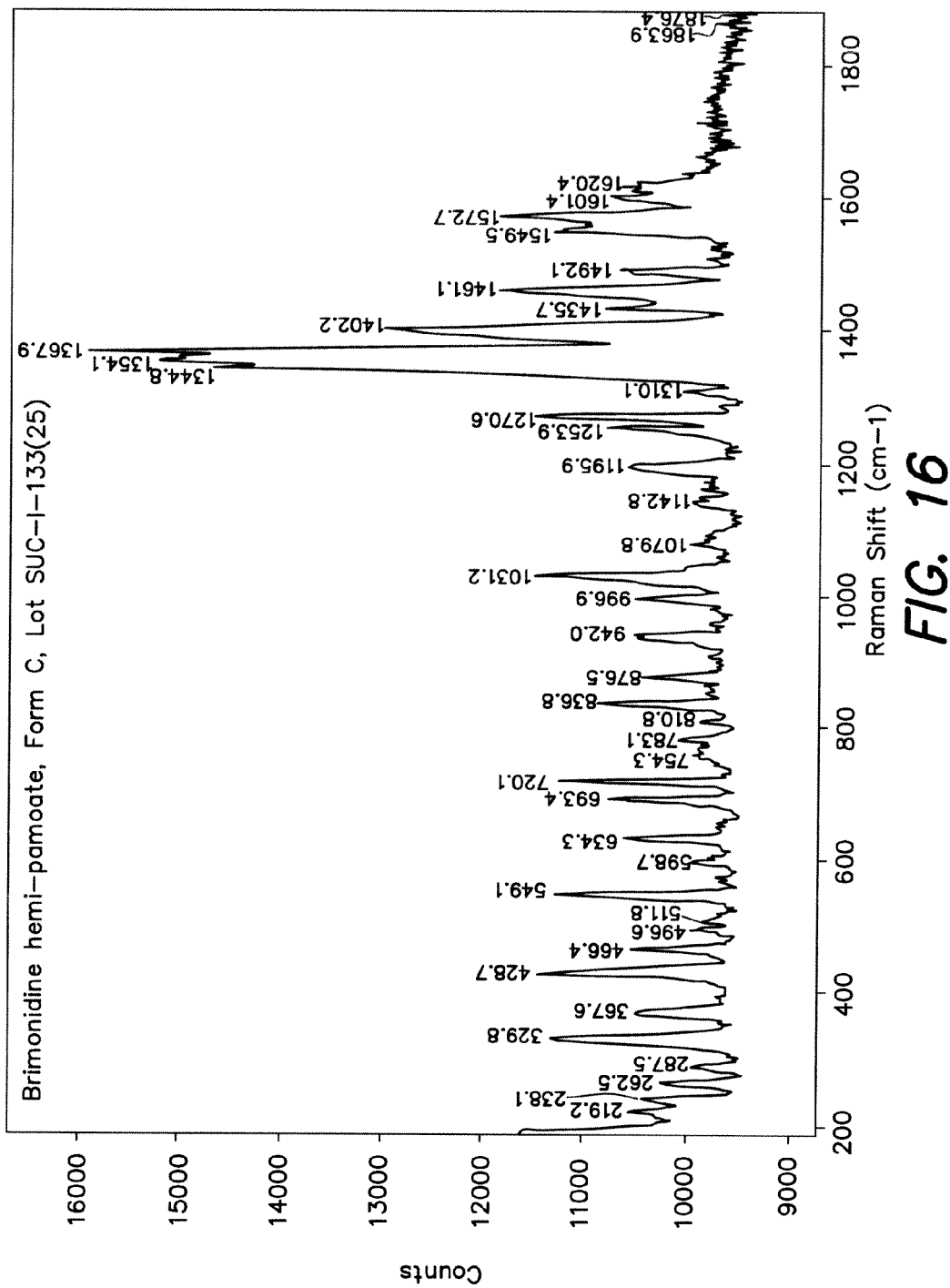
FIG. 16 shows a Raman spectroscopy spectrum of brimonidine pamoate polymorph Form C.

FIG. 16 shows a Raman spectroscopy spectrum of Form C (lot SUC-I-133(25)).

In one aspect, the present invention provides brimonidine pamoate polymorph Form C characterized by a Raman spectroscopy spectrum that comprises peaks at 161.5, 1344.8, 1354.1, 1367.9, and 1402.2 cm$^{-1}$.

In another aspect, the present invention provides brimonidine pamoate polymorph Form C characterized by a Raman spectroscopy spectrum that comprises peaks at 135.8, 161.5, 428.7, 720.1, 1031.2, 1270.6, 1344.8, 1354.1, 1367.9, 1402.2, 1461.1, 1549.5, and 1572.7 cm$^{-1}$.

Raman spectroscopy analysis of Form C showed minor spectral differences in comparison to the Raman spectra of Forms A, D, and E, but significant differences in comparison to the spectra of Forms B and F in the range of about 1300-1425 cm$^{-1}$.

Moisture sorption analysis of lot SUC-I-134(37) showed the hemi-pamoate to be moderately hygroscopic, adsorbing 4.6 wt % water at 60% RH and 13.0 wt % water at 90% RH. Upon desorption, no hysteresis or indication of hydrate formation was observed. XRPD analysis of the solids following the experiment afforded a diffraction pattern which was consistent with Form C, indicating no form conversion had occurred during the analysis.

A competitive slurry of Forms A, B, C and D in THF revealed that along with the other starting forms, Form C will also convert to the most stable anhydrate form (Form E) (see FIG. 6). Slurries comprising Forms A, C, D and E in water showed conversion to Form F after one week of equilibration (Table 2). These findings indicate that Form F is more stable in water than Forms A, C, D and E. Form C was also observed to convert to a mixture of Forms B and F by XRPD after an overnight slurry in water at ambient conditions. As a result, the aqueous solubility of Form C was not determined.

Form C was observed to be stable after one week of storage at 60° C. HPLC and XRPD analysis of the thermally stressed material showed no significant degradation or signs of form conversion (Table 3). After two weeks of storage at elevated relative humidity (88% RH), Form C was confirmed to be stable by XRPD and showed no indication of deliquescence (Table 4).

Brimonidine Pamoate Form D

Form D was observed from crystallizations of Form A in the following binary solvent systems, using fast-cooling profiles: NMP/MeCN (acetonitrile), DMSO/EtOH and DMSO/toluene. Form D was also isolated from slow-cooling crystallizations such as: NMP/MeCN and NMP/IPA. Form D was fully characterized as described below.

Figure 17:
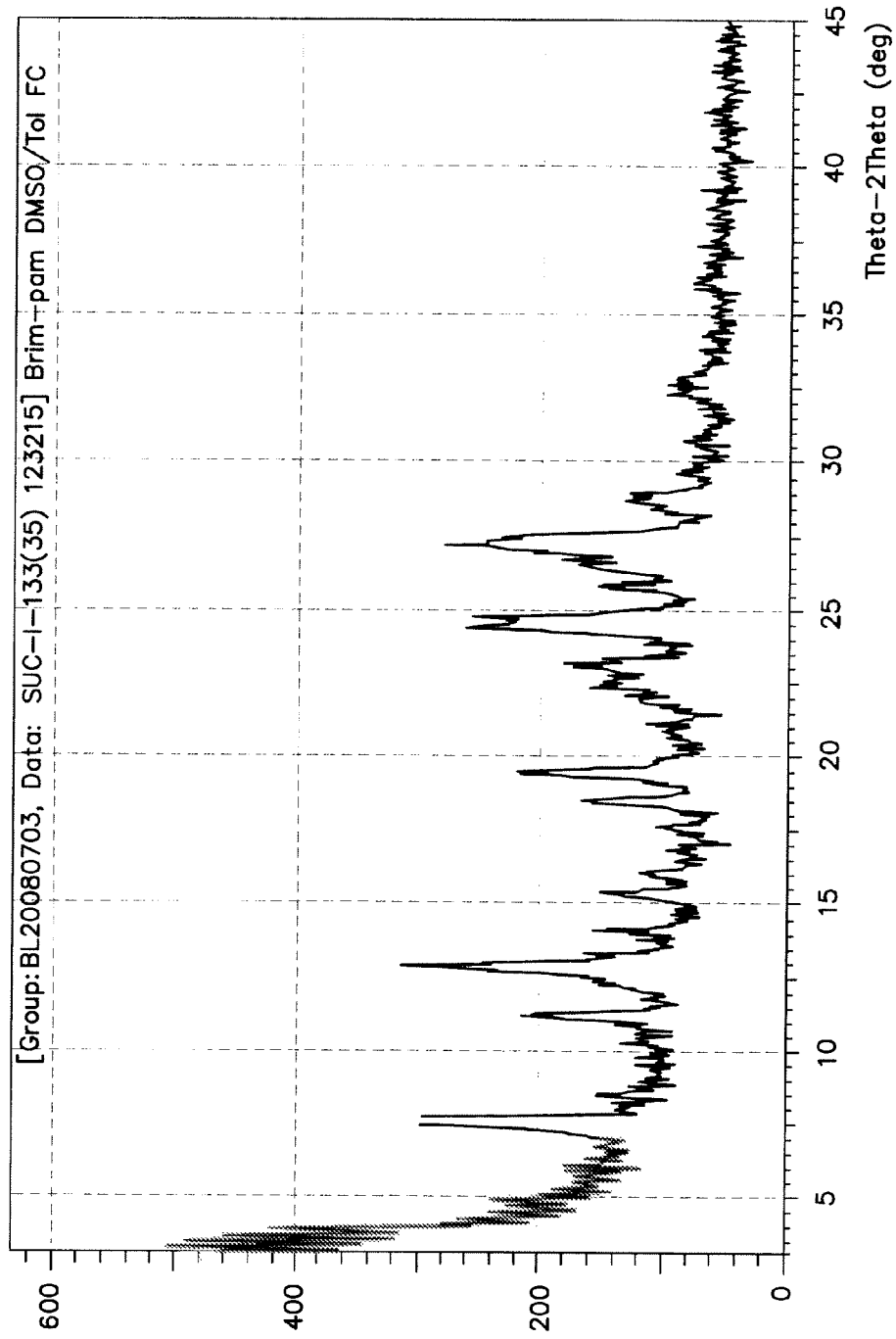
FIG. 17 shows an XRPD spectrum of brimonidine pamoate polymorph Form D.

Lots SUC-I-133(35) and SUC-I-133(7) obtained from a fast-cooling crystallizations of Form A in DMSO/toluene and NMP/MeCN, afforded a unique crystalline XRPD pattern compared to the diffraction patterns of Forms A, B, C, E and F. FIG. 17 shows an XRPD spectrum of Form D (lot SUC-I-133(35)).

In one aspect, the present invention provides brimonidine pamoate polymorph Form D characterized by an XRPD spectrum that comprises peaks at 2θ angles of 7.5, 12.8, 24.5, and 27.1°±0.2°.

In another aspect, the present invention provides brimonidine pamoate polymorph Form D characterized by an XRPD spectrum that comprises peaks at 2θ angles of 7.5, 11.1, 12.8, 18.4, 19.4, 22.5, 23.1, 24.5, 16.4, and 27.1°±0.2°.

Figure 18:
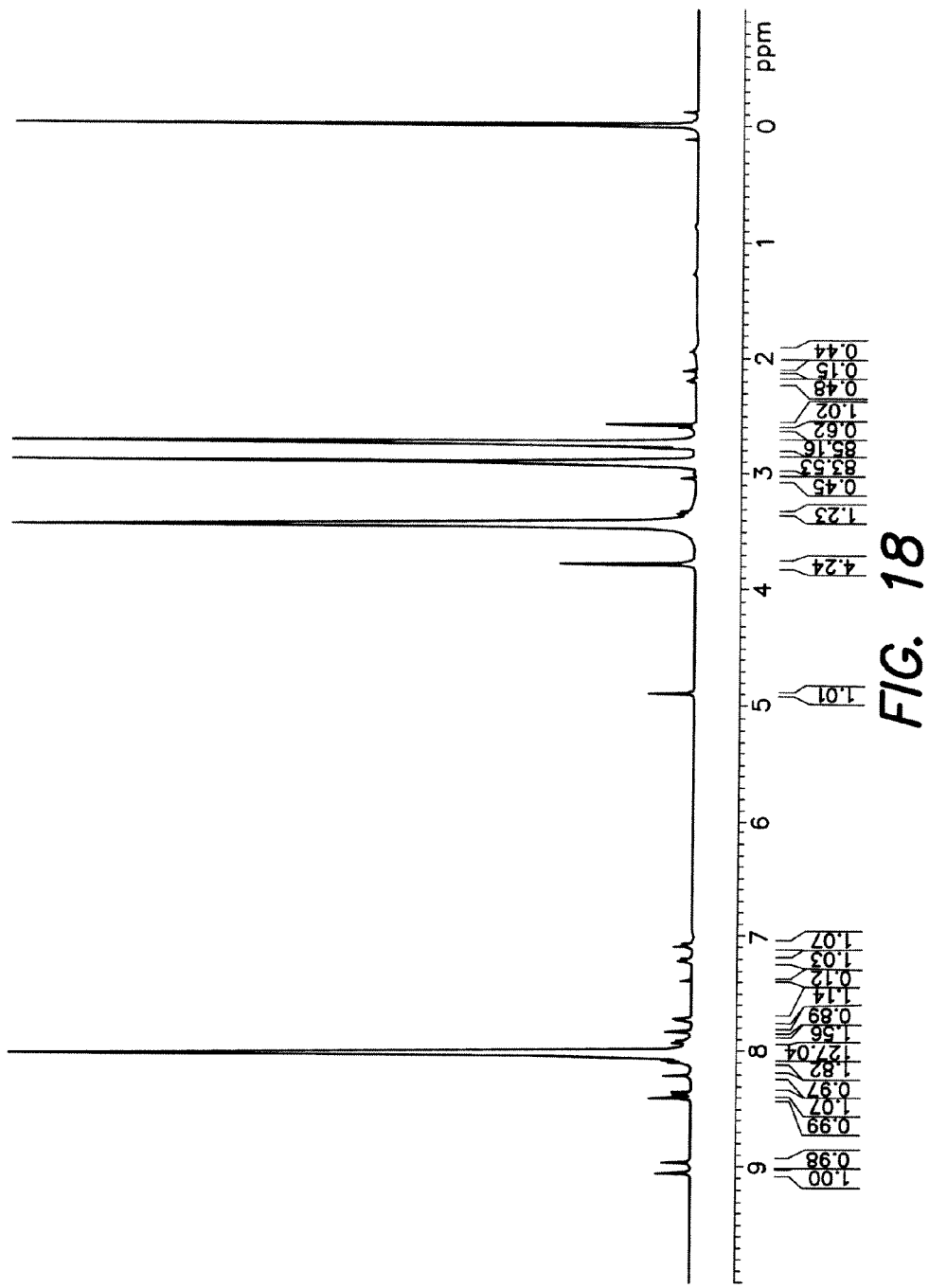
FIG. 18 shows an $^1$H NMR spectrum of brimonidine pamoate polymorph Form D.

$^1$H NMR analysis of Form D, lot SUC-I-133(35), showed a 0.5:1 pamoate to brimonidine ratio confirming the formation of a hemi-pamoate salt of brimonidine. FIG. 18 shows an NMR spectrum for brimonidine pamoate polymorph Form D (lot SUC-I-133 (35)).

Figure 19:
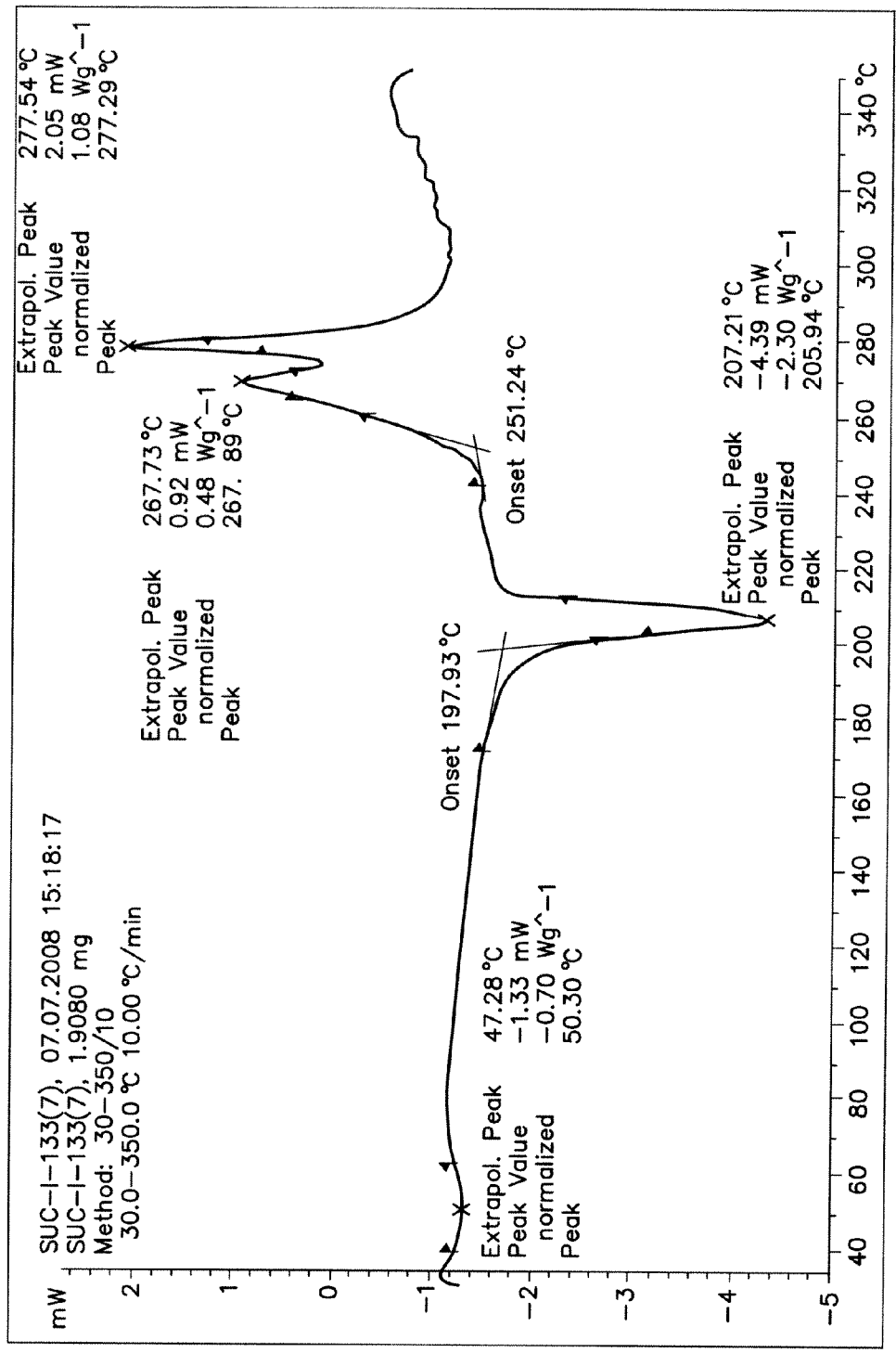
FIG. 19 shows a DSC curve of brimonidine pamoate polymorph Form D.
Figure 20:
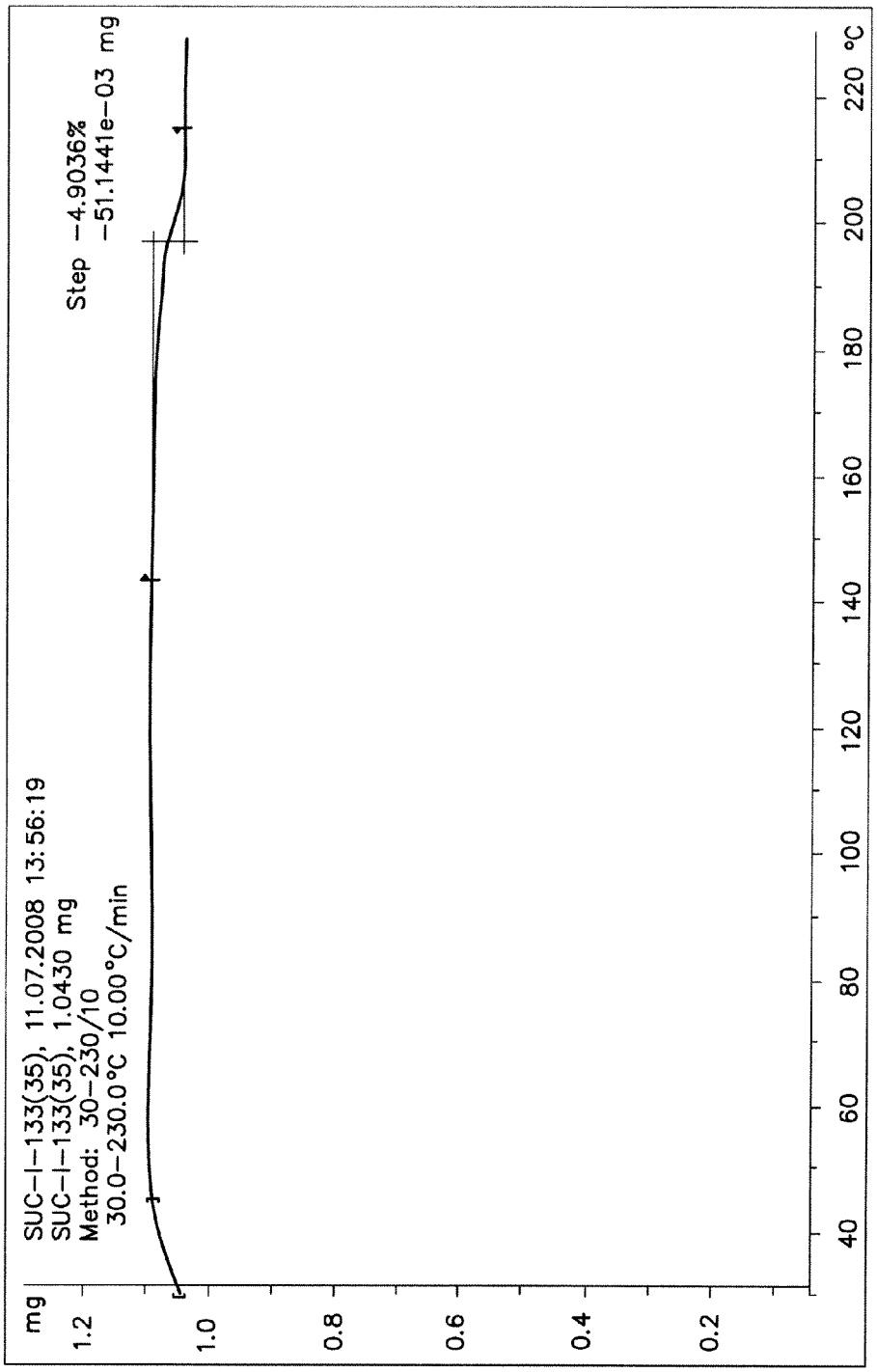
FIG. 20 shows a TGA curve of brimonidine pamoate polymorph Form D.

Thermal analysis of Form D, lot SUC-I-133(7), by DSC showed endothermic events at 50 and 206° C. (see FIG. 19) attributed to a loss of residual solvent and melting of the crystalline salt. Further analysis of lot SUC-I-133(35) by TGA showed no weight loss below 160° C. (see FIG. 20).

Figure 21:
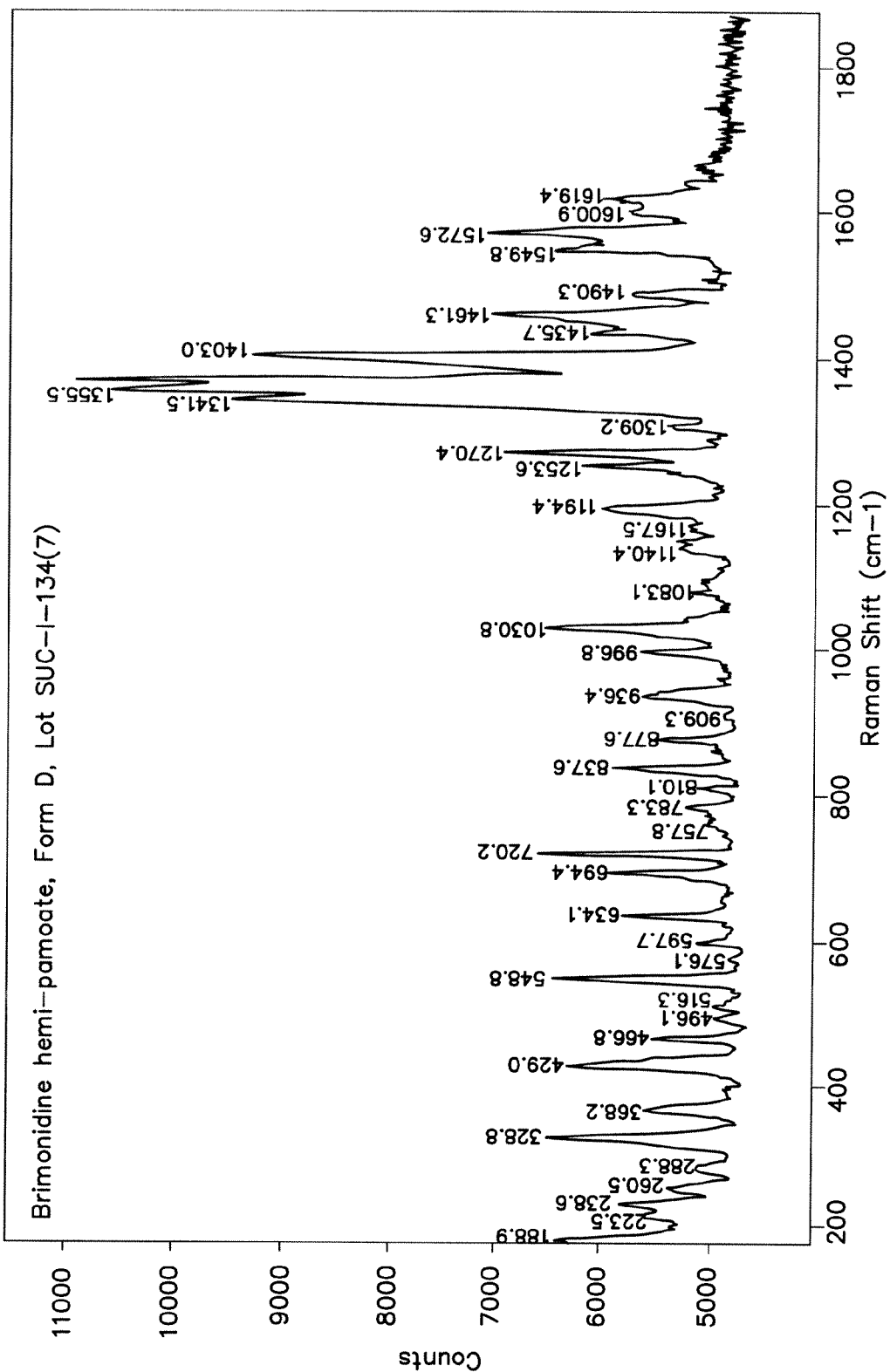
FIG. 21 shows a Raman spectroscopy spectrum of brimonidine pamoate polymorph Form D.

FIG. 21 shows a Raman spectroscopy spectrum of Form D (lot SUC-I-134(7)).

In one aspect, the present invention provides brimonidine pamoate polymorph Form D characterized by a Raman spectroscopy spectrum that comprises peaks at 157.4, 1270.4, 1341.5, 1355.5, and 1403.0 cm$^{-1}$.

In another aspect, the present invention provides brimonidine pamoate polymorph Form D characterized by a Raman spectroscopy spectrum that comprises peaks at 135.7, 146.8, 157.4, 188.9, 328.8, 429.0, 548.8, 720.2, 1030.8, 1253.6, 1270.4, 1341.5, 1355.5, 1403.0, 1461.3, 1549.8, and 1572.6 cm$^{-1}$.

Raman spectroscopy analysis of Form D showed minor spectral differences in comparison to the Raman spectra of Form A, C, and E, but significant differences in comparison to the spectra of Forms B and F in the range of about 1300-1425 cm$^{-1}$.

Moisture sorption analysis of lot SUC-I-133(7) showed Form D to be slightly hygroscopic, adsorbing 1.8% water at 60% RH and 2.6 wt % water at 90% RH. Upon desorption no hysteresis or indication of hydrate formation was observed. XRPD analysis of the solids following moisture sorption analysis afforded a diffraction pattern which was consistent with Form D, indicating no form conversion had occurred during the experiment.

A competitive slurry of Forms A, B, C and D in THF revealed that along with the other starting forms, Form D will also convert to the most stable anhydrate form (Form E) (see FIG. 6). Slurries comprising Forms A, C, D and E in water showed conversion to Form F after one week of equilibration (Table 2). These findings indicate that Form F is more stable in water than Forms A, C, D and E. Form D was also observed to convert to a mixture of Forms B and F by XRPD after an overnight slurry in water at ambient conditions. As a result, the aqueous solubility of Form D was not determined.

Form D was observed to be stable after one week of storage at 60° C. HPLC and XRPD analysis of the thermally stressed material showed no significant degradation or signs of form conversion (Table 3).

Brimonidine Pamoate Polymorph Form E

Form E was observed from a one week of slurry of Form A in THF, and later obtained from larger scale slurry of Form A after 18 days.

Figure 22:
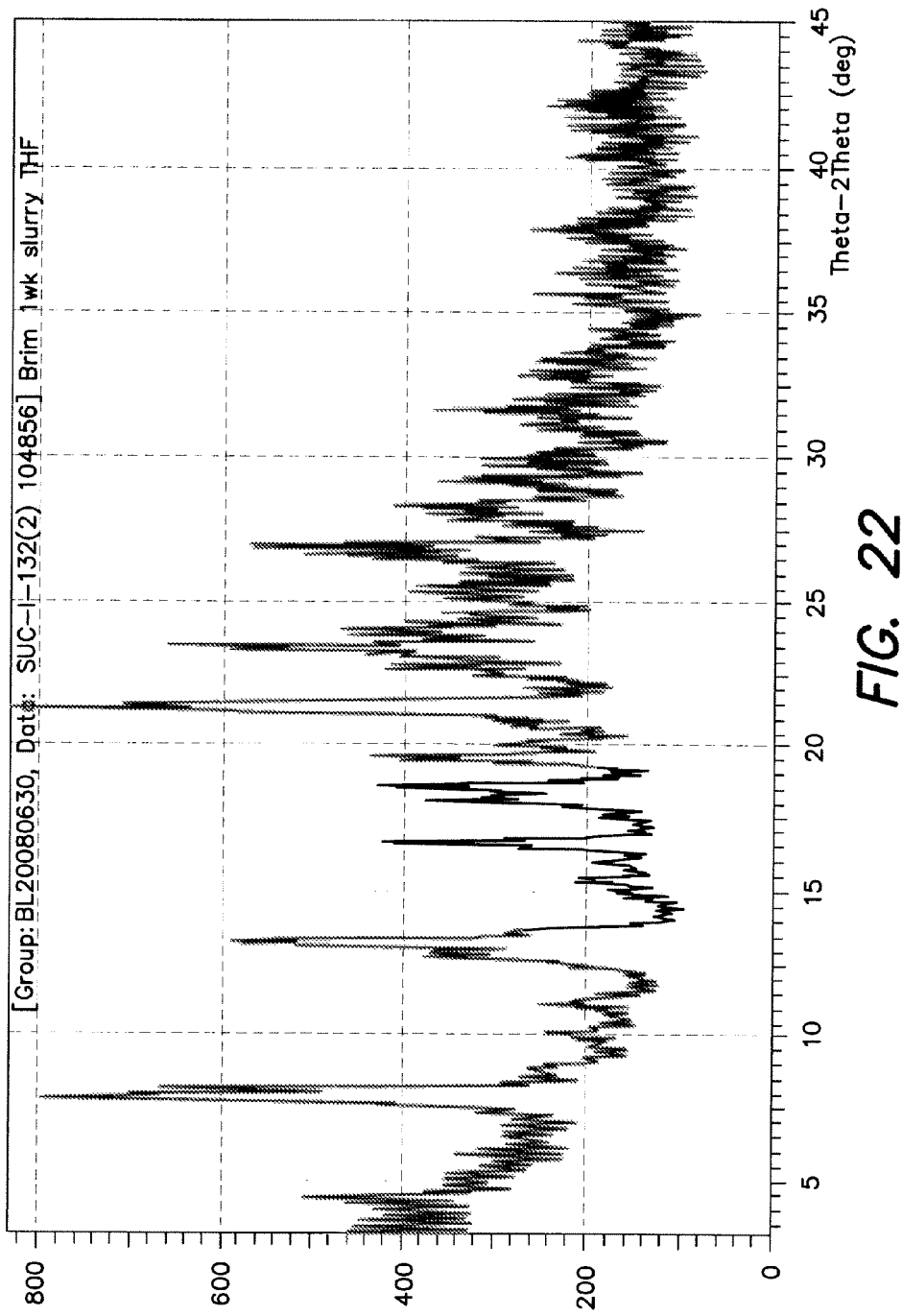
FIG. 22 shows an XRPD spectrum of brimonidine pamoate polymorph Form E.

Form E, lot SUC-I-132(2), afforded a unique crystalline XRPD pattern compared to the diffraction patterns of Forms A, B, C, D and F. FIG. 22 shows an XRPD spectrum of Form E (lot SUC-I-132(2)).

In one aspect, the present invention provides brimonidine pamoate polymorph Form E characterized by an XRPD spectrum that comprises peaks at 2θ angles of 7.7, 8.0, 13.1, and 21.2°±0.2°.

In another aspect, the present invention provides brimonidine pamoate polymorph Form E characterized by an XRPD spectrum that comprises peaks at 2θ angles of 7.7, 8.0, 13.1, and 21.2°±0.2°.

Figure 23:
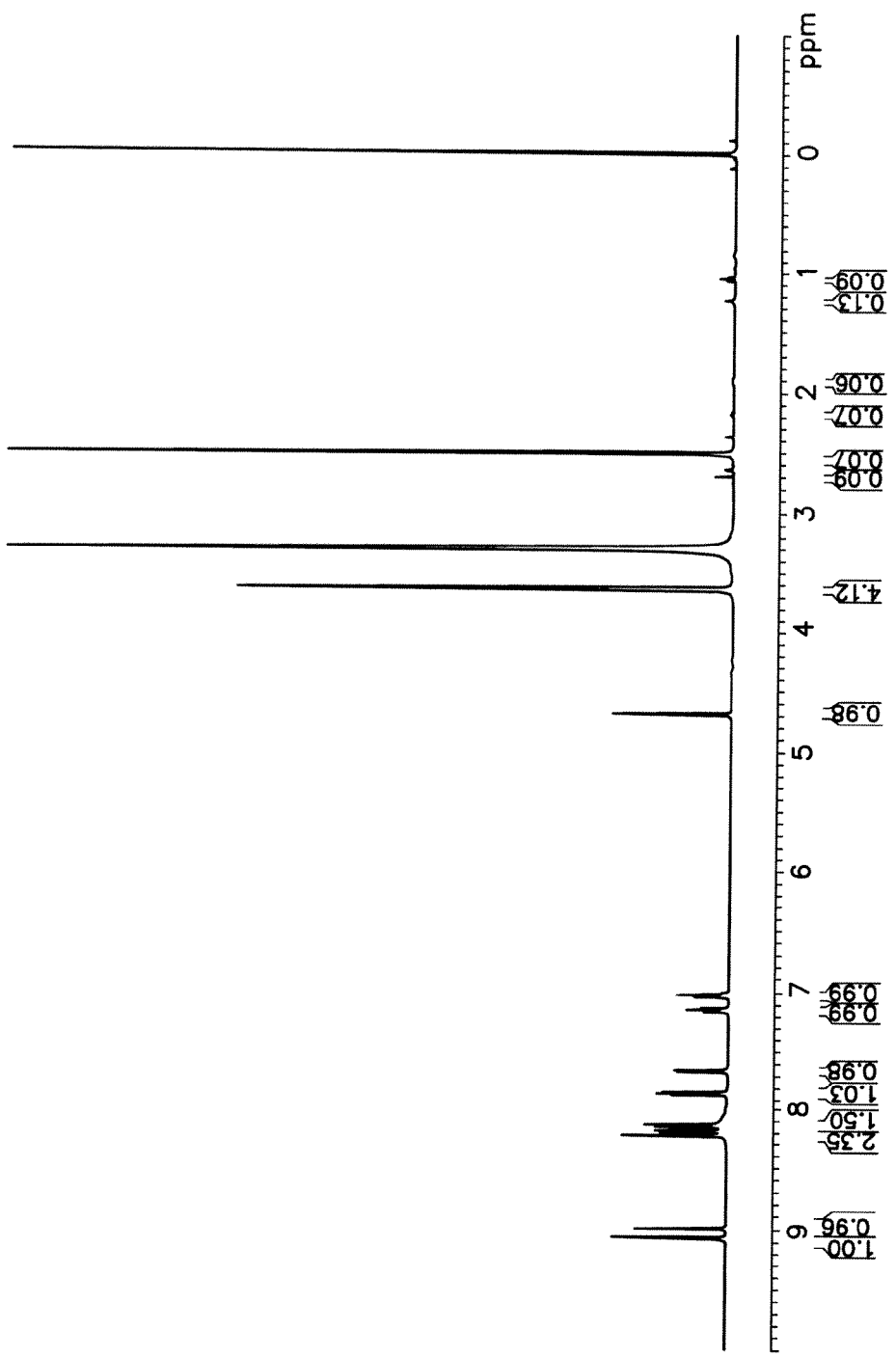
FIG. 23 shows an $^1$H NMR spectrum of brimonidine pamoate polymorph Form E.

$^1$H NMR analysis showed a 0.5:1 pamoate to brimonidine ratio confirming the formation of a hemi-pamoate salt of brimonidine which contained approximately 0.2 wt % and 0.3 wt % residual THF and EtOH respectively. FIG. 23 shows an NMR spectrum for brimonidine pamoate polymorph Form E (lot SUC-I-132(2)).

Figure 24:
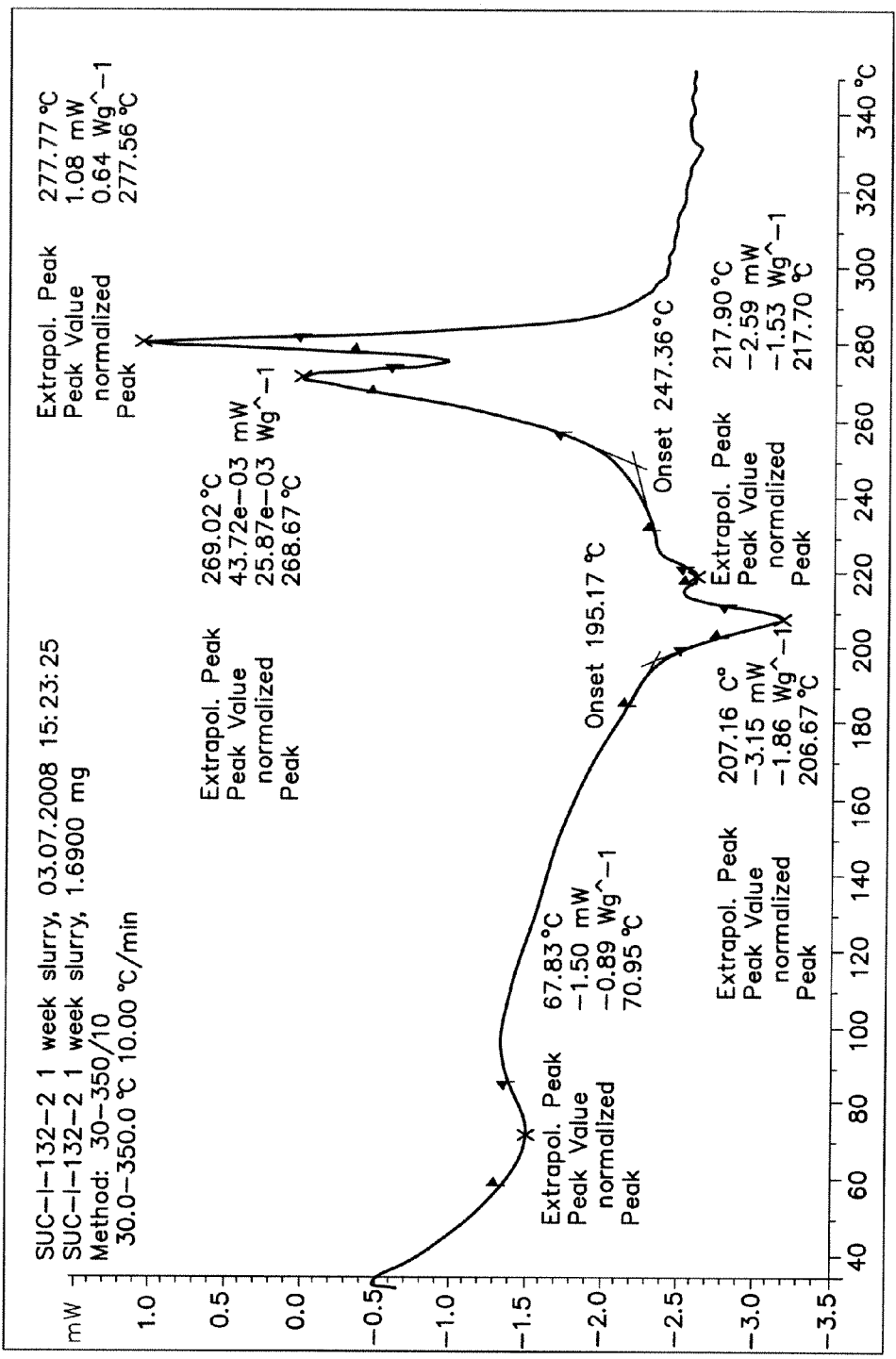
FIG. 24 shows a DSC curve of brimonidine pamoate polymorph Form E.
Figure 25:
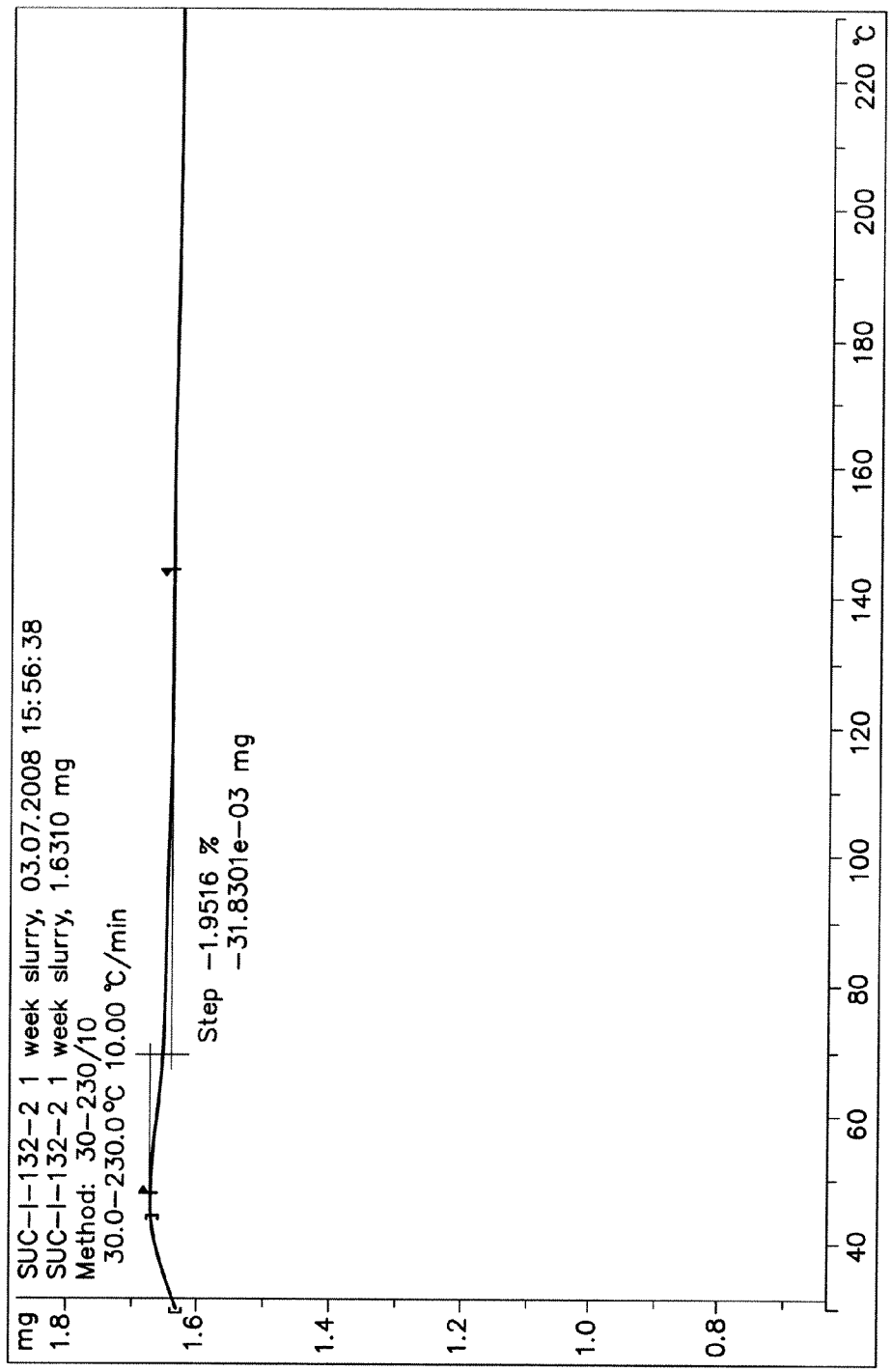
FIG. 25 shows a TGA curve of brimonidine pamoate polymorph Form E.

Thermal analysis of Form E showed DSC endothermic events around 71° C. attributed to loss of residual solvent and at 207° C. (see FIG. 24) due to melting of the crystalline salt. Further analysis by TGA showed a 3.7% weight loss between 50 and 150° C. (see FIG. 25) likely attributed to loss of residual THF, EtOH and water.

Figure 26:
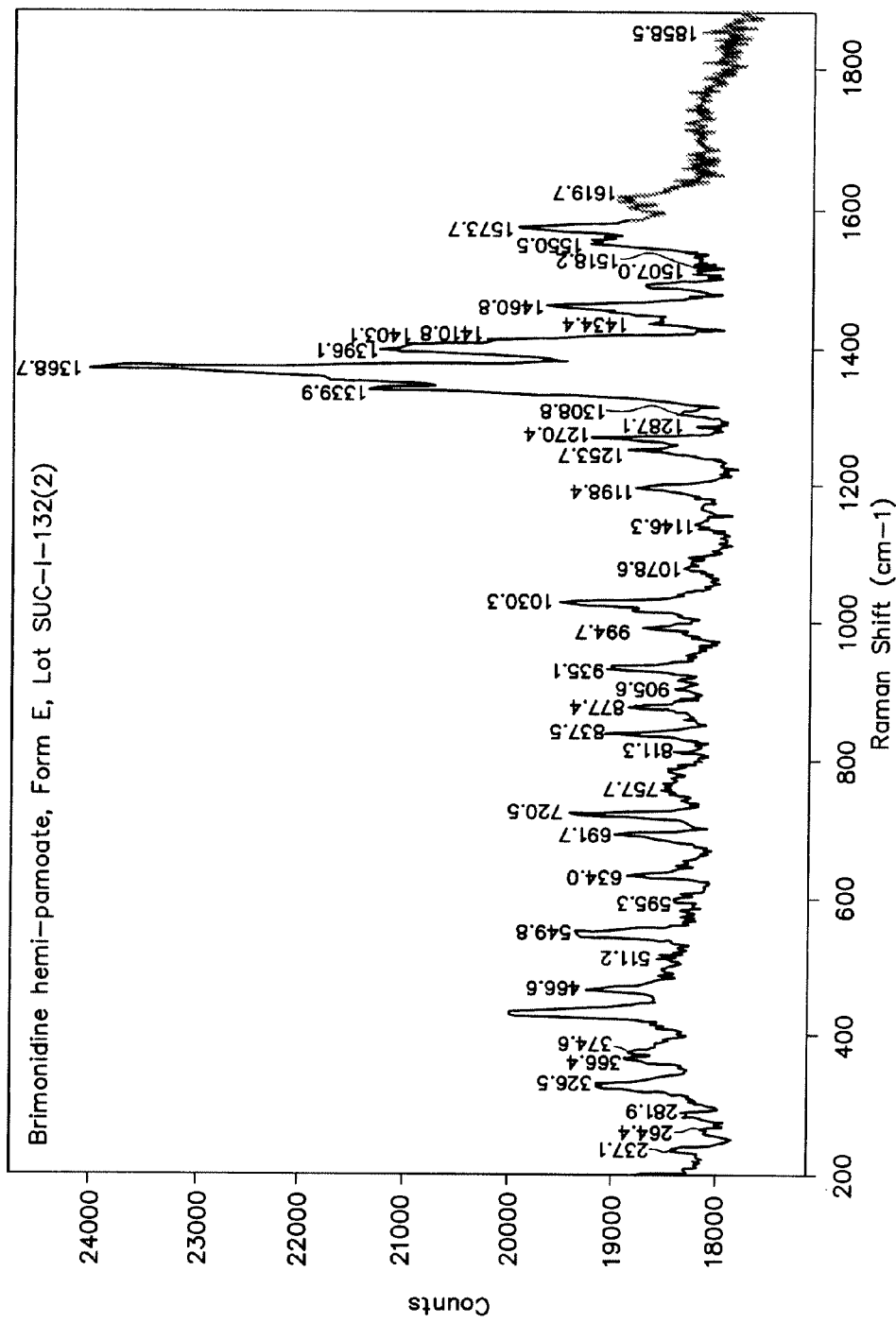
FIG. 26 shows a Raman spectroscopy spectrum of brimonidine pamoate polymorph Form E.

FIG. 26 shows a Raman spectroscopy spectrum of Form E (lot SUC-I-132(2)).

In one aspect, the present invention provides brimonidine pamoate polymorph Form E characterized by a Raman spectroscopy spectrum that comprises peaks at 1339.9, 1368.7, 1396.1, 1403.1, and 1410.8 cm$^{-1}$.

In another aspect, the present invention provides brimonidine pamoate polymorph Form E characterized by a Raman spectroscopy spectrum that comprises peaks at 326.5, 466.6, 549.8, 720.5, 1030.3, 1270.4, 1339.9, 1368.7, 1396.1, 1403.1, 1410.8, 1460.8, and 1573.7 cm$^{-1}$.

Raman spectroscopy analysis of Form E showed minor spectral differences in comparison to the Raman spectra of Forms A, C, and D, but significant differences in comparison to the spectra of Forms B and F in the range of about 1300-1425 cm$^{-1}$.

Moisture sorption analysis of lot SUC-I-138(2) showed Form E to be slightly hygroscopic adsorbing 3.1 wt % water at 60% RH and 4.2 wt % water at 90% RH. Upon desorption, no hysteresis or indication of hydrate formation was observed. XRPD analysis of the solids following moisture sorption analysis afforded a diffraction pattern which was consistent with Form E, indicating no form conversion had occurred during the experiment.

A competitive slurry of Forms A, B, C and D in THF revealed that each form converted to the anhydrate Form E. These findings suggest that Form E is the most stable anhydrate form. A slurry comprising Forms A, C, D and E in water showed conversion to Form F after one week of equilibration (Table 2). These findings indicate that Form F is more stable in water than Forms A, C, D and E. Form E was observed to convert to a mixture of Forms B and F by XRPD after overnight slurry in water at ambient conditions. As a result, the aqueous solubility of Form E was not determined.

Form E was observed to be stable after one week of storage at 60° C. HPLC and XRPD analysis of the thermally stressed material showed no significant degradation or signs of form conversion (Table 3).

Brimonidine Pamoate Polymorph Form F

Form F was observed from the following binary solvent crystallizations which utilized fast cooling profiles: NMP/water and DMSO/water. This unique solid form was characterized as described below.

Figure 27:
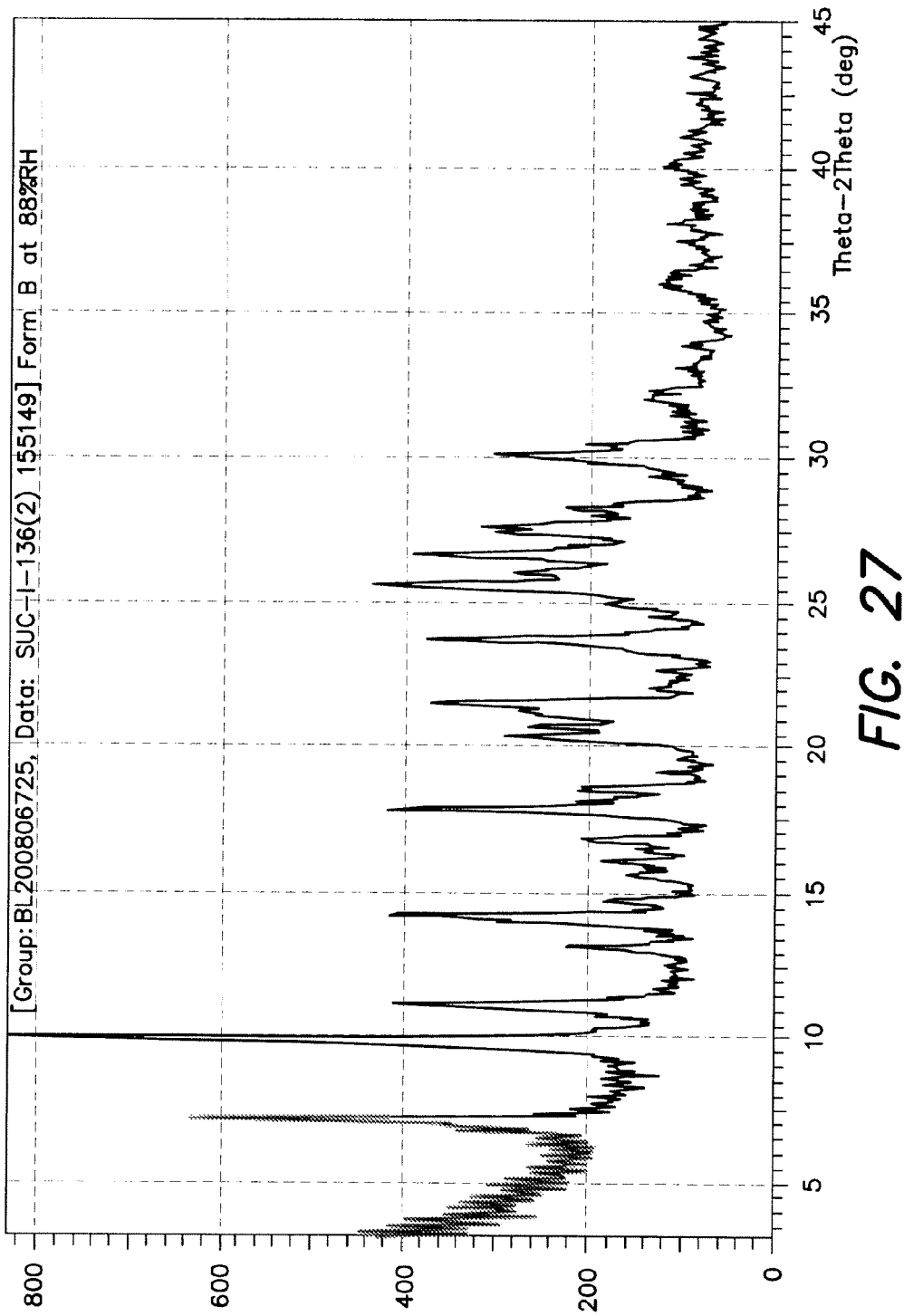
FIG. 27 shows an XRPD spectrum of brimonidine pamoate polymorph Form F.

Lots SUC-I-133(37) and SUC-I-133(38) obtained from crystallizations of Form A in NMP/water and DMSO/water solvent systems, using fast-cooling profile (as described herein above), afforded a unique crystalline XRPD pattern compared to the diffraction patterns of Forms A, C, D, and E. The diffraction pattern of Form F showed some similarities to that of the Form B sesqui-hydrate. FIG. 27 shows an XRPD spectrum of Form F (lot SUC-I-136(2)).

In one aspect, the present invention provides brimonidine pamoate polymorph Form F characterized by an X-ray powder diffraction ("XRPD") spectrum that comprises peaks at 2θ angles of 7.1, 9.8, 17.8, and 25.5°±0.2°.

In another aspect, the present invention provides brimonidine pamoate polymorph Form F characterized by an X-ray powder diffraction ("XRPD") spectrum that comprises peaks at 2θ angles of 7.1, 9.8, 11.0, 14.1, 17.8, 21.4, 23.7, 25.5, 26.6, 27.6, and 30.0°±0.2°.

A slurry comprising Forms A, C, D, and E in water showed conversion to Form F after one week of equilibration (see FIG. 6). These findings indicate that Form F is more stable in water than Forms A. C. D, and E. A water slurry of Form F left overnight showed the presence of a mixture of Forms B and F. Thus, Form B is the more stable form in water. This was confirmed in subsequent repeated experiments.

Figure 28:
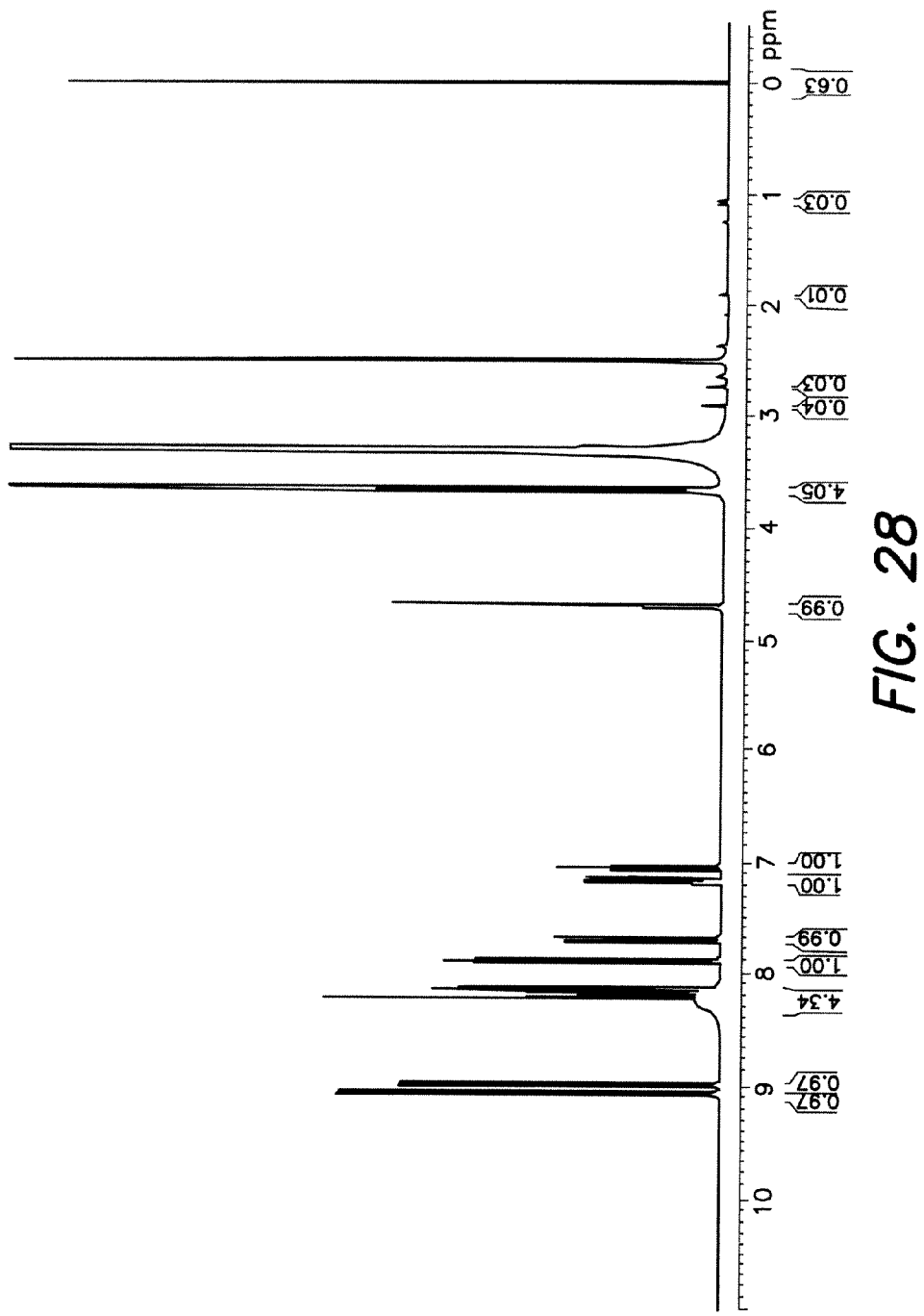
FIG. 28 shows an $^1$H NMR spectrum of brimonidine pamoate polymorph Form F.

$^1$H NMR analysis showed a 0.5:1 pamoate to brimonidine ratio, confirming the formation of a hemi-pamoate salt of brimonidine and approximately 0.3 wt % residual DMF. FIG. 28 shows an NMR spectrum for brimonidine pamoate polymorph Form F (lot SUC-I-183(1)).

Figure 29:
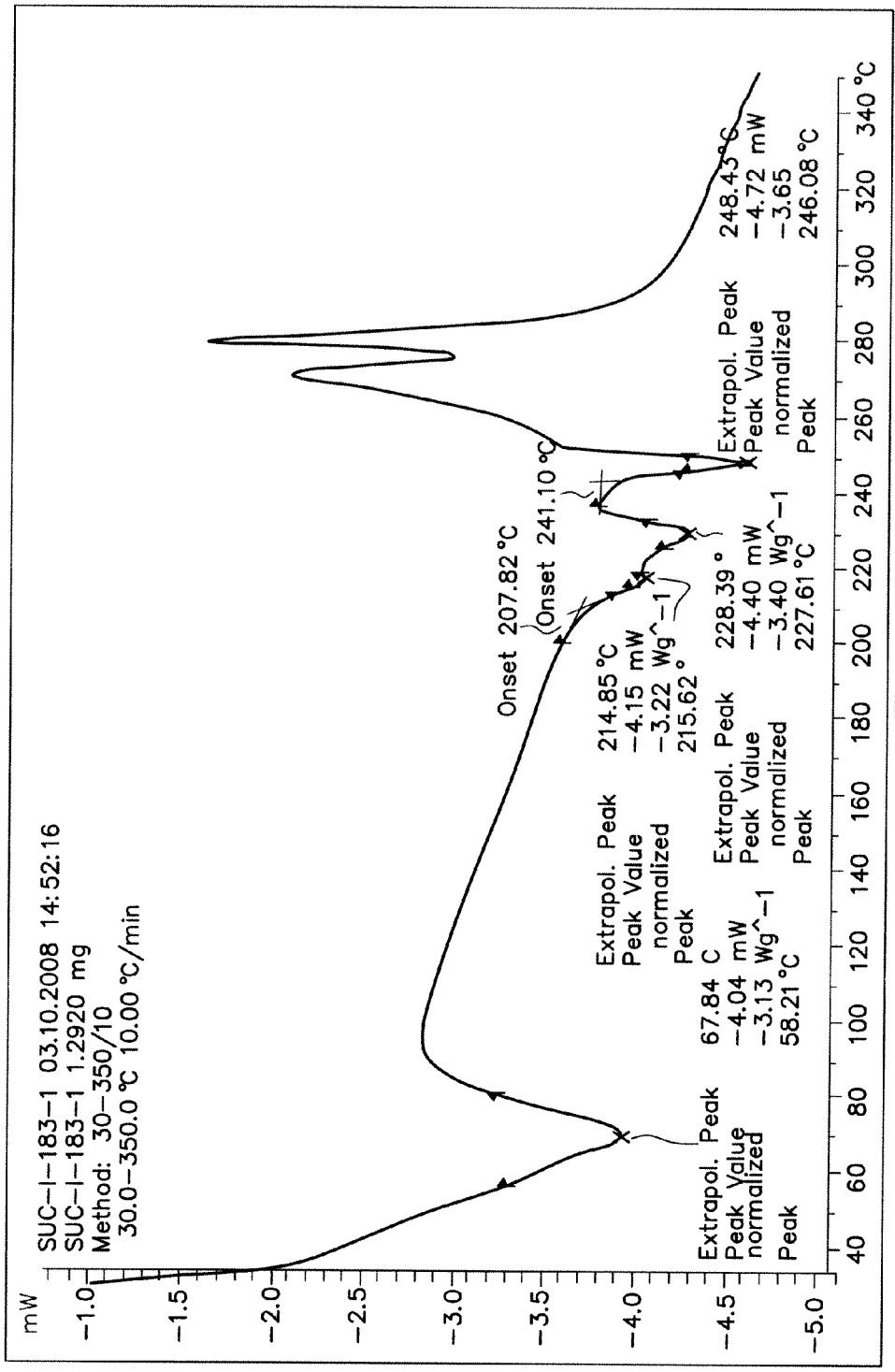
FIG. 29 shows a DSC curve of brimonidine pamoate polymorph Form F.
Figure 30:
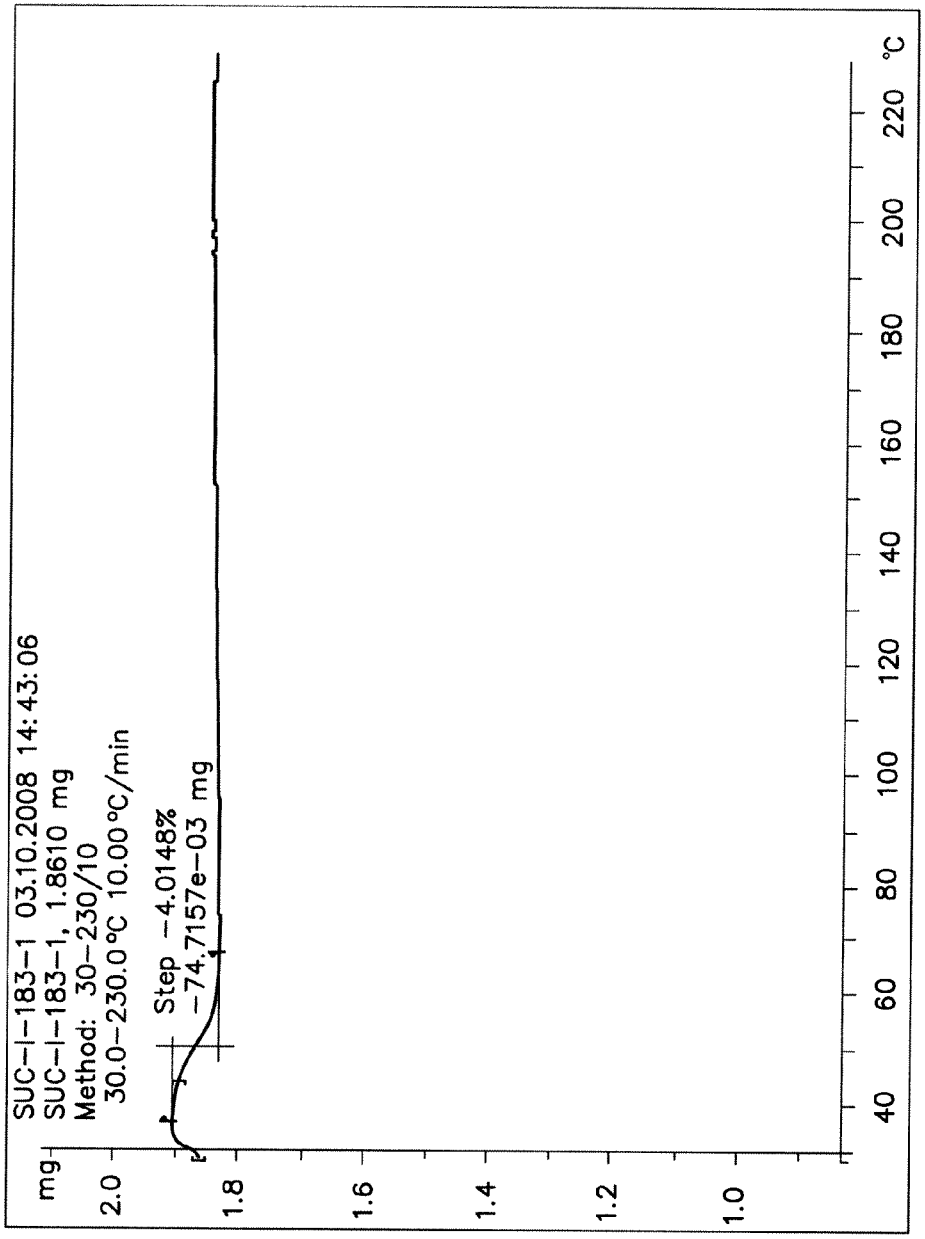
FIG. 30 shows a TGA curve of brimonidine pamoate polymorph Form F.

Thermal analysis by DSC showed multiple endothermic events at 68, 216, 228 and 246° C. (see FIG. 29) attributed to loss of water and/or DMF and melting of the crystalline salt. Further analysis of Form F by KF showed approximately 6.2 wt % water and 4.0 wt % loss by TGA (see FIG. 30).

Figure 31:
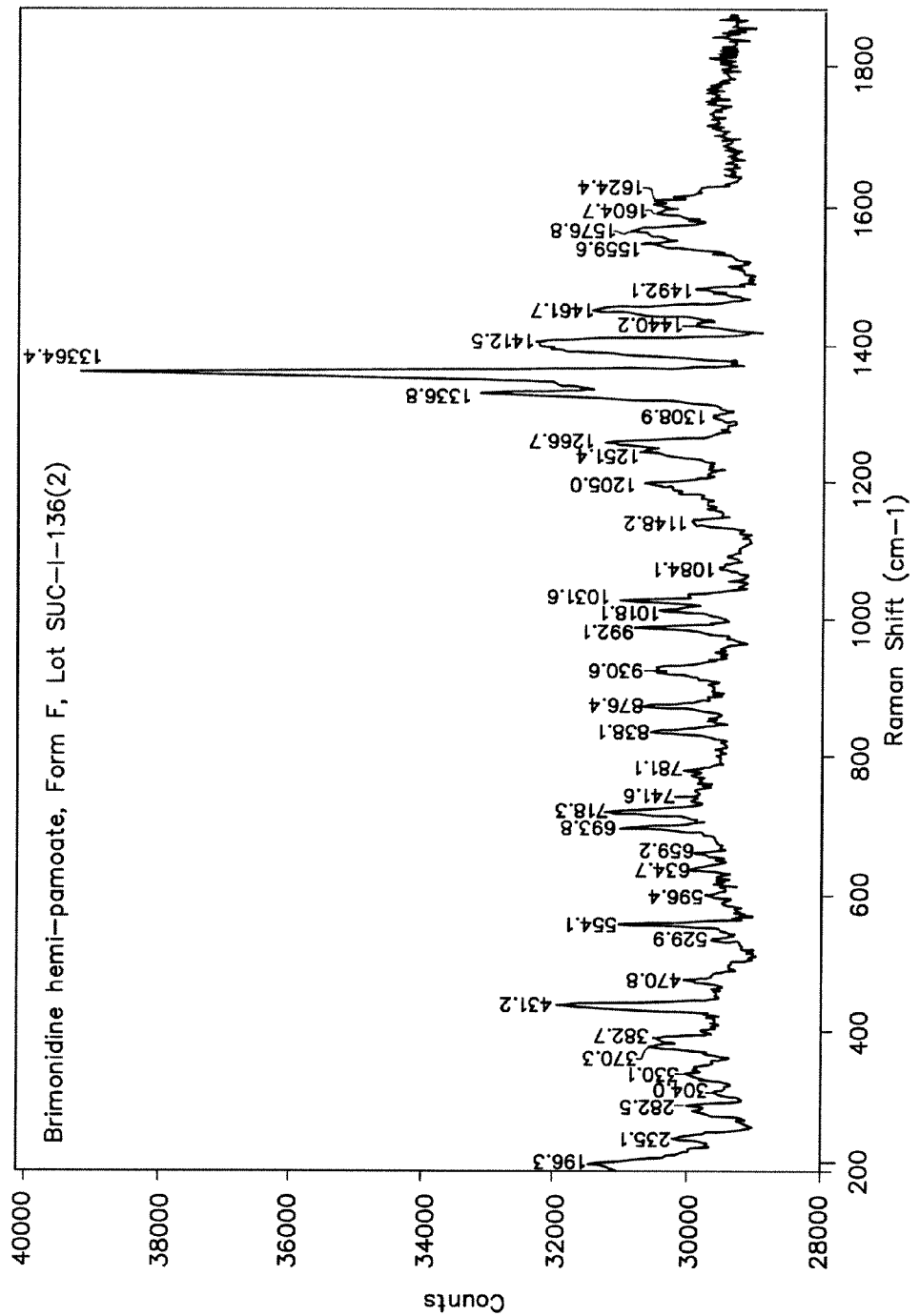
FIG. 31 shows a Raman spectroscopy spectrum of brimonidine pamoate polymorph Form F.

FIG. 31 shows a Raman spectroscopy spectrum of Form F (lot SUC-I-136(2)). This Raman spectrum shows some similarities to Form B (compare FIGS. 11 and 31).

In one aspect, the present invention provides brimonidine pamoate polymorph Form F characterized by a Raman spectroscopy spectrum that comprises peaks at 145.1, 156.3, 1336.8, 1364.4, and 1412.5 cm$^{-1}$.

In another aspect, the present invention provides brimonidine pamoate polymorph Form F characterized by a Raman spectroscopy spectrum that comprises peaks at 131.4, 145.1, 156.3, 176.6, 235.1, 431.2, 693.8, 718.3, 1336.8, 1364.4, 1412.5, 1440.2, and 1461.7 cm$^{-1}$.

Moisture sorption analysis of lot SUC-I-183(1) was performed to further confirm the hydration state of Form F. Form F adsorbed approximately 1.8 molar equivalent of water at 40% RH suggesting a di-hydrate of brimonidine hemi-pamoate. XRPD analysis of the solids following the moisture sorption analysis afforded a diffraction pattern which was consistent with Form F, indicating no form conversion had occurred during the experiment.

In another aspect, the present invention provides a pharmaceutical composition comprising a polymorph of brimonidine pamoate selected from the group consisting of polymorph Forms A, B, C, D, E, F, and combinations thereof.

In still another aspect, the present invention provides a pharmaceutical composition comprising a polymorph of brimonidine pamoate selected from the group consisting of polymorph Forms B, C, D, E, F, and combinations thereof.

In one embodiment, such a pharmaceutical composition comprises an aqueous carrier.

In another embodiment, such a pharmaceutical composition comprises an organic carrier, such as a hydrophobic or a hydrophilic organic material.

In still another embodiment, the pharmaceutical composition comprises brimonidine pamoate polymorph Form B.

In yet another embodiment, the pharmaceutical composition comprises brimonidine pamoate polymorph Form E.

In a further embodiment, the pharmaceutical composition comprises brimonidine pamoate polymorph Form F.

In one aspect, a pharmaceutical composition comprising a polymorph of brimonidine pamoate selected from the group consisting of polymorph Forms A, B, C, D, E, F, and combinations thereof is administered to a subject in need of treatment or control of glaucoma.

In another aspect, a pharmaceutical composition comprising a polymorph of brimonidine pamoate selected from the group consisting of polymorph Forms B, C, D, E, F, and combinations thereof is administered to a subject in need of treatment or control of elevated intraocular pressure.

In still another aspect, the pharmaceutical composition can be used to provide neuroprotection to cells and components of a nervous system. In one embodiment, the nervous system comprises the optic nerve system.

A concentration of at east about 0.3 μg/ml of a brimonidine pamoate polymorph near the site of the damaged tissue is believed adequately to provide therapeutic value for neuroprotection.

In still another aspect, a brimonidine pamoate polymorph is present in the composition in an amount in a range from about 0.0001 to about 95 percent (weight by volume). As used herein, the phrase "1 percent (weight by volume)," for example, means 1 gram in 100 ml of the composition. In one embodiment, the brimonidine pamoate polymorph is present in the composition in an amount in a range from about 0.0005 to about 75 percent (weight by volume), or alternatively, from about 0.001 to about 50, or from about 0.001 to about 25, or from about 0.001 to about 10, or from about 0.001 to about 5, or from about 0.001 to about 1, or from about 0.001 to about 0.5, or from about 0.002 to about 0.2, or from about 0.005 to about 0.1 percent (weight by volume).

In yet another aspect, a brimonidine pamoate polymorph is present in the composition in an amount in a range from about 0.0001 to about 95 percent (by weight of the total composition). In one embodiment, the brimonidine pamoate polymorph is present in the composition in an amount in a range from about 0.0005 to about 75 percent by weight, or alternatively, from about 0.001 to about 50, or from about 0.001 to about 25, or from about 0.001 to about 10, or from about 0.001 to about 5, or from about 0.001 to about 1, or from about 0.001 to about 0.5, or from about 0.002 to about 0.2, or from about 0.005 to about 0.1 percent by weight.

In one embodiment, a composition of the present invention is in a form of a suspension or dispersion. In another embodiment, the suspension or dispersion is based on an aqueous solution. For example, a composition of the present invention can comprise micrometer- or nanometer-sized particles of the complex suspended or dispersed in sterile saline solution. In another embodiment, the suspension or dispersion is based on a hydrophobic medium. For example the micrometer- or nanometer-sized particles of the complex can be suspended in a hydrophobic solvent e.g., silicone oil, mineral oil, or any other suitable nonaqueous medium for delivery to the eye. In still another embodiment, the micrometer- or nanometer-sized particles of the complex can be coated with a physiologically acceptable surfactant (non-limiting examples are disclosed below), then the coated particles are dispersed in a liquid medium. The coating can keep the particles in a suspension. Such a liquid medium can be selected to produce a sustained-release suspension. For example, the liquid medium can be one that is sparingly soluble in the ocular environment into which the suspension is administered. In still another embodiment, the complex is suspended or dispersed in a hydrophobic medium, such as an oil. In still another embodiment, such a medium comprises an emulsion of a hydrophobic material and water. In still another embodiment, the insoluble complex disclosed herein can be dosed by any normal drug delivery vehicle including but not limited to suspension in a liposome formulation (both within and outside the liposome wall or strictly outside the liposome core), in the continuous phase of an emulsion or microemulsion, in the oil phase of the emulsion, or in a micellar solution using either charged or uncharged surfactants. A micellar solution wherein the surfactant is both the micelle forming agent and the anion of the complex disclosed herein would be preferable.

In another aspect, a composition of the present invention can further comprise a non-ionic surfactant, such as polysorbates (such as polysorbate 80 (polyoxyethylene sorbitan monooleate), polysorbate 60 (polyoxyethylene sorbitan monostearate), polysorbate 20 (polyoxyethylene sorbitan monolaurate), commonly known by their trade names of Tween® 80, Tween® 60, Tween® 20), poloxamers (synthetic block polymers of ethylene oxide and propylene oxide, such as those commonly known by their trade names of Pluronic®; e.g., Pluronic® F127 or Pluronic® F108)), or poloxamines (synthetic block polymers of ethylene oxide and propylene oxide attached to ethylene diamine, such as those commonly known by their trade names of Tetronic®; e.g., Tetronic® 1508 or Tetronic® 908, etc., other nonionic surfactants such as Brij®. Myrj®, and long chain fatty alcohols (i.e., oleyl alcohol, stearyl alcohol, myristyl alcohol, docosohexanoyl alcohol, etc.) with carbon chains having about 12 or more carbon atoms (e.g., such as from about 12 to about 24 carbon atoms). Such compounds are delineated in Martindale, $34^{th}$ ed., pp. 1411-1416 (Martindale, "The Complete Drug Reference," S. C. Sweetman (Ed.), Pharmaceutical Press, London, 2005) and in Remington, "The Science and Practice of Pharmacy," $21^{st}$ Ed., p. 291 and the contents of chapter 22, Lippincott Williams & Wilkins, New York, 2006). The concentration of a non-ionic surfactant, when present, in a composition of the present invention can be in the range from about 0.001 to about 5 weight percent (or alternatively, from about 0.01 to about 4, or from about 0.01 to about 2, or from about 0.01 to about 1, or from about 0.01 to about 0.5 weight percent). Any of these surfactants also can be used to coat micrometer- or nanometer-sized particles, as disclosed above.

In addition, a composition of the present invention can include additives such as buffers, diluents, carriers, adjuvants, or other excipients. Any pharmacologically acceptable buffer suitable for application to the eye may be used. Other agents may be employed in the composition for a variety of purposes. For example, buffering agents, preservatives, co-solvents, oils, humectants, emollients, stabilizers, or antioxidants may be employed.

Water-soluble preservatives which may be employed include sodium bisulfite, sodium bisulfate, sodium thiosulfate, benzalkonium chloride, chlorobutanol, thimerosal, ethyl alcohol, methylparaben, polyvinyl alcohol, benzyl alcohol, phenylethyl alcohol, peroxide (such as hydrogen peroxide, urea hydrogen peroxide, or a source that generate a peroxide compound such as perborate), biguanide compounds, and quaternium compounds (such as polyquat-1, polyquat-10, etc.). These agents may be present in individual amounts of from about 0.001 to about 5 percent by weight (preferably, about 0.01 to about 2 percent by weight).

Suitable water-soluble buffering agents that may be employed are sodium carbonate, sodium borate, sodium phosphate, sodium acetate, sodium bicarbonate, etc., as approved by the United States Food and Drug Administration ("US FDA") for the desired route of administration. These agents may be present in amounts sufficient to maintain a pH of the system of between about 5 and about 8. As such, the buffering agent may be as much as about 5 percent on a weight to weight basis of the total composition. Electrolytes such as, but not limited to, sodium chloride and potassium chloride may also be included in the formulation. Physiologically acceptable buffers include, but are not limited to, a phosphate buffer or a Tris-HCl buffer (comprising tris(hydroxymethyl)aminomethane and HCl). For example, a Tris-HCl buffer having pH of 7.4 comprises 3 g/l of tris(hydroxymethyl)aminomethane and 0.76 g/l of HCl. In yet another aspect, the buffer is 10× phosphate buffer saline ("PBS") or 5×PBS solution.

Other buffers also may be found suitable or desirable in some circumstances, such as buffers based on HEPES (N-{2-hydroxyethyl}piperazine-N'-{2-ethanesulfonic acid}) having $pK_a$ of 7.5 at 25° C. and pH in the range of about 6.8-8.2; BES (N,N-bis{2-hydroxyethyl}2-aminoethanesulfonic acid) having $pK_a$ of 7.1 at 25° C. and pH in the range of about 6.4-7.8; MOPS (3-{N-morpholino}propanesulfonic acid)

having pK$_a$ of 7.2 at 25° C. and pH in the range of about 6.5-7.9; TES (N-tris{hydroxymethyl}-methyl-2-aminoethanesulfonic acid) having pK$_a$ of 7.4 at 25° C. and pH in the range of about 6.8-8.2; MOBS (4-{N-morpholino}butanesulfonic acid) having pK$_a$ of 7.6 at 25° C. and pH in the range of about 6.9-8.3; DIPSO (3-(N,N-bis{2-hydroxyethyl}amino)-2-hydroxypropane)) having pK$_a$ of 7.52 at 25° C. and pH in the range of about 7-8.2; TAPSO (2-hydroxy-3{tris(hydroxymethyl)ethylamino}-1-propanesulfonic acid)) having pK$_a$ of 7.61 at 25° C. and pH in the range of about 7-8.2; TAPS ({(2-hydroxy-1,1-bis(hydroxymethyl)ethyl)amino}-1-propanesulfonic acid)) having pK$_a$ of 8.4 at 25° C. and pH in the range of about 7.7-9.1; TABS (N-tris(hydroxymethyl)methyl-4-aminobutanesulfonic acid) having pK$_a$ of 8.9 at 25° C. and pH in the range of about 8.2-9.6; AMPSO(N-(1,1-dimethyl-2-hydroxyethyl)-3-amino-2-hydroxypropanesulfonic acid)) having pK$_a$ of 9.0 at 25° C. and pH in the range of about 8.3-9.7; CHES (2-cyclohexylamino)ethanesulfonic acid) having pK$_a$ of 9.5 at 25° C. and pH in the range of about 8.6-10.0; CAPSO (3-(cyclohexylamino)-2-hydroxy-1-propanesulfonic acid) having pK$_a$ of 9.6 at 25° C. and pH in the range of about 8.9-10.3; or CAPS (3-(cyclohexylamino)-1-propane sulfonic acid) having pK$_a$ of 10.4 at 25° C. and pH in the range of about 9.7-11.1.

In one aspect, the composition has a pH that is suitable for administration into a subject; e.g., to render the composition non-irritating. For example, for topical ophthalmic administration, a desired pH is in the range from about 5 to about 8.

In one aspect, the composition has a pH of about 7. Alternatively, the composition has a pH in a range from about 7 to about 7.5.

In another aspect, the composition has a pH of about 7.4.

In yet another aspect, a composition also can comprise a viscosity-modifying compound designed to facilitate the administration of the composition into the subject or to promote the bioavailability in the subject. In still another aspect, the viscosity-modifying compound may be chosen so that the composition is not readily dispersed after being administered into an ocular environment (such as the ocular surface, conjunctiva, or vitreous). Such compounds may enhance the viscosity of the composition, and include, but are not limited to: monomeric polyols, such as, glycerol, propylene glycol, ethylene glycol; polymeric polyols, such as, polyethylene glycol; various polymers of the cellulose family, such as hydroxypropylmethyl cellulose ("HPMC"), carboxymethyl cellulose ("CMC") sodium, hydroxypropyl cellulose ("HPC"); polysaccharides, such as hyaluronic acid and its salts, chondroitin sulfate and its salts, dextrans, such as, dextran 70; water soluble proteins, such as gelatin; vinyl polymers, such as, polyvinyl alcohol, polyvinylpyrrolidone, povidone; carbomers, such as carbomer 934P, carbomer 941, carbomer 940, or carbomer 974P; and acrylic acid polymers. In general, a desired viscosity can be in the range from about 1 to about 400 centipoises ("cp" or mPa·s).

In another aspect, the present invention provides a method for producing a composition comprising a brimonidine pamoate polymorph selected from the group consisting of polymorph Forms A, B, C, D, E, F, and combinations thereof (or alternatively, polymorph Forms B, C, D, E, F, and combinations thereof), the method comprising: (a) providing said brimonidine pamoate polymorph; and (b) dispersing an amount of said polymorph in a sufficient amount of said medium to produce said composition to achieve a predetermined concentration of said polymorph in said medium. Alternatively, a portion of the polymorph remains in a solid phase for a period longer than 2 days, or 1 week, or 1 month, or 2 months, or 3 months, or 4 months, or 5 months, or 6 months, or 1 year, or 2 years after said polymorph has been in contact with said medium. In one embodiment, the method can optionally include a step of reducing the size of the polymorph before dispersing such polymorph in the medium.

In still another aspect, the present invention provides a method for producing brimonidine pamoate polymorph Form B or F. The method comprises: (a) producing brimonidine pamoate polymorph Form A; (b) contacting said polymorph Form A with water for a time sufficient to convert said polymorph Form A to polymorph Form B or F.

In still another aspect, the present invention provides a method for producing brimonidine pamoate polymorph Form B or F. The method comprises: (a) producing brimonidine pamoate polymorph Form A, C, D, E, or a combination thereof; (b) contacting said polymorph Form A, C, D, E, or combination thereof with water for a time sufficient to convert said polymorph Form A, C, D, E, or combination thereof to polymorph Form B or F.

In yet another aspect, the present invention provides a method for producing brimonidine pamoate polymorph Form E. The method comprises: (a) producing brimonidine pamoate polymorph Form A; (b) contacting said polymorph Form A with THF for a time sufficient to convert said polymorph Form A to polymorph Form E.

In a further aspect, the present invention provides a method for producing brimonidine pamoate polymorph Form E. The method comprises: (a) producing brimonidine pamoate polymorph Form A, B, C, D, or a combination thereof; (b) contacting said polymorph Form A, B, C, D, or combination thereof with THF for a time sufficient to convert said polymorph Form A, B, C, D, or combination thereof to polymorph Form E.

In another aspect, a formulation comprising a brimonidine pamoate polymorph selected from the group consisting of polymorph Forms A, B, C, D, E, F, and combinations thereof (or alternatively, polymorph Forms B, C, D, E, F, and combinations thereof) is prepared for topical administration, periocular injection, or intravitreal injection. An injectable intravitreal formulation can desirably comprise a carrier that provides a sustained-release of the active ingredients, such as for a period longer than about one day, or one week, or longer than about 1, 2, 3, 4, 5, or 6 months, or 1 or 2 years. In certain embodiments, the sustained-release formulation desirably comprises a carrier that is insoluble or only sparingly soluble in an ocular environment (such as the ocular surface, conjunctiva, or vitreous). Such a carrier can be an oil-based liquid, emulsion, gel, or semisolid. Non-limiting examples of oil-based liquids include castor oil, peanut oil, olive oil, coconut oil, sesame oil, cottonseed oil, corn oil, sunflower oil, fish-liver oil, arachis oil, and liquid paraffin.

In one aspect, a composition of the present invention can be administered into a subject in need of neuroprotection at one time or over a series of treatments. A composition of the present invention may be administered locally; e.g., intravitreally by intrabulbar injection for ocular neuroprotection, or by intrathecal or epidural administration for spinal protection. Many of the compositions of the invention can be administered systemically; e.g., orally, or intravenously, or by intramuscular injection. In addition, compositions for protection of the retina and optic nerve that are capable of passing through the cornea and achieving sufficient concentration in the vitreous humor (such as a concentration disclosed herein above) may also be administered topically to the eye. In one embodiment, the neuroprotection can prevent progressive damage to cells or components of the optic nerve, which damage results from glaucoma, retinitis pigmentosa, AMD, diabetic retinopathy, diabetic macular edema, or other back-of-the-eye diseases.

In one embodiment, a composition of the present invention can be injected intravitreally, for example through the pars plana of the ciliary body, to treat or prevent glaucoma or progression thereof, or to provide neuroprotection to the optic nerve system, using a fine-gauge needle, such as 25-30 gauge. Typically, an amount from about 25 µl to about 100 µl of a composition comprising a brimonidine pamoate polymorph disclosed herein is administered into a patient. A concentration of such a polymorph is selected from the ranges disclosed above.

In still another aspect, a brimonidine pamoate polymorph selected from the group consisting of polymorph Forms A, B, C, D, E, F, and combinations thereof (or alternatively, polymorph Forms B, C, D, E, F, and combinations thereof) is incorporated into an ophthalmic device or system that comprises a biodegradable material, and the device is injected or implanted into a subject to provide a long-term (e.g., longer than about 1 week, or longer than about 1, 2, 3, 4, 5, or 6 months, or 1 or 2 years) treatment or prevention of glaucoma or progression thereof or to provide neuroprotection to the optic nerve system. In some embodiments, the ophthalmic device or system can comprise a semipermeable membrane that allows the complex to diffuse therethrough at a controlled rate. In still some other embodiments, such a controlled rate provides a supply of the complex over an extended period of time at or near the site of desired treatment. Such a device system may be injected or implanted by a skilled physician in the subject's ocular or periocular tissue.

Some compositions of the present invention are disclosed in the examples below. It should be understood that the proportions of the listed ingredients may be adjusted for specific circumstances.

EXAMPLE 1

TABLE 1

| Ingredient | Amount |
| --- | --- |
| Carbopol 934P NF | 0.25 g |
| Purified water | 99.75 g |
| Propylene glycol | 5 g |
| EDTA | 0.1 mg |
| Brimonidine pamoate polymorph Form B | 100 mg |

An appropriate proportion of EDTA (e.g., shown in Table 1) is added to purified water in a stainless steel jacketed vessel that is equipped with a stirring mechanism. An appropriate amount of carbopol 934P NF is added, over a period of five to ten minutes to form a substantially uniform dispersion. Propylene glycol is added to the resulting mixture while mixing for three to ten minutes. Then, an appropriate amount to brimonidine pamoate having polymorph Form B, which may be previously micronized, is added to the contents of the vessel over a period of three to five minutes while mixing continues until the compound is substantially dispersed. The pH of the mixture is adjusted to 7-7.5 using 1 N NaOH or 1 N HCL solution. The final composition is sterilized, using, for example, heat or radiation and then packaged in appropriate containers.

EXAMPLE 2

A procedure similar to that disclosed in Example 1 is used to produce the composition of the present invention having the ingredients listed in Table 2.

TABLE 2

| Ingredient | Amount (% by weight, except where "ppm" is indicated) |
| --- | --- |
| Povidone | 1.5 |
| HAP (30%) | 0.05 |
| Glycerin | 3 |
| Propylene glycol | 3 |
| Brimonidine pamoate polymorph Form F | 0.5 |
| Alexidine 2HCl | 1-2 ppm |
| Purified water | q.s. to 100 |

Note:
"HAP" denotes hydroxyalkyl phosphonates, such as those known under the trade name Dequest ®. HAPs can be used as chelating agents and have been shown to inhibit bacterial and fungal cell replication.

EXAMPLE 3

A procedure similar to that disclosed in Example 1 is used to produce the composition of the present invention having the ingredients listed in Table 3.

TABLE 3

| Ingredient | Amount (% by weight, except where "ppm" is indicated) |
| --- | --- |
| Glycerin | 3 |
| Propylene glycol | 3 |
| Brimonidine pamoate polymorph Form E | 0.25 |
| Alexidine | 1-2 ppm |
| Sunflower oil | q.s. to 100 |

EXAMPLE 4

A modification of the procedure disclosed in Example 1 is used to produce the composition of the present invention having the ingredients listed in Table 4.

An appropriate proportion of polysorbate 80 (e.g., shown in Table 4) is added to approximately 20 percent of the desired final volume of purified water in a stainless steel jacketed vessel that is equipped with a stirring mechanism. Glycerin and propylene glycol are then added to the mixture while mixing continues for five more minutes. To a sterilized second vessel, heated to about 80° C. and equipped with a stirring mechanism, containing approximately 70 percent of the desired final volume of purified water, an appropriate amount of CMC-MV is added over a period of three to five minutes while mixing continues until the CMC forms a substantially uniform solution. The contents of the second vessel are cooled to about room temperature and then the contents of the first vessel are transferred into the second vessel. The remaining of the desired volume of purified water is added to the second vessel. Then, appropriate amounts of brimonidine pamoate polymorphs Form B and Form F are added to the contents of the second vessel over a period of three to five minutes while mixing continues until the drugs are substantially uniformly dispersed. The pH of the mixture is adjusted to 7-7.5 using 1 N NaOH or 1 N HCl solution. The final composition is sterilized, using, for example, heat or radiation, and packaged in appropriate containers.

TABLE 4

| Ingredient | Amount (% by weight, except where "ppm" is indicated) |
| --- | --- |
| Carboxymethyl cellulose, medium viscosity ("CMC-MV") | 0.5 |
| Glycerin | 3 |
| Propylene glycol | 3 |
| Brimonidine pamoate polymorph Form B | 0.3 |
| Brimonidine pamoate polymorph Form F | 0.3 |
| Polysorbate 80 ® (a surfactant) | 0.25 |
| Alexidine 2HCl | 1-2 ppm |
| Purified water | q.s. to 100 |

EXAMPLE 5

A procedure similar to that of Example 1 is used to produce a composition comprising the ingredients listed in Table 5.

TABLE 5

| Ingredient | Amount (% by weight, except where "ppm" is indicated) |
| --- | --- |
| Glycerin | 3 |
| Propylene glycol | 3 |
| Brimonidine pamoate polymorph Form E | 0.5 |
| Tween ® 80 | 0.25 |
| Alexidine | 1-2 ppm |
| Corn oil | q.s. to 100 |

EXAMPLE 6

A procedure similar to that of Example 4 is used to produce a composition comprising the ingredients listed in Table 6.

TABLE 6

| Ingredient | Amount (% by weight, except where "ppm" is indicated) |
| --- | --- |
| CMC (MV) | 0.5 |
| Glycerin | 3 |
| Propylene glycol | 3 |
| Brimonidine pamoate polymorph Form B | 0.75 |
| Brimonidine pamoate polymorph Form A | 0.75 |
| Tyloxapol (a surfactant) | 0.25 |
| Alexidine 2HCl | 1-2 ppm |
| Purified water | q.s. to 100 |

EXAMPLE 7

A procedure similar that of Example 1 is used to produce a composition comprising the ingredients listed in Table 7.

TABLE 7

| Ingredient | Amount (% by weight, except where "ppm" is indicated) |
| --- | --- |
| HPMC | 0.5 |
| Glycerin | 3 |
| Propylene glycol | 3 |
| Brimonidine pamoate polymorph Form A | 0.6 |
| Brimonidine pamoate polymorph Form C | 0.6 |
| Brimonidine pamoate polymorph Form D | 0.6 |
| Tyloxapol (a surfactant) | 0.25 |
| Alexidine 2HCl | 1-2 ppm |
| Purified water | q.s. to 100 |

Alternatively, purified water may be substituted with an oil, such as fish-liver oil, peanut oil, sesame oil, coconut oil, sunflower oil, corn oil, or olive oil to produce an oil-based formulation comprising a brimonidine pamoate polymorph.

Benefits of brimonidine pamoate polymorphs, or compositions comprising the same, of the present invention for neuroprotection can be determined, judged, estimated, or inferred by conducting assays and measurements, for example, to determine: (1) the protection of nerve cells from glutamate induced toxicity; and/or (2) the neural protection in a nerve crush model of mechanical injury. Non-limiting examples of such assays and measurements are disclosed in U.S. Pat. No. 6,194,415, which is incorporated herein by reference.

The following sections disclose the instrumentation and procedures used in applicable experiments disclosed hereinabove.

Instrumentation

| Instrument | Name and Model Number |
| --- | --- |
| Differential Scanning Calorimeter | Mettler 822$^e$ DSC |
| Thermal Gravimetric Analyzer | Mettler 851$^e$ SDTA/TGA |
| X-Ray Powder Diffraction System | Shimadzu XRD-6000 |
| Moisture-Sorption Analysis | IGAsorp Moisture Sorption Instrument |
| Nuclear Magnetic Resonance Spectrometer | 500 MHz Bruker AVANCE |
| High-Performance Liquid Chromatography | Waters Alliance |
| Raman Spectrometer | Kaiser RXN1 |

Differential Scanning Calorimetry

Differential scanning calorimetry ("DSC") analyses were carried out on the samples "as is". Samples were weighed in an aluminum pan, covered with a pierced lid, and then crimped. Analysis conditions were 30° C. to 30-300 or 350° C. ramped at 10° C./minute.

Thermal Gravimetric Analysis

Thermal gravimetric analysis ("TGA") analyses were carried out on the samples "as is". Samples were weighed in an alumina crucible and analyzed from 30° C. to 230° C. at 10° C./minute.

X-Ray Powder Diffraction

Samples for x-ray powder diffraction ("XRPD") were analyzed "as is". Samples were placed on Si zero-return ultra-micro sample holders and analyzed using the following conditions:

| X-ray tube: | Cu Kα, 40 kV, 30 mA |
| --- | --- |
| Slits | |
| Divergence Slit | 1.00 deg |
| Scatter Slit | 1.00 deg |
| Receiving Slit | 0.30 mm |
| Scanning | |
| Scan Range | 3.0-45.0 deg |
| Scan Mode | Continuous |
| Step Size | 0.04° |
| Scan Rate | 2°/minute |

Moisture-Sorption Analysis

Moisture sorption analysis was performed on brimonidine hemi-pamoate starting material at 25° C. from 40 to 90% relative humidity ("RH") for the adsorption scan, from 85 to 0% RH from the desorption scan and 10 to 40% RH to complete the adsorption scan. Approximately 10 mg of the sample was analyzed in a Pyrex bulb. Each scan utilized a step size of 10% RH and a maximum equilibration time of four hours per point. The sample was dried for one hour at 80° C. following the desorption scan to obtain the dry sample weight and then it was analyzed by XRPD.

Nuclear Magnetic Resonance

Samples (~2 to 10 mg) of brimonidine hemi-pamoate were dissolved in DMSO-$d_6$ with 0.05% tetramethylsilane ("TMS") for internal reference. $^1$H NMR spectra were acquired at 500 MHz using 5 mm broadband observe ($^1$H—X) Z gradient probe. A 30 degree pulse with 20 ppm spectral width, 1.0 s repetition rate, and 16 to 128 transients were utilized in acquiring the spectra.

High Performance Liquid Chromatography
Instrument Parameters:
Column: Agilent Eclipse XDB-C18, 4.6×150 mm
Mobile Phase A: 0.05% TFA in water
Mobile Phase B: 0.05% TFA in MeCN
Flow Rate: 1.0 mL/min
Column Temperature Ambient
Detection: 248 nm
Diluent: MeOH
Injection Volume: 5 µl

| Gradient Conditions | | |
|---|---|---|
| Time (minutes) | % A | % B |
| 0 | 90 | 10 |
| 10 | 80 | 20 |
| 15 | 10 | 90 |
| 22 | 90 | 10 |

Raman Spectroscopy

Samples for Raman spectroscopy analysis were analyzed "as is". Samples were placed in a 96 well plate and analyzed using the following conditions:

| | |
|---|---|
| Raman Source: | 785 nm laser |
| Objective: | 1.2 mm PHaT |
| Single Exposure Time: | 12 seconds |
| Co-Additions: | 12 |
| Enabled Exposure Options: | Cosmic Ray filtering |
| | Dark Subtraction |
| | Intensity Calibration |

Peak Data List for FIG. 1.

| Peak Data List | | | | | |
|---|---|---|---|---|---|
| No. | 2Theta (degrees) | d (A) | I (counts) | I/Io | FWHM (degrees) | integrated I (counts) |
| 1 | 4.2466 | 20.79077 | 187 | 18 | 0.2185 | 1121 |
| 2 | 7.6046 | 11.61596 | 306 | 29 | 0.2754 | 2445 |
| 3 | 7.9817 | 11.06798 | 92 | 9 | 0.2701 | 645 |
| 4 | 8.4780 | 10.42114 | 49 | 5 | 0.2132 | 287 |
| 5 | 10.2865 | 8.59267 | 71 | 7 | 0.2589 | 516 |
| 6 | 10.6400 | 8.30797 | 50 | 5 | 0.3288 | 568 |
| 7 | 12.2376 | 7.22673 | 310 | 29 | 0.2694 | 2347 |
| 8 | 12.6551 | 6.98924 | 370 | 35 | 0.2541 | 2532 |
| 9 | 13.5142 | 6.54680 | 708 | 67 | 0.2539 | 5267 |
| 10 | 15.9242 | 5.56101 | 407 | 39 | 0.2813 | 3253 |
| 11 | 17.2082 | 5.14885 | 95 | 9 | 0.2814 | 759 |
| 12 | 17.5600 | 5.04649 | 69 | 7 | 0.2200 | 432 |
| 13 | 17.9600 | 4.93498 | 56 | 5 | 0.2172 | 304 |
| 14 | 18.2926 | 4.84600 | 82 | 8 | 0.3587 | 798 |
| 15 | 19.0500 | 4.65500 | 46 | 4 | 0.2200 | 337 |
| 16 | 20.5858 | 4.31105 | 536 | 51 | 0.3056 | 4728 |
| 17 | 21.1359 | 4.20007 | 1054 | 100 | 0.3147 | 8574 |
| 18 | 21.6400 | 4.10336 | 61 | 6 | 0.2400 | 656 |
| 19 | 22.3600 | 3.97283 | 53 | 5 | 0.1530 | 195 |
| 20 | 22.6778 | 3.91787 | 184 | 17 | 0.3008 | 1664 |
| 21 | 23.7822 | 3.73837 | 180 | 17 | 0.2685 | 1282 |
| 22 | 24.3653 | 3.65021 | 465 | 44 | 0.4763 | 5402 |
| 23 | 25.2130 | 3.52937 | 79 | 7 | 0.3140 | 668 |
| 24 | 25.7958 | 3.45094 | 80 | 8 | 0.2583 | 533 |
| 25 | 26.5170 | 3.35870 | 339 | 32 | 0.2629 | 2795 |
| 26 | 26.9200 | 3.30933 | 94 | 9 | 0.0000 | 0 |
| 27 | 27.1600 | 3.28062 | 100 | 9 | 0.0000 | 0 |
| 28 | 27.6643 | 3.22196 | 312 | 30 | 0.4589 | 3993 |
| 29 | 28.3600 | 3.14448 | 65 | 6 | 0.1930 | 466 |
| 30 | 29.0700 | 3.06927 | 143 | 14 | 0.3480 | 1289 |
| 31 | 29.7594 | 2.99972 | 106 | 10 | 0.4469 | 1420 |
| 32 | 31.4704 | 2.84042 | 147 | 14 | 0.2799 | 1309 |
| 33 | 31.8800 | 2.80486 | 46 | 4 | 0.0000 | 0 |
| 34 | 32.1600 | 2.78107 | 72 | 7 | 0.2934 | 648 |
| 35 | 33.1200 | 2.70262 | 45 | 4 | 0.4960 | 606 |
| 36 | 33.5373 | 2.66994 | 82 | 8 | 0.3253 | 653 |
| 37 | 34.1811 | 2.62111 | 78 | 7 | 0.4378 | 800 |
| 38 | 34.5200 | 2.59615 | 40 | 4 | 0.2400 | 340 |
| 39 | 36.0203 | 2.49138 | 44 | 4 | 0.5860 | 625 |
| 40 | 36.6483 | 2.45012 | 37 | 4 | 0.4033 | 315 |
| 41 | 37.4400 | 2.40011 | 54 | 5 | 0.2156 | 476 |
| 42 | 37.6800 | 2.38537 | 50 | 5 | 0.0000 | 0 |
| 43 | 38.0000 | 2.36602 | 43 | 4 | 0.0000 | 0 |
| 44 | 38.2000 | 2.35409 | 35 | 3 | 0.4000 | 291 |
| 45 | 38.5600 | 2.33294 | 33 | 3 | 0.8444 | 427 |
| 46 | 39.5569 | 2.27641 | 43 | 4 | 0.2088 | 237 |
| 47 | 40.1748 | 2.24281 | 88 | 8 | 0.2845 | 753 |
| 48 | 40.8706 | 2.20622 | 42 | 4 | 0.1922 | 236 |
| 49 | 41.1614 | 2.19130 | 44 | 4 | 0.2229 | 259 |
| 50 | 41.5793 | 2.17024 | 32 | 3 | 0.1925 | 184 |

Peak Data List for FIG. 7

| Peak Data List | | | | | |
|---|---|---|---|---|---|
| No. | 2Theta (degrees) | d (A) | I (counts) | I/Io | FWHM (degrees) | integrated I (counts) |
| 1 | 3.1200 | 28.29512 | 60 | 5 | 0.0960 | 176 |
| 2 | 6.6400 | 13.30110 | 77 | 7 | 0.1214 | 486 |
| 3 | 6.9590 | 12.69208 | 346 | 31 | 0.2045 | 1993 |
| 4 | 9.2400 | 9.56338 | 40 | 4 | 0.1334 | 331 |
| 5 | 9.6919 | 9.11846 | 1125 | 100 | 0.1549 | 5388 |
| 6 | 10.0800 | 8.76824 | 64 | 6 | 0.0972 | 469 |
| 7 | 10.9152 | 8.09912 | 328 | 29 | 0.1651 | 1745 |
| 8 | 11.2000 | 7.89380 | 43 | 4 | 0.1500 | 350 |
| 9 | 12.8400 | 6.88901 | 45 | 4 | 0.2666 | 407 |
| 10 | 13.0646 | 6.77108 | 112 | 10 | 0.1853 | 481 |
| 11 | 13.9829 | 6.32839 | 133 | 12 | 0.2059 | 900 |
| 12 | 14.6097 | 6.05827 | 464 | 41 | 0.2178 | 2875 |
| 13 | 15.8563 | 5.58467 | 115 | 10 | 0.1547 | 678 |
| 14 | 16.3336 | 5.42253 | 210 | 19 | 0.2007 | 1304 |
| 15 | 16.9123 | 5.23827 | 40 | 4 | 0.1398 | 227 |
| 16 | 17.7200 | 5.00128 | 137 | 12 | 0.1692 | 693 |
| 17 | 17.9200 | 4.94591 | 168 | 15 | 0.1926 | 807 |
| 18 | 18.4065 | 4.81627 | 78 | 7 | 0.1570 | 399 |
| 19 | 19.0254 | 4.66096 | 347 | 31 | 0.1579 | 1626 |
| 20 | 19.4563 | 4.55870 | 172 | 15 | 0.1734 | 856 |
| 21 | 20.1020 | 4.41370 | 309 | 27 | 0.1757 | 1429 |
| 22 | 20.4080 | 4.34821 | 68 | 6 | 0.2240 | 415 |

-continued

Peak Data List

| No. | 2Theta (degrees) | d (A) | I (counts) | I/Io | FWHM (degrees) | integrated I (counts) |
|---|---|---|---|---|---|---|
| 23 | 20.7623 | 4.27480 | 153 | 14 | 0.1809 | 711 |
| 24 | 21.0242 | 4.22214 | 183 | 16 | 0.1742 | 949 |
| 25 | 21.9600 | 4.04428 | 122 | 11 | 0.1724 | 647 |
| 26 | 22.1600 | 4.00823 | 204 | 18 | 0.1576 | 817 |
| 27 | 22.4400 | 3.95885 | 69 | 6 | 0.1472 | 367 |
| 28 | 23.3503 | 3.80653 | 386 | 34 | 0.1740 | 1895 |
| 29 | 24.0046 | 3.70424 | 91 | 8 | 0.1416 | 432 |
| 30 | 25.0920 | 3.54612 | 219 | 19 | 0.1582 | 1114 |
| 31 | 25.4804 | 3.49294 | 122 | 11 | 0.1325 | 429 |
| 32 | 25.9362 | 3.43258 | 437 | 39 | 0.1842 | 2312 |
| 33 | 26.4632 | 3.36540 | 364 | 32 | 0.2195 | 2126 |
| 34 | 26.8834 | 3.31375 | 185 | 16 | 0.2629 | 1292 |
| 35 | 27.4400 | 3.24778 | 63 | 6 | 0.0868 | 201 |
| 36 | 27.6748 | 3.22076 | 312 | 28 | 0.1980 | 2113 |
| 37 | 27.9600 | 3.18855 | 167 | 15 | 0.0000 | 0 |
| 38 | 28.2000 | 3.16196 | 86 | 8 | 0.1600 | 1020 |
| 39 | 28.8839 | 3.08863 | 136 | 12 | 0.1444 | 489 |
| 40 | 29.1200 | 3.06412 | 93 | 8 | 0.1790 | 571 |
| 41 | 29.8002 | 2.99571 | 36 | 3 | 0.2075 | 277 |
| 42 | 30.2953 | 2.94787 | 176 | 16 | 0.2227 | 1128 |
| 43 | 31.0177 | 2.88084 | 56 | 5 | 0.1511 | 254 |
| 44 | 31.8400 | 2.80829 | 76 | 7 | 0.1544 | 462 |
| 45 | 32.0919 | 2.78682 | 105 | 9 | 0.2202 | 638 |
| 46 | 32.7087 | 2.73566 | 43 | 4 | 0.1375 | 260 |
| 47 | 34.4000 | 2.60493 | 34 | 3 | 0.1400 | 318 |
| 48 | 36.0075 | 2.49224 | 71 | 6 | 0.1650 | 510 |
| 49 | 36.3455 | 2.46984 | 53 | 5 | 0.1257 | 223 |
| 50 | 36.8388 | 2.43789 | 59 | 5 | 0.1483 | 269 |

Peak Data List for FIG. 12

Peak Data List

| No. | 2Theta (degrees) | d (A) | I (counts) | I/Io | FWHM (degrees) | integrated I (counts) |
|---|---|---|---|---|---|---|
| 1 | 3.1600 | 27.93705 | 12 | 4 | 0.0400 | 12 |
| 2 | 3.4220 | 25.79866 | 39 | 12 | 0.1025 | 103 |
| 3 | 3.7040 | 23.83511 | 88 | 27 | 0.2962 | 670 |
| 4 | 4.8400 | 18.24300 | 10 | 3 | 0.0572 | 13 |
| 5 | 6.6933 | 13.19530 | 14 | 4 | 0.1067 | 46 |
| 6 | 7.1200 | 12.40544 | 23 | 7 | 0.1236 | 122 |
| 7 | 7.3600 | 12.00144 | 50 | 16 | 0.2000 | 289 |
| 8 | 7.6582 | 11.53478 | 218 | 68 | 0.2728 | 1412 |
| 9 | 8.4163 | 10.49740 | 32 | 10 | 0.2073 | 216 |
| 10 | 9.2650 | 9.53763 | 13 | 4 | 0.1700 | 79 |
| 11 | 9.6339 | 9.17323 | 12 | 4 | 0.1835 | 94 |
| 12 | 11.1323 | 7.94165 | 59 | 18 | 0.3446 | 617 |
| 13 | 11.9947 | 7.37253 | 63 | 20 | 0.2106 | 478 |
| 14 | 12.8351 | 6.89163 | 321 | 100 | 0.2454 | 2388 |
| 15 | 13.4414 | 6.58210 | 203 | 63 | 0.3724 | 2174 |
| 16 | 13.9943 | 6.32327 | 45 | 14 | 0.2114 | 284 |
| 17 | 14.3866 | 6.15171 | 10 | 3 | 0.1467 | 41 |
| 18 | 14.9013 | 5.94036 | 31 | 10 | 0.2712 | 230 |
| 19 | 15.4581 | 5.72762 | 71 | 22 | 0.3438 | 633 |
| 20 | 15.9600 | 5.54862 | 53 | 17 | 0.3134 | 506 |
| 21 | 16.9566 | 5.22468 | 39 | 12 | 0.1721 | 218 |
| 22 | 18.3959 | 4.81902 | 171 | 53 | 0.2237 | 1257 |
| 23 | 19.1563 | 4.62941 | 109 | 34 | 0.2102 | 725 |
| 24 | 19.8131 | 4.47740 | 117 | 36 | 0.2315 | 796 |
| 25 | 20.5843 | 4.31136 | 10 | 3 | 0.0886 | 48 |
| 26 | 20.9200 | 4.24293 | 15 | 5 | 0.1900 | 91 |
| 27 | 21.3600 | 4.15651 | 88 | 27 | 0.3658 | 577 |
| 28 | 21.6000 | 4.11087 | 48 | 15 | 0.5120 | 430 |
| 29 | 22.1600 | 4.00823 | 30 | 9 | 0.3200 | 282 |
| 30 | 22.6435 | 3.92373 | 121 | 38 | 0.2281 | 746 |
| 31 | 23.0400 | 3.85709 | 15 | 5 | 0.1226 | 144 |
| 32 | 23.4800 | 3.78580 | 41 | 13 | 0.1090 | 133 |
| 33 | 23.7994 | 3.73571 | 216 | 67 | 0.2887 | 1711 |

-continued

Peak Data List

| No. | 2Theta (degrees) | d (A) | I (counts) | I/Io | FWHM (degrees) | integrated I (counts) |
|---|---|---|---|---|---|---|
| 34 | 24.4000 | 3.64510 | 41 | 13 | 0.2934 | 455 |
| 35 | 25.0440 | 3.55281 | 37 | 12 | 0.2480 | 262 |
| 36 | 25.8800 | 3.43991 | 42 | 13 | 0.1280 | 277 |
| 37 | 26.4800 | 3.36331 | 41 | 13 | 0.0000 | 0 |
| 38 | 27.0221 | 3.29705 | 82 | 26 | 0.2708 | 1269 |
| 39 | 27.4800 | 3.24315 | 62 | 19 | 0.0000 | 0 |
| 40 | 27.7600 | 3.21107 | 34 | 11 | 0.4228 | 493 |
| 41 | 28.3200 | 3.14883 | 35 | 11 | 0.2312 | 166 |
| 42 | 28.5200 | 3.12720 | 39 | 12 | 0.2488 | 228 |
| 43 | 28.9543 | 3.08128 | 16 | 5 | 0.2286 | 95 |
| 44 | 29.3227 | 3.04340 | 63 | 20 | 0.3196 | 528 |
| 45 | 30.2600 | 2.95123 | 26 | 8 | 0.2000 | 159 |
| 46 | 30.5457 | 2.92427 | 10 | 3 | 0.1314 | 29 |
| 47 | 30.8000 | 2.90071 | 15 | 5 | 0.0700 | 24 |
| 48 | 31.0600 | 2.87701 | 22 | 7 | 0.3600 | 206 |
| 49 | 31.4413 | 2.84299 | 14 | 4 | 0.1093 | 46 |
| 50 | 32.0800 | 2.78783 | 28 | 9 | 0.1334 | 125 |

Peak data List for FIG. 17

Peak Data List

| No. | 2Theta (degrees) | d (A) | I (counts) | I/Io | FWHM (degrees) | integrated I (counts) |
|---|---|---|---|---|---|---|
| 1 | 7.0800 | 12.47543 | 14 | 7 | 0.1600 | 119 |
| 2 | 7.5471 | 11.70433 | 212 | 100 | 0.3942 | 2076 |
| 3 | 8.5000 | 10.39422 | 6 | 3 | 0.2000 | 29 |
| 4 | 10.3000 | 8.58144 | 8 | 4 | 0.2000 | 45 |
| 5 | 11.1091 | 7.95819 | 65 | 31 | 0.4000 | 679 |
| 6 | 12.0800 | 7.32066 | 22 | 10 | 0.2666 | 249 |
| 7 | 12.7821 | 6.92008 | 142 | 67 | 0.5108 | 1870 |
| 8 | 13.3200 | 6.64181 | 26 | 12 | 0.2000 | 221 |
| 9 | 14.0223 | 6.31070 | 27 | 13 | 0.4126 | 301 |
| 10 | 15.3038 | 5.78502 | 40 | 19 | 0.3790 | 367 |
| 11 | 15.9720 | 5.54447 | 22 | 10 | 0.3760 | 215 |
| 12 | 16.7906 | 5.27596 | 8 | 4 | 0.2053 | 45 |
| 13 | 17.5441 | 5.05102 | 16 | 8 | 0.3783 | 144 |
| 14 | 18.4425 | 4.80695 | 67 | 32 | 0.4050 | 727 |
| 15 | 19.3884 | 4.57451 | 95 | 45 | 0.4854 | 1168 |
| 16 | 19.9200 | 4.45362 | 21 | 10 | 0.3000 | 221 |
| 17 | 20.8733 | 4.25232 | 23 | 11 | 0.7067 | 437 |
| 18 | 21.9200 | 4.05157 | 40 | 19 | 0.6400 | 997 |
| 19 | 22.4800 | 3.95190 | 63 | 30 | 0.0000 | 0 |
| 20 | 23.0800 | 3.85050 | 75 | 35 | 0.6080 | 1572 |
| 21 | 24.5139 | 3.62842 | 145 | 68 | 0.7536 | 2918 |
| 22 | 25.7200 | 3.46094 | 56 | 26 | 0.3854 | 641 |
| 23 | 26.4400 | 3.36830 | 71 | 33 | 0.6000 | 1054 |
| 24 | 27.1018 | 3.28754 | 147 | 69 | 0.9236 | 2866 |
| 25 | 28.6586 | 3.11239 | 49 | 23 | 0.6507 | 842 |
| 26 | 29.5960 | 3.01591 | 14 | 7 | 0.4720 | 143 |
| 27 | 29.9200 | 2.98399 | 7 | 3 | 0.2400 | 51 |
| 28 | 30.6800 | 2.91178 | 11 | 5 | 0.4000 | 126 |
| 29 | 32.3200 | 2.76767 | 21 | 10 | 0.4480 | 194 |
| 30 | 32.6800 | 2.73800 | 25 | 12 | 0.7466 | 350 |
| 31 | 33.2000 | 2.69629 | 7 | 3 | 0.0000 | 0 |
| 32 | 36.0700 | 2.48807 | 15 | 7 | 0.4200 | 181 |
| 33 | 36.5600 | 2.45584 | 7 | 3 | 0.2000 | 62 |
| 34 | 41.8000 | 2.15929 | 7 | 3 | 0.4000 | 89 |
| 35 | 43.2000 | 2.09250 | 6 | 3 | 0.2400 | 68 |

Peak Data List for FIG. 22

Peak Data List

| No. | 2Theta (degrees) | d (A) | I (counts) | I/Io | FWHM (degrees) | integrated I (counts) |
|---|---|---|---|---|---|---|
| 1 | 3.6075 | 24.47248 | 26 | 6 | 0.1650 | 147 |
| 2 | 3.9600 | 22.29481 | 34 | 7 | 0.2134 | 165 |
| 3 | 4.3031 | 20.51791 | 80 | 18 | 0.3205 | 723 |
| 4 | 6.2414 | 14.14964 | 17 | 4 | 0.0611 | 38 |
| 5 | 7.2400 | 12.20009 | 36 | 8 | 0.2036 | 394 |
| 6 | 7.7200 | 11.44258 | 426 | 94 | 0.3118 | 3303 |
| 7 | 8.0000 | 11.04270 | 330 | 73 | 0.2948 | 2715 |
| 8 | 8.7200 | 10.13247 | 54 | 12 | 0.4266 | 848 |
| 9 | 9.6800 | 9.12964 | 14 | 3 | 0.2900 | 105 |
| 10 | 9.9628 | 8.87112 | 44 | 10 | 0.3257 | 342 |
| 11 | 11.0298 | 8.01522 | 57 | 13 | 0.3243 | 526 |
| 12 | 12.3200 | 7.17858 | 51 | 11 | 0.2400 | 405 |
| 13 | 12.6400 | 6.99756 | 165 | 36 | 0.3244 | 1564 |
| 14 | 13.1212 | 6.74199 | 374 | 82 | 0.3888 | 3658 |
| 15 | 13.6800 | 6.46783 | 68 | 15 | 0.1688 | 889 |
| 16 | 14.8000 | 5.98079 | 18 | 4 | 0.0000 | 0 |
| 17 | 15.3342 | 5.77362 | 60 | 13 | 0.3396 | 734 |
| 18 | 15.9420 | 5.55484 | 40 | 9 | 0.2760 | 345 |
| 19 | 16.5868 | 5.34032 | 202 | 44 | 0.3160 | 1701 |
| 20 | 17.5000 | 5.06365 | 24 | 5 | 0.1400 | 105 |
| 21 | 18.0400 | 4.91328 | 141 | 31 | 0.2892 | 1111 |
| 22 | 18.4697 | 4.79993 | 188 | 41 | 0.3518 | 1617 |
| 23 | 19.4688 | 4.55580 | 165 | 36 | 0.3205 | 1292 |
| 24 | 19.9363 | 4.45001 | 70 | 15 | 0.2726 | 513 |
| 25 | 20.6000 | 4.30811 | 60 | 13 | 0.1792 | 380 |
| 26 | 21.2273 | 4.18220 | 455 | 100 | 0.3783 | 4610 |
| 27 | 21.9152 | 4.05245 | 15 | 3 | 0.0526 | 39 |
| 28 | 22.6000 | 3.93118 | 119 | 26 | 0.2830 | 1096 |
| 29 | 23.2970 | 3.81512 | 282 | 62 | 0.4626 | 3282 |
| 30 | 23.8977 | 3.72057 | 165 | 36 | 0.4917 | 1965 |
| 31 | 24.4800 | 3.63337 | 89 | 20 | 0.3152 | 885 |
| 32 | 25.1600 | 3.53669 | 108 | 24 | 0.2244 | 662 |
| 33 | 25.4800 | 3.49299 | 86 | 19 | 0.3032 | 1025 |
| 34 | 25.9600 | 3.42949 | 57 | 13 | 0.0000 | 0 |
| 35 | 26.6611 | 3.34087 | 217 | 48 | 0.6191 | 3485 |
| 36 | 27.8800 | 3.19752 | 89 | 20 | 0.4492 | 976 |
| 37 | 28.2400 | 3.15757 | 123 | 27 | 0.2800 | 936 |
| 38 | 29.0688 | 3.06940 | 94 | 21 | 0.2546 | 702 |
| 39 | 29.5600 | 3.01950 | 57 | 13 | 0.1400 | 218 |
| 40 | 29.8400 | 2.99180 | 62 | 14 | 0.3074 | 607 |
| 41 | 31.1200 | 2.87160 | 48 | 11 | 0.4500 | 530 |
| 42 | 31.5126 | 2.83672 | 95 | 21 | 0.2739 | 584 |
| 43 | 31.9200 | 2.80144 | 49 | 11 | 0.2886 | 396 |
| 44 | 32.7342 | 2.73359 | 66 | 15 | 0.4432 | 626 |
| 45 | 33.2000 | 2.69629 | 53 | 12 | 0.2978 | 363 |
| 46 | 33.5500 | 2.66896 | 51 | 11 | 0.3572 | 422 |
| 47 | 34.2632 | 2.61502 | 25 | 5 | 0.1722 | 163 |
| 48 | 35.3161 | 2.53943 | 50 | 11 | 0.2477 | 265 |
| 49 | 35.5392 | 2.52400 | 50 | 11 | 0.1985 | 337 |
| 50 | 36.2800 | 2.47414 | 35 | 8 | 0.0800 | 163 |

Peak Data List for FIG. 27

Peak Data List

| No. | 2Theta (degrees) | d (A) | I (counts) | I/Io | FWHM (degrees) | integrated I (counts) |
|---|---|---|---|---|---|---|
| 1 | 3.1200 | 28.29512 | 51 | 10 | 0.1458 | 205 |
| 2 | 3.5556 | 24.82958 | 38 | 7 | 0.0928 | 186 |
| 3 | 4.3943 | 20.09228 | 28 | 5 | 0.1014 | 143 |
| 4 | 4.7950 | 18.41411 | 31 | 6 | 0.0900 | 108 |
| 5 | 5.2227 | 16.90705 | 16 | 3 | 0.0879 | 43 |
| 6 | 6.6800 | 13.22154 | 74 | 14 | 0.1482 | 536 |
| 7 | 7.0596 | 12.51144 | 309 | 58 | 0.1992 | 1985 |
| 8 | 8.5211 | 10.36853 | 18 | 3 | 0.0577 | 43 |
| 9 | 8.9240 | 9.90130 | 16 | 3 | 0.0880 | 67 |
| 10 | 9.4400 | 9.36121 | 88 | 17 | 0.1866 | 782 |
| 11 | 9.7646 | 9.05073 | 532 | 100 | 0.2263 | 3059 |
| 12 | 10.1600 | 8.69937 | 40 | 8 | 0.1908 | 525 |
| 13 | 10.6800 | 8.27695 | 38 | 7 | 0.1292 | 176 |
| 14 | 11.0021 | 8.03534 | 226 | 42 | 0.2376 | 1509 |
| 15 | 11.3600 | 7.78298 | 26 | 5 | 0.1150 | 169 |
| 16 | 13.0470 | 6.78017 | 93 | 17 | 0.2260 | 647 |
| 17 | 14.0525 | 6.29721 | 246 | 46 | 0.3632 | 2430 |
| 18 | 14.6791 | 6.02978 | 71 | 13 | 0.2258 | 452 |
| 19 | 15.5752 | 5.68482 | 50 | 9 | 0.3238 | 373 |
| 20 | 15.9988 | 5.53525 | 64 | 12 | 0.2511 | 414 |
| 21 | 16.4000 | 5.40073 | 43 | 8 | 0.1666 | 204 |
| 22 | 16.7463 | 5.28982 | 94 | 18 | 0.2474 | 621 |
| 23 | 17.7700 | 4.98732 | 270 | 51 | 0.2527 | 1705 |
| 24 | 18.1200 | 4.89177 | 89 | 17 | 0.3128 | 758 |
| 25 | 18.4843 | 4.79617 | 109 | 20 | 0.2930 | 804 |
| 26 | 19.0910 | 4.64510 | 34 | 6 | 0.1321 | 116 |
| 27 | 20.2740 | 4.37664 | 158 | 30 | 0.3763 | 1451 |
| 28 | 20.6400 | 4.29985 | 144 | 27 | 0.2316 | 710 |
| 29 | 21.0400 | 4.21900 | 133 | 25 | 0.4290 | 1643 |
| 30 | 21.4400 | 4.14118 | 231 | 43 | 0.2254 | 1401 |
| 31 | 21.9901 | 4.03882 | 37 | 7 | 0.2140 | 187 |
| 32 | 22.2000 | 4.00110 | 22 | 4 | 0.1600 | 120 |
| 33 | 22.6083 | 3.92976 | 37 | 7 | 0.1583 | 182 |
| 34 | 23.2000 | 3.83085 | 49 | 9 | 0.1800 | 331 |
| 35 | 23.6500 | 3.75897 | 237 | 45 | 0.3000 | 1961 |
| 36 | 24.0000 | 3.70494 | 49 | 9 | 0.1494 | 328 |
| 37 | 24.5063 | 3.62953 | 30 | 6 | 0.1660 | 146 |
| 38 | 24.9600 | 3.56457 | 64 | 12 | 0.2742 | 540 |
| 39 | 25.5385 | 3.48512 | 262 | 49 | 0.3049 | 1992 |
| 40 | 26.0000 | 3.42430 | 125 | 23 | 0.4572 | 1443 |
| 41 | 26.6124 | 3.34687 | 221 | 42 | 0.3039 | 1600 |
| 42 | 26.9200 | 3.30933 | 71 | 13 | 0.2266 | 450 |
| 43 | 27.3600 | 3.25710 | 150 | 28 | 0.1894 | 671 |
| 44 | 27.5600 | 3.23391 | 167 | 31 | 0.3146 | 1087 |
| 45 | 28.1427 | 3.16826 | 104 | 20 | 0.5040 | 1245 |
| 46 | 29.3165 | 3.04403 | 28 | 5 | 0.1989 | 191 |
| 47 | 29.7200 | 3.00361 | 83 | 16 | 0.2000 | 497 |
| 48 | 30.0400 | 2.97234 | 177 | 33 | 0.2770 | 1270 |
| 49 | 30.4000 | 2.93795 | 92 | 17 | 0.2588 | 761 |
| 50 | 31.4461 | 2.84256 | 20 | 4 | 0.1477 | 154 |

While specific embodiments of the present invention have been described in the foregoing, it will be appreciated by those skilled in the art that many equivalents, modifications, substitutions, and variations may be made thereto without departing from the spirit and scope of the invention as defined in the appended claims.

What is claimed is:

1. A brimonidine pamoate polymorph exhibiting an X-ray powder diffraction spectrum comprising peaks at 2θ angles of 9.7°, 14.6°, 25.9° and 26.5°±0.2°.

2. A pharmaceutical composition comprising a pharmaceutically acceptable carrier and a brimonidine pamoate polymorph of claim 1.

3. The pharmaceutical composition of claim 2, wherein the pharmaceutically acceptable carrier comprises an aqueous medium.

4. The pharmaceutical composition of claim 2, wherein the pharmaceutically acceptable carrier comprises an organic medium.

5. A method for producing the brimonidine pamoate polymorph of claim 1, said method comprising: contacting a brimonidine pamoate polymorph that exhibits an X-ray powder diffraction spectrum comprising peaks at 2θ angles of 13.5°, 20.6°, 21.1° and 24.4°±0.2°, with (i) water, or (ii) a mixture of N,N-dimethylformamide and water.

* * * * *